US012806153B2

(12) United States Patent
Murphy et al.

(10) Patent No.: US 12,806,153 B2
(45) Date of Patent: Nov. 24, 2026

(54) POLYACETYLENE COMPOUNDS FOR TREATING INFLAMMATORY DISEASES

(71) Applicant: UNIVERSITY OF SOUTH CAROLINA, Columbia, SC (US)

(72) Inventors: Elizabeth A. Murphy, Columbia, SC (US); Lorne Hofseth, Columbia, SC (US)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 516 days.

(21) Appl. No.: 18/455,124

(22) Filed: Aug. 24, 2023

(65) Prior Publication Data

US 2024/0091169 A1 Mar. 21, 2024

Related U.S. Application Data

(60) Provisional application No. 63/400,629, filed on Aug. 24, 2022.

(51) Int. Cl.

| | |
|---|---|
| ***A61K 31/045*** | (2006.01) |
| ***A61P 1/00*** | (2006.01) |
| ***A61P 35/00*** | (2006.01) |
| ***G01N 33/50*** | (2006.01) |

(52) U.S. Cl.

CPC .............. *A61K 31/045* (2013.01); *A61P 1/00* (2018.01); *A61P 35/00* (2018.01); *G01N 33/5008* (2013.01); *G01N 2800/52* (2013.01)

(58) Field of Classification Search

None

See application file for complete search history.

(56) References Cited

U.S. PATENT DOCUMENTS

2020/0222557 A1 7/2020 Berlin et al.

FOREIGN PATENT DOCUMENTS

| | | | | |
|---|---|---|---|---|
| KR | 20160065402 A | * | 6/2016 | ........... A61K 36/258 |
| WO | WO-9634943 A1 | * | 11/1996 | ................ A61P 9/10 |

OTHER PUBLICATIONS

Chen et al. Fitoterapia 167 (2023) 105490 (Year: 2023).*

Alice Grigore "Targeting Tumor-Associated Macrophages by Plant Compounds". 2021, IntechOpen.

Almeida et al. "Intestinal anti-inflammatory activity of Ground Cherry (*Physalis angulata* L.) standardized CO(2) phytopharmaceutical preparation". World J Gastroenterol, 2017. 23(24): p. 4369-4380.

Amend et al. "Murine Hind Limb Long Bone Dissection and Bone Marrow Isolation". J Vis Exp, 2016(110).

Aristin Revilla et al. "Colorectal Cancer-Infiltrating Regulatory T Cells: Functional Heterogeneity, Metabolic Adaptation, and Therapeutic Targeting". Front Immunol, 2022. 13: p. 903564.

Bader et al. "Macrophage depletion using clodronate liposomes decreases tumorigenesis and alters gut microbiota in the AOM/DSS mouse model of colon cancer". Am J Physiol Gastrointest Liver Physiol, 2018. 314(1): p. G22-G31.

Bhala et al. "Disease activity, burden and suffering in patients with ulcerative colitis in the UK cohort recruited into the global ICONIC study." Frontline Gastroenterol, 2023. 14(1): p. 25-31.

Bullard et al. "Cross talk between the gut microbiome and host immune response in ulcerative colitis: nonpharmacological strategies to improve homeostasis". Am J Physiol Gastrointest Liver Physiol, 2022. 323(6): p. G554-G561.

Cantorna et al. "Vitamin D Regulates the Microbiota to Control the Nos. of RORgammat/FoxP3+ Regulatory T Cells in the Colon". Front Immunol, 2019. 10: p. 1772.

Chaparala et al. "Molecules from American Ginseng Suppress Colitis through Nuclear Factor Erythroid-2-Related Factor 2". Nutrients, 2020. 12(6).

Chaparala et al. "Panaxynol, a bioactive component of American ginseng, targets macrophages and suppresses colitis in mice". Oncotarget, 2020. 11(22): p. 2026-2036.

Chassaing et al. "Dextran sulfate sodium (DSS)-induced colitis in mice". Curr Protoc Immunol, 2014. 104: p. 15 25 1-15 25 14.

Chelakkot et al. "Mechanisms regulating intestinal barrier integrity and its pathological implications". Experimental & Molecular Medicine, 2018. 50(8): p. 1-9.

Chen et al. "Overcoming Resistance to Targeted Therapies in Gastrointestinal Cancers: Progress to Date and Progress to Come". Am Soc Clin Oncol Educ Book, 2020. 40: p. 161-173.

Cohen et al. "Systematic review: the costs of ulcerative colitis in Western countries". Aliment Pharmacol Ther, 2010. 31(7): p. 693-707.

Cranford et al. "Effects of high fat diet-induced obesity on mammary tumorigenesis in the PyMT/MMTV murine model". Cancer Biol Ther, 2019. 20(4): p. 487-496.

Cui et al. "Mechanistic insight into the ability of American ginseng to suppress colon cancer associated with colitis". Carcinogenesis, 2010. 31(10): p. 1734-41.

Deng et al. "Natural products and their derivatives: Promising modulators of tumor immunotherapy". J Leukoc Biol, 2020. 108(2): p. 493-508.

Dharmasiri et al. "Human Intestinal Macrophages Are Involved in the Pathology of Both Ulcerative Colitis and Crohn Disease". Inflamm Bowel Dis, 2021. 27(10): p. 1641-1652.

Enos et al. "Influence of dietary saturated fat content on adiposity, macrophage behavior, inflammation, and metabolism: composition matters". J Lipid Res, 2013. 54(1): p. 152-63.

Enos et al. "Lowering the dietary omega-6: omega-3 does not hinder nonalcoholic fatty-liver disease development in a murine model". Nutr Res, 2015. 35(5): p. 449-59.

(Continued)

*Primary Examiner* — Sarah Pihonak
*Assistant Examiner* — Donna M Nestor
(74) *Attorney, Agent, or Firm* — Dority & Manning, P.A.

(57) ABSTRACT

In general, disclosed herein are methods of treating an inflammatory disease or disorder by administering to the subject in need thereof a polyacetylene compound. The polyacetylene compound may be administered at a dose of from about 1 mg/kg body weight to about 10 mg/kg body weight.

10 Claims, 43 Drawing Sheets

(56) References Cited

OTHER PUBLICATIONS

Feofanova et al. "L-fucose reduces gut inflammation due to T-regulatory response in Muc2 null mice". PLoS One, 2022. 17(12): p. e0278714.
Fujino et al. "Hepatocyte growth factor ameliorates dextran sodium sulfate-induced colitis in a mouse model by altering the phenotype of intestinal macrophages". Mol Med Rep, 2023. 27(3).
Grondin et al. "Mucins in Intestinal Mucosal Defense and Inflammation: Learning From Clinical and Experimental Studies". Front Immunol, 2020. 11: p. 2054.
Grotto et al. "The Standard American Diet and its relationship to the health status of Americans". Nutr Clin Pract, 2010. 25(6): p. 603-12.
Han et al. "Roles of Macrophages in the Development and Treatment of Gut Inflammation". Front Cell Dev Biol, 2021. 9: p. 625423.
Hayakawa et al. "Hydroxyapatite-coated titanium oxide ameliorates dextran sulphate sodium-induced colitis by attenuating both innate and acquired immune reaction". Prz Gastroenterol, 2023. 18(1): p. 76-84.
Himmel et al. "Regulatory T-cell therapy for inflammatory bowel disease: more questions than answers". Immunology, 2012. 136(2): p. 115-22.
Huang et al. "Natural products for treating colorectal cancer: A mechanistic review". Biomed Pharmacother, 2019. 117: p. 109142.
Islam et al. "Colon cancer and colorectal cancer: Prevention and treatment by potential natural products". Chemico-Biological Interactions, 2022. 368: p. 110170.
Iwanowycz et al. "Emodin Bidirectionally Modulates Macrophage Polarization and Epigenetically Regulates Macrophage Memory". J Biol Chem, 2016. 291(22): p. 11491-503.
Jin et al. "American Ginseng Suppresses Colitis through p53-Mediated Apoptosis of Inflammatory Cells". Cancer Prevention Research, 2010. 3(3): p. 339-347.
Jin et al. "American ginseng suppresses inflammation and DNA damage associated with mouse colitis". Carcinogenesis, 2008. 29(12): p. 2351-2359.
Kaye E. Hale, Toxicities of Chemotherapy, in Principles of Critical Care, 4e, J.B. Hall, G.A. Schmidt, and J.P. Kress, Editors. 2015, McGraw-Hill Education: New York, NY.
Kim et al. "Effects of ginsenosides on regulatory T cell differentiation". Food Sci Biotechnol, 2018. 27(1): p. 227-232.
Kobaek-Larsen et al. "Dietary polyacetylenes, falcarinol and falcarindiol, isolated from carrots prevents the formation of neoplastic lesions in the colon of azoxymethane-induced rats". Food Funct, 2017. 8(3): p. 964-974.
Kobaek-Larsen et al. "Effect of the dietary polyacetylenes falcarinol and falcarindiol on the gut microbiota composition in a rat model of colorectal cancer". BMC Res Notes, 2018. 11(1): p. 411.
Kodani et al. "Flexible colonoscopy in mice to evaluate the severity of colitis and colorectal tumors using a validated endoscopic scoring system". J Vis Exp, 2013(80): p. e50843.
Kubinak et al. "MyD88 signaling in T cells directs IgA-mediated control of the microbiota to promote health". Cell Host Microbe, 2015. 17(2): p. 153-63.
Li et al. "Colorectal Cancer in Ulcerative Colitis: Mechanisms, Surveillance and Chemoprevention". Curr Oncol, 2022. 29(9): p. 6091-6114.
Li et al. "Huangqin Decoction ameliorates ulcerative colitis by regulating fatty acid metabolism to mediate macrophage polarization via activating FFAR4-AMPK-PPARalpha pathway". J Ethnopharmacol, 2023. 311: p. 116430.
Li et al. "Prognostic and clinicopathological value of MUCI expression in colorectal cancer: A meta-analysis". Medicine, 2019. 98(9).
Li et al. "Rabdosia serra alleviates dextran sulfate sodium salt-induced colitis in mice through anti-inflammation, regulating Th17/Treg balance, maintaining intestinal barrier integrity, and modulating gut microbiota". J Pharm Anal, 2022. 12(6): p. 824-838.
Linda Chia-Hui Yu "Microbiota dysbiosis and barrier dysfunction in inflammatory bowel disease and colorectal cancers: exploring a common ground hypothesis". Journal of Biomedical Science, 2018. 25(1).
Liu et al. "The role of MUC2 mucin in intestinal homeostasis and the impact of dietary components on MUC2 expression". International Journal of Biological Macromolecules, 2020. 164: p. 884-891.
Lu et al. "Ginseng Compounds: An Update on their Molecular Mechanisms and Medical Applications". Current Vascular Pharmacology, 2009. 7(3): p. 293-302.
Majeed et al. "Ginseng phytochemicals as therapeutics in oncology: Recent perspectives". Biomedicine & Pharmacotherapy, 2018. 100: p. 52-63.
Mazaki et al. "Neutrophil-to-lymphocyte ratio is a prognostic factor for colon cancer: a propensity score analysis". BMC Cancer, 2020. 20(1): p. 922.
Mcculloch et al. "Colon Cancer Survival With Herbal Medicine and Vitamins Combined With Standard Therapy in a Whole-Systems Approach: Ten-Year Follow-up Data Analyzed With Marginal Structural Models and Propensity Score Methods". Integrative Cancer Therapies, 2011. 10(3): p. 240-259.
Mcdonald et al. "Surgical wounding enhances pro-tumor macrophage responses and accelerates tumor growth and lung metastasis in a triple negative breast cancer mouse model". Physiol Rep, 2022. 10(21): p. e15497.
Mcdonald et al. Abstract "Panaxynol Alleviates Colorectal Cancer in a Murine Model via Suppressing Macrophages and Inflammation" American Journal of Physiology-Gastrointestinal and Liver Physiology, Jul. 25, 2023.
Meng et al. "HnRNPA2B1 Aggravates Inflammation by Promoting M1 Macrophage Polarization". Nutrients, 2023. 15(7).
Mizuno et al. "The Role of Tumor-Associated Neutrophils in Colorectal Cancer". Int J Mol Sci, 2019. 20(3).
Moudgil et al. "The Anti-Inflammatory and Immunomodulatory Activities of Natural Products to Control Autoimmune Inflammation". Int J Mol Sci, 2022. 24(1).
Na et al. "Macrophages in intestinal inflammation and resolution: a potential therapeutic target in IBD". Nat Rev Gastroenterol Hepatol, 2019. 16(9): p. 531-543.
National Cancer Institute Pamphlets "Seer stat fact sheets: colon and rectum cancer". Based on 2011-2013 SEER data, 2016.
Nielsen et al. "Macrophages as Key Drivers of Cancer Progression and Metastasis". Mediators Inflamm, 2017. 2017: p. 9624760.
Ning et al. "Qingre Xingyu recipe exerts inhibiting effects on ulcerative colitis development by inhibiting TNFalpha/NLRP3/Caspase-1/IL-1beta pathway and macrophage M1 polarization". Cell Death Discov, 2023. 9(1): p. 84.
Olguin et al. "Relevance of Regulatory T Cells during Colorectal Cancer Development". Cancers, 2020. 12(7): p. 1888.
Poudyal et al. "A Hexane Fraction of American Ginseng Suppresses Mouse Colitis and Associated Colon Cancer: Anti-inflammatory and Proapoptotic Mechanisms". Cancer Prevention Research, 2012. 5(4): p. 685-696.
Poudyal et al. "A Key Role of microRNA-29b for the Suppression of Colon Cancer Cell Migration by American Ginseng". PLoS ONE, 2013. 8(10): p. e75034.
Poudyal et al. "A Limited Role of p53 on the Ability of a Hexane Fraction of American Ginseng to Suppress Mouse Colitis". Journal of Biomedicine and Biotechnology, 2012. 2012: p. 1-11.
Ri et al. "Narirutin exerts anti-inflammatory activity by inhibiting NLRP3 inflammasome activation in macrophages". Phytother Res, 2023. 37(4): p. 1293-1308.
Rizzardi et al. "Quantitative comparison of immunohistochemical staining measured by digital image analysis versus pathologist visual scoring". Diagn Pathol, 2012. 7: p. 42.
Sathish et al. "Challenges and approaches for the development of safer immunomodulatory biologics". Nat Rev Drug Discov, 2013. 12(4): p. 306-24.
Seca et al. "Plant Secondary Metabolites as Anticancer Agents: Successes in Clinical Trials and Therapeutic Application". Int J Mol Sci, 2018. 19(1).

(56) References Cited

OTHER PUBLICATIONS

Sergiu Coseri "Natural products and their analogues as efficient anticancer drugs". Mini Rev Med Chem, 2009. 9(5): p. 560-71.
Shatila et al. "Effects of immunosuppressive treatment on patient outcomes after immune checkpoint inhibitor-related gastrointestinal toxicity". J Cancer Res Clin Oncol, 2023.
Sipola et al. "Histological damage of colonic epithelium is associated with clinical severity and outcome in colectomized critically Ill patients". World J Surg, 2014. 38(5): p. 1211-6.
Sougiannis et al. "Emodin reduces tumor burden by diminishing M2-like macrophages in colorectal cancer". Am J Physiol Gastrointest Liver Physiol, 2022. 322(3): p. G383-G395.
Sung et al. "Global Cancer Statistics 2020: GLOBOCAN Estimates of Incidence and Mortality Worldwide for 36 Cancers in 185 Countries". CA Cancer J Clin, 2021. 71(3): p. 209-249.
Szczuka et al. "American Ginseng (*Panax quinquefolium* L.) as a Source of Bioactive Phytochemicals with Pro-Health Properties". Nutrients, 2019. 11(5): p. 1041.
Taieb et al. "Refining adjuvant therapy for non-metastatic colon cancer, new standards and perspectives". Cancer Treat Rev, 2019. 75: p. 1-11.
Tan et al. "Biodiversity as a source of anticancer drugs". Curr Drug Targets, 2006. 7(3): p. 265-77.
Vander Veen et al. "5-Fluorouracil disrupts skeletal muscle immune cells and impairs skeletal muscle repair and remodeling". J Appl Physiol (1985), 2022. 133(4): p. 834-849.
Villanacci et al. "Histological healing in inflammatory bowel disease: a still unfulfilled promise". World J Gastroenterol, 2013. 19(7): p. 968-78.
Villanacci et al. "Histopathology of IBD Colitis. A practical approach from the pathologists of the Italian Group for the study of the gastrointestinal tract (GIPAD)". Pathologica, 2021. 113(1): p. 39-53.
Volarevic et al. "Galectin-3 Regulates Indoleamine-2,3-dioxygenase-Dependent Cross-Talk between Colon-Infiltrating Dendritic Cells and T Regulatory Cells and May Represent a Valuable Biomarker for Monitoring the Progression of Ulcerative Colitis". Cells, 2019. 8(7).
Wang et al. American Ginseng Attenuates Colitis-Associated Colon Carcinogenesis in Mice: Impact on Gut Microbiota and Metabolomics. Cancer Prev Res (Phila), 2016. 9(10): p. 803-811.
Wang et al. "American ginseng microbial metabolites attenuate DSS-induced colitis and abdominal pain". Int Immunopharmacol, 2018. 64: p. 246-251.
Wang et al. "Fecal metabolomic dataset of American ginseng-treated DSS mice: Correlation between ginseng enteric inflammation inhibition and its biological signatures". Data Brief, 2018. 21: p. 1403-1408.
Wang et al. "Preventive effect of pectic oligosaccharides on acute colitis model mice: modulating epithelial barrier, gut microbiota and Treg/Th17 balance". Food Funct, 2022. 13(19): p. 9999-10012.
Wang et al. "Role of intestinal microbiome in American ginseng-mediated colon cancer prevention in high fat diet-fed AOM/DSS mice". Clin Transl Oncol, 2018. 20(3): p. 302-312.
Wang et al. "Tumor-Associated Macrophages (TAMs) in Colorectal Cancer (CRC): From Mechanism to Therapy and Prognosis". International Journal of Molecular Sciences, 2021. 22(16): p. 8470.
Warden et al. "Comparisons of diets used in animal models of high-fat feeding". Cell Metab, 2008. 7(4): p. 277.
Wei et al. "Curcumin ameliorates DSS-induced colitis in mice by regulating the Treg/Th17 signaling pathway". Mol Med Rep, 2021. 23(1).
Xu et al. "Embryonic stem cell-derived mesenchymal stem cells promote colon epithelial integrity and regeneration by elevating circulating IGF-1 in colitis mice". Theranostics, 2020. 10(26): p. 12204-12222.
Yamada et al. "Role of regulatory T cell in the pathogenesis of inflammatory bowel disease". World J Gastroenterol, 2016. 22(7): p. 2195-205.
Ying et al. "Investigation of macrophage polarization using bone marrow derived macrophages". J Vis Exp, 2013(76).
Yu et al. "American ginseng attenuates azoxymethane/dextran sodium sulfate-induced colon carcinogenesis in mice". J Ginseng Res, 2015. 39(1): p. 14-21.
Zhang et al. "Cepharanthine Alleviates DSS-Induced Ulcerative Colitis via Regulating Aconitate Decarboxylase 1 Expression and Macrophage Infiltration". Molecules, 2023. 28(3).
Zhang et al. "Dietary High Dose of Iron Aggravates the Intestinal Injury but Promotes Intestinal Regeneration by Regulating Intestinal Stem Cells Activity in Adult Mice With Dextran Sodium Sulfate-Induced Colitis". Front Vet Sci, 2022. 9: p. 870303.
Zhang et al. "Macrophage-based nanotherapeutic strategies in ulcerative colitis". J Control Release, 2020. 320: p. 363-380.
Zhao et al. "Effect of toll-like receptor 3 agonist poly I:C on intestinal mucosa and epithelial barrier function in mouse models of acute colitis". World J Gastroenterol, 2017. 23(6): p. 999-1009.
Zhao et al. "Protective role of 1,25(OH)2 vitamin D3 in the mucosal injury and epithelial barrier disruption in DSS-induced acute colitis in mice". BMC Gastroenterol, 2012. 12: p. 57.
Zhong et al. "The Role of Tumor-Associated Macrophages in Colorectal Carcinoma Progression. Cellular Physiology and Biochemistry", 2018. 45(1): p. 356-365.
Zhou et al. "The Synergistic Effects of Polysaccharides and Ginsenosides From American Ginseng (*Panax quinquefolius* L.) Ameliorating Cyclophosphamide-Induced Intestinal Immune Disorders and Gut Barrier Dysfunctions Based on Microbiome-Metabolomics Analysis". Front Immunol, 2021. 12: p. 665901.

* cited by examiner

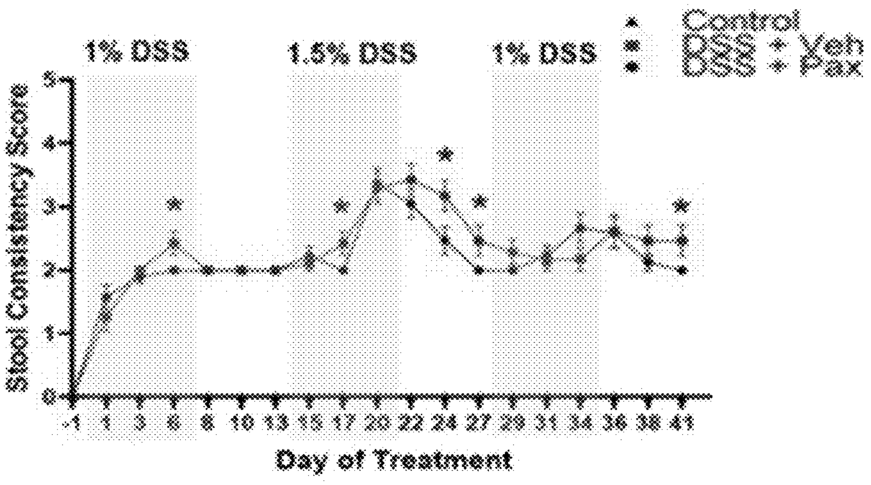
FIG. 9B (1B)
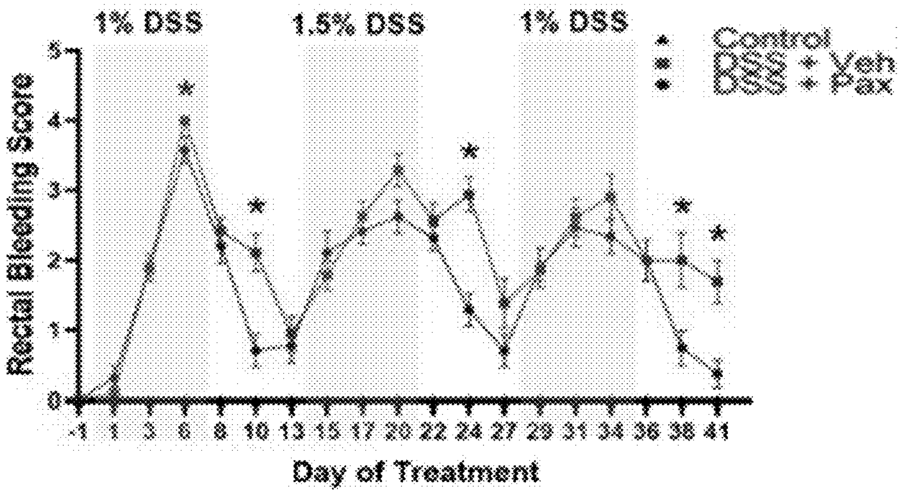
FIG. 9C (1C)
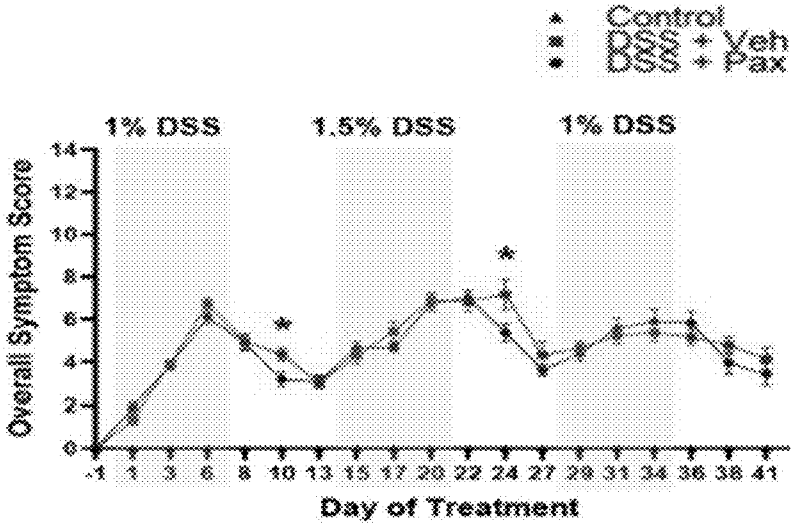
FIG. 9D (1D)

DSS+Pax

DSS+Veh

POLYACETYLENE COMPOUNDS FOR TREATING INFLAMMATORY DISEASES

CROSS REFERENCE TO RELATED APPLICATIONS

This application claims the filing benefit of U.S. Provisional Patent Application Ser. No. 63/400,629, filed on Aug. 24, 2022, which is incorporated herein by reference.

GOVERNMENT SUPPORT CLAUSE

This invention was made with government support under R01CA246809 awarded by National Institutes of Health (NIH). The government has certain rights in the invention.

BACKGROUND

Inflammatory diseases impact millions worldwide. However, if available, current therapeutics primarily treat disease symptoms and may have undesirable off-target effects. For instance, medicine for ulcerative colitis (UC), an idiopathic inflammatory disease of the large intestine, primarily exists to treat the symptoms of UC, these drugs (specifically antibiotics, corticosteroids, NSAIDs, and cytokine inhibitors). Said medicines can result in off-target effects and immunosuppression, further contributing to decreased quality of life for UC patients. Similarly, available colorectal cancer (CRC) therapies have limited efficacy and severe adverse effects. In fact, many CRC patients receiving chemotherapy experience issues of non-specific toxicity, pervasive off-target effects, and acquired drug resistance, resulting in reduced quality of life, treatment cessation, or need for alternative treatment regimens.

*Ginseng* is one of the most widely used herbal medicines and best-selling natural products worldwide. American *Ginseng* (AG) is a plant rich in bioactive phytochemicals with its active components (ginsenosides) documented to exert immunomodulatory, anti-inflammatory, anti-cancer, and chemo-protective effects. Isolated, active components of *Ginseng* exhibit more potent antioxidant and pro-apoptotic properties.

As such, what is needed in the art are clinically effective compositions and methods for treating and/or suppressing inflammatory diseases.

SUMMARY

In general, disclosed herein are methods of treating an inflammatory disease or disorder by administering to the subject in need thereof a polyacetylene compound. The polyacetylene compound may be administered at a dose of from about 1 mg/kg body weight to about 10 mg/kg body weight.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which:

FIG. 9B illustrates stool consistency score quantified using disease activity index (n=5-10/group).

FIG. 9C illustrates rectal bleeding score quantified using disease activity index (n=5-10/group).

FIG. 9D illustrates overall symptom score quantified using disease activity index (n=5-10/group).

Figure 1A:
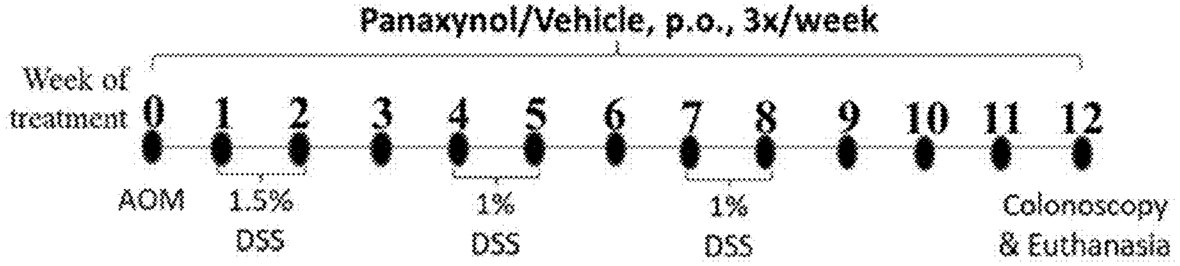
FIG. 1A illustrates schematic of experimental design to induce AOM/DSS-induced CRC using 11-week-old C57BL/6 female (n=20) and male (n=20) mice over 12 weeks.

Repeat use of reference characters in the present specification and drawings is intended to represent the same or analogous features or elements of the present invention.

DETAILED DESCRIPTION

Reference will now be made in detail to various embodiments of the presently disclosed subject matter, one or more examples of which are set forth below. Each embodiment is provided by way of explanation, not limitation, of the subject matter. In fact, it will be apparent to those skilled in the art that various modifications and variations may be made to the present disclosure without departing from the scope or spirit of the disclosure. For instance, features illustrated or described as part of one embodiment, may be used in another embodiment to yield a still further embodiment. Thus, it is intended that the present disclosure cover such modifications and variations as come within the scope of the appended claims and their equivalents.

In general, disclosed herein are methods of treating an inflammatory disease or disorder by administering to the subject in need thereof a polyacetylene compound. The term "treating" as used herein refers to partially or completely alleviating, improving, relieving, inhibiting progression, and/or reducing incidence of one or more symptoms of an inflammatory disease or disorder.

In one embodiment, a subject in need thereof may be administered a polyacetylene compound. As used herein, a "polyacetylene compound" refers to compounds isolated from natural sources, such as fungi or plants. For instance, the polyacetylene compound may be an anti-tumor agent.

In one embodiment, the polyacetylene compound may be panaxynol (3(R)-(9Z)-heptadeca-1, 9-dien-4,6-diyn-3-ol. Panaxynol is an isolated, bioactive component in American *Ginseng*. Panaxynol has the following chemical formula: $C_{17}H_{24}O$. Panaxynol has the following chemical formula:

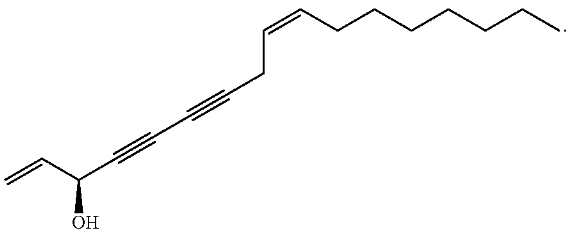 [SMILES: C=C[C@H](O)C#CC#CC/C=C\CCCCCCC]

In one embodiment, the polyacetylene compound may be administered at a dose of from about 1 mg/kg body weight to about 10 mg/kg body weight, such as from about 1.5 mg/kg body weight to about 7.5 mg/kg body weight, such as from about 2 mg/kg body weight to about 5 mg/kg body weight, such as from about 2.5 mg/kg to about 4 mg/kg, or any range therebetween.

The duration of therapy will continue for as long as medically indicated or until a desired therapeutic effect (e.g., those described herein) is achieved. For instance, a subject can be treated until a complete response is acquired, such as until disease progression is delayed or inhibited. In one embodiment, the polyacetylene compound is administered daily for a period of about 1 day, about 2 days, about 3 days, about 4 days, about 5 days, about 6 days, about 7 days, about 10 days, about 14 days, about 21 days, about 28 days, about 6 weeks, about 8 weeks, or longer than 8 weeks following first administration. However, the course of treatment for any individual subject can be modified in clinical practice.

Methods disclosed herein are generally directed toward treating an inflammatory disease or disorder by administering to the subject in need thereof at least one panaxynol compound. The term "treating" may refer to partially or completely alleviating, ameliorating, improving, relieving, delaying onset of, inhibiting progression of, reducing severity of, and/or reducing incidence of one or more symptoms, features, or clinical manifestations of a particular disease, disorder, and/or condition, e.g., an inflammatory disease.

Treatment can be administered to a subject who does not exhibit signs of a disease, disorder, and/or condition (e.g., prior to an identifiable disease, disorder, and/or condition), and/or to a subject who exhibits only early signs of a disease, disorder, and/or condition for the purpose of decreasing the risk of developing pathology associated with the disease, disorder, and/or condition.

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. The inflammatory disease may include, but is not limited to, an inflammatory bowel disease, colon cancer, colitis-associated colon cancer, colorectal cancer, psoriasis, colorectal cancer, chronic inflammation, an autoimmune disease, Familial Adenomatous Polyposis (FAP), and Lynch Syndrome.

In one embodiment, the inflammatory disease may be an inflammatory bowel disease. For instance, the inflammatory bowel disease may be selected from the group consisting of Crohn's disease, ulcerative colitis, collagenous colitis, lymphocytic colitis, ischaemic colitis, diversion colitis, microscopic colitis, left-sided colitis, pancolitis, and ileocolitis. In one embodiment, the inflammatory disease may be colitis.

In one embodiment, the inflammatory disease may be colorectal cancer including, but is not limited to, colon cancer, rectal cancer, or colorectal adenocarcinoma.

The term "subject" refers to any organism to which aspects of the disclosure can be administered, e.g., for experimental, diagnostic, prophylactic, and/or therapeutic purposes. Subjects to which embodiments of the disclosure can be administered include mammals, such as primates, for example, humans. For veterinary applications, a wide variety of subjects are suitable, e.g., livestock such as cattle, sheep, goats, cows, swine, and the like; poultry such as chickens, ducks, geese, turkeys, and the like; and domesticated animals, such as pets such as dogs and cats. For diagnostic or research applications, a wide variety of mammals are suitable subjects, including rodents (e.g., mice, rats, hamsters), rabbits, primates, and swine such as inbred pigs and the like. The term "living subject" can refer to a subject noted above or another organism that is alive. The term "living subject" can refer to the entire subject or organism and not just a part excised (e.g., a liver or other organ) from the living subject.

As used herein, the term "administering" refers to introducing a substance (e.g., a polyacetylene compound, an exogenous antigen, a cytotoxic agent, etc.) into a subject. The administration thereof can be carried out in any convenient manner, including by aerosol inhalation, injection, ingestion, transfusion, implantation, or transplantation. For instance, the polyacetylene compound may be administered orally, subcutaneously, intravenously, or intratumoral. In this regard, "oral" administration can refer to administration into a subject's mouth; "subcutaneous" administration can refer to administration just below the skin; "intravenous" administration can refer to administration into a vein of a subject; and "intratumoral" administration can refer to administration within a tumor.

Pharmaceutical compositions disclosed herein may be formulated to be compatible with its intended route of administration. As used herein, "routes of administration" may include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). The composition can be sterile and should be fluid to the extent that easy syringability exists. It can be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. Prolonged absorption of the injectable compositions may be brought about by including in the composition an agent that delays absorption, for example, aluminum monostearate and gelatin.

Oral compositions may include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Compositions for parenteral delivery, e.g., via injection, can include pharmaceutically acceptable sterile aqueous or nonaqueous solutions, dispersions, suspensions, or emulsions, as well as sterile powders for reconstitution into sterile injectable solutions or dispersions just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., corn oil) and injectable organic esters such as ethyl oleate. In addition, the composition can contain minor amounts of auxiliary substances such as wetting or emulsifying agents, pH buffering agents and the like that can enhance the effectiveness of the phenolic compound. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents, and dispersing agents.

In one embodiment, a therapeutically effective amount of the polyacetylene compound may be administered to the subject. The term "therapeutically effective amount" refers to those amounts that, when administered to a subject in view of the nature and severity of that subject's disease or condition, will have a desired therapeutic effect, e.g., an amount which will cure, prevent, inhibit, or at least partially arrest or partially prevent a target disease or condition. A therapeutically effective dose further can refer to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose can refer to that ingredient alone. When applied to a combination, a therapeutically effective dose can refer to combined amounts of the active ingredients that result in the therapeutic effect, whether administered in combination, serially or simultaneously.

A therapeutically effective dose can depend upon a number of factors known to those of ordinary skill in the art. The dosage can vary depending upon known factors such as the pharmacodynamic characteristics of the active ingredient and its mode and route of administration; time of administration of active ingredient; identity, size, condition, age, sex, health and weight of the subject or sample being treated; nature and extent of symptoms; kind of concurrent treatment, frequency of treatment and the effect desired; and rate of excretion. These amounts can be readily determined by the skilled artisan.

Prior to or following administration of the polyacetylene compound, a biological sample may be obtained from a subject to measure the presence or level of one or more biomarkers. As used herein, "obtaining a biological sample" refers to a process for directly or indirectly acquiring a biological sample from a subject. For instance, a biological sample may be obtained (e.g., at a point-of-care facility, e.g., a physician's office, a hospital, laboratory facility) by procuring a tissue or fluid sample (e.g., blood draw, marrow sample, spinal tap) from a subject. Alternatively, a biological sample can be obtained by receiving the biological sample (e.g., at a laboratory facility) from one or more persons who procured the sample directly from the subject. The biological sample can be, for example, a "biopsy tissue" or a "tumor sample," which refer to a sample of cells, tissues or fluids which is extracted from a subject, for example, in order to determine if the sample contains inflammation or to determine the gene expression profile or molecular profile of that tissue. The tissue or fluid may be examined to detect the presence or absence of one or more biomarkers of an autoimmune disease, including the presence of DNA and/or amino acid sequence mutations, molecular profile of the cells, and/or expression of the gene signature of cells.

The term "biomarker" may refer to mutations and/or molecules that can be evaluated in a biological sample (e.g., a biopsy tissue or a tumor sample) and are associated with a physical condition. For instance, biomarkers include expressed genes or their products (e.g., proteins) or antibodies to those proteins that can be detected from human samples, such as blood, serum, solid tissue, and the like, that is associated with a physical or disease condition. Such biomarkers include, but are not limited to, biomolecules comprising nucleotides, amino acids, sugars, fatty acids, steroids, metabolites, polypeptides, proteins (such as, but not limited to, antigens and antibodies), carbohydrates, lipids, hormones, antibodies, regions of interest which serve as surrogates for biological molecules, combinations thereof (e.g., glycoproteins, ribonucleoproteins, lipoproteins), and any complexes involving any such biomolecules, such as, but not limited to, a complex formed between an antigen and an autoantibody that binds to an available epitope on said antigen.

In one embodiment, the biomarker may comprise a cytokine, a cell, a micro-RNA, or any combination thereof. As used herein, "cytokine" refers to small, secreted proteins that regulate the intensity and duration of the immune response by affecting the immune cells differentiation process involving changes in gene expression by which a precursor cell becomes a distinct specialized cell type. For instance, the biomarker may comprise interleukin 10 (IL-10), interleukin 17+(IL-17+), interleukin 1β (IL-1β), interleukin 6 (IL-6), interleukin 13 (IL-1β), transforming growth factor-beta (TGF-β), Foxp3, or any combination thereof.

In one embodiment, the biomarker may comprise a cell. For instance, the cell may be a regulatory T cell (e.g., CD8+ T cells) or T helper cell (e.g., CD4+ T cells). In one embodiment, the cell may comprise macrophages, including CD4+, CD3+, CD45+, CD8+, CD11b, or CD68.

As used herein, "macrophage" refers to a cell capable of phagocytosis. A macrophage is a relatively long-lived phagocytic cell of mammalian tissues, derived from blood monocytes, and may be static or mobile. Due to differences in receptor expression, cytokine production, and functions, a macrophage may be referred to as M1 or M2. In embodiments, M1 may refer to Type I macrophages; M2 may refer to Type II. M1 macrophages are cells capable of producing pro-inflammatory cytokines and are implicated in the killing of pathogens and tumor cells. M2 macrophages moderate the inflammatory response, eliminate cell wastes, and promote angiogenesis and tissue remodeling (e.g., repair). Non-limited examples of macrophages include adipose tissue macrophages, monocytes, Kupffer cells, sinus histiocytes, alveolar macrophages, tissue macrophages, Langerhans cells, microglia, Hofbauer cells, Intraglomerular mesangial cells, osteoclasts, epithelioid cells, red pulp macrophages, peritoneal macrophages, or Peryer's Patch macrophages. In embodiments the presence of M1 macrophages may be determined by measuring biomarkers for M1, for example CD38, G-protein coupled receptor 18 (Gpr18), Formyl peptide receptor 2 (Fpr2), or iNos. In embodiments the presence of M2 macrophages may be determined by measuring biomarkers for M2, for example Early growth response protein 2 (Egr2), c-Myc, or CD206.

In one embodiment, the biomarker may be pro-inflammatory markers associated with M1 macrophages including, but is not limited to, IL-1β and IL-6. In another embodiment, the biomarker may be pro-tumoral markers associated with M2 macrophages including, but are not limited to, IL-10, IL-13, and TGF-(β1.

Methods disclosed herein may be beneficial for treating an inflammatory disease. The expression level of a biomarker may be measured prior to and after administration of at least one polyacetylene compound disclosed herein. For instance, cytokine or regulatory T cell levels may be measured by any method well known in the art prior to and after administration of at least one compound disclosed herein.

In one embodiment, the expression level of a biomarker may be decreased by more than about 5%, 6%, 7%, 8%, 9%, 10%, 11%, 12%, 13%, 14%, 15%, 20%, 25%, 30%, 40%, 50%, 60%, 70%, 80%, 90%, 95%, or 100% compared to a controlled sample.

In one embodiment, the expression level of a biomarker may be increased by more than about 5%, 6%, 7%, 8%, 9%, 10%, 11%, 12%, 13%, 14%, 15%, 20%, 25%, 30%, 40%, 50%, 60%, 70%, 80%, 90%, 95%, or 100% compared to a controlled sample.

The preceding description is exemplary in nature and is not intended to limit the scope, applicability or configuration of the disclosure in any way. Various changes to the described embodiments may be made in the function and arrangement of the elements described herein without departing from the scope of the disclosure.

Unless defined otherwise, all technical and scientific terms used herein have the same meaning as commonly understood by one of ordinary skill in the art to which this invention is related.

As used in this application and in the claims, the singular forms "a", "an", and "the" include the plural forms unless the context clearly dictates otherwise. Additionally, the term "includes" means "comprises". The methods and compositions of the present disclosure, including components thereof, can comprise, consist of, or consist essentially of the essential elements and limitations of the embodiments described herein, as well as any additional or optional ingredients, components or limitations described herein or otherwise useful in biocidal compositions.

Unless otherwise indicated, all numbers expressing quantities of ingredients, properties such as molecular weight, percentages, and so forth, as used in the specification or claims are to be understood as being modified by the term "about". Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximate unless the word "about" is recited.

As used herein, "optional" or "optionally" means that the subsequently described material, event or circumstance may or may not be present or occur, and that the description includes instances where the material, event or circumstance is present or occurs and instances in which it does not. As used herein, "w/w %" and "wt %" mean by weight as relative to another component or a percentage of the total weight in the composition.

The term "about" is intended to mean approximately, in the region of, roughly, or around. When the term "about" is used in conjunction with a numerical range, it modifies that range by extending the boundaries above and below the numerical values set forth. Unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

The phrase "effective amount" means an amount of a compound that promotes, improves, stimulates, or encourages a response to the particular condition or disorder or the particular symptom of the condition or disorder.

Here and throughout the specification and claims, range limitations are combined and interchanged, such ranges are identified and include all the sub-ranges contained therein unless context or language indicates otherwise. For example, all ranges disclosed herein are inclusive of the endpoints, and the endpoints are independently combinable with each other.

This written description uses examples to disclose the present disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

Furthermore, certain aspects of the present disclosure may be better understood according to the following examples, which are intended to be non-limiting and exemplary in nature. Moreover, it will be understood that the compositions described in the examples may be substantially free of any substance not expressly described.

The present disclosure may be better understood with reference to the following examples.

EXAMPLES

Materials and Methods

Animals

Mice (C57BL/6) were housed 3-5/cage, maintained on a 12:12-h light-dark cycle in a low stress environment (22° C., 50% humidity, low noise), and given food and water ad libitum. All mice were fed an AIN-76A diet (Bioserv, Frenchtown, NJ, USA; catalog #:F1515), a purified, balanced diet that is phytoestrogen free. Dietary phytoestrogens have been shown to influence anxiety-related behaviors, fat deposition, blood insulin, leptin and thyroid levels as well as lipogenesis and lipolysis in adipocytes, all of which could nonspecifically impact tumorigenesis. Body weight, food, and water consumption were monitored on a weekly basis for the duration of the study.

AOM/DSS Mouse Model-CRC

Using the AOM/DSS protocol, CRC was chemically induced as illustrated in FIG. 1A. Briefly, a total of fifty 11-week-old C57BL/6 female (n=25) and male (n=25) mice were randomly divided into three different groups for each sex: cancer-free (n=5/sex; CF), AOM/DSS+Vehicle (n=10/sex; AOM/DSS+VEH), and AOM/DSS+Panaxynol (n=10/sex; AOM/DSS+PA). At 11-12 weeks of age (baseline week 0) mice received either a single intraperitoneal injection of the carcinogen AOM (10 mg/kg; Sigma) diluted in PBS or PBS alone (CF control). Mice that were administered AOM were subjected to three cycles of DSS-supplemented water (36-50 kDa; MP Biomedical) at final concentrations of 1.5%, 1%, and 1% at weeks 1, 4, 7, respectively. Each DSS cycle lasted for a 1-week period and was followed by 2-week period of regular drinking water. To allow for greater tumor development, mice were euthanized 5 weeks after the final DSS cycle.

DSS Mouse Model—Colitis

Figure 9A:
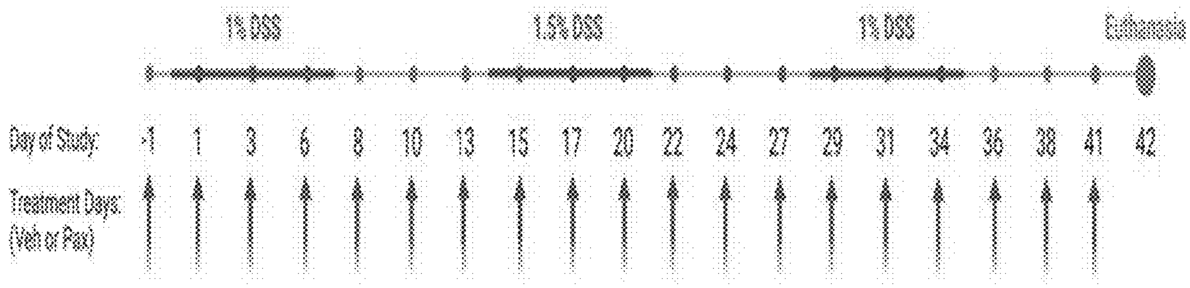
FIG. 9A illustrates schematic demonstrating experimental design, disease induction, and treatment administration for the chronic colitis model.
Figure 9E:
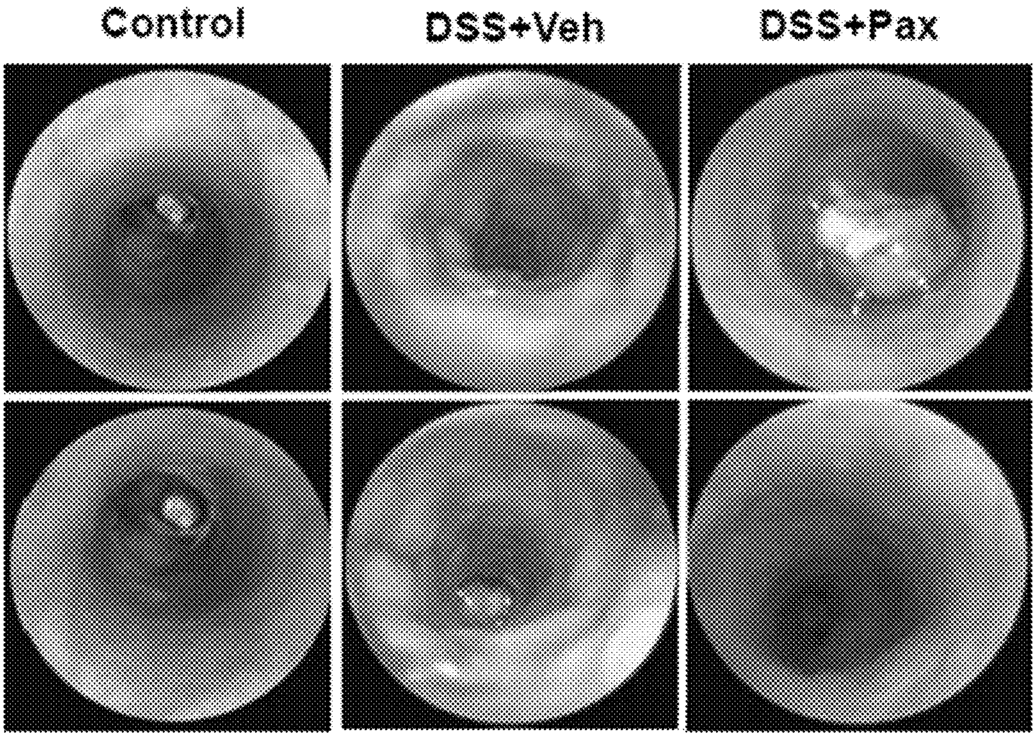
FIG. 9E illustrates representative images from end-of-study endoscopies.

To provide a more comprehensive study of colitis, two murine colitis models were utilized:

Experiment 1—Chronic Colitis: 14-week-old C57BL/6 female mice were given 3 cycles of DSS. Each cycle consisted of 7 days on DSS (cycle 1: 1%; cycle 2: 1.5%, cycle 3: 1%), immediately followed by 7 days of regular drinking water. Either vehicle or panaxynol was administered 3×/week beginning on the day prior to the first DSS cycle (day −1) until study completion (FIG. 9A). To ensure the induction of colitis and to quantify disease states, colitis symptoms were monitored 3×/week using a pre-established disease activity index (DAI), which quantifies bodyweight loss, stool consistency, and rectal bleeding to produce an overall symptom score; a higher score correlates with worsened disease. Mice were euthanized on day 42—one day after the last dose of panaxynol was given. Data presented in FIG. 9A-9F was obtained from 2 cohorts of Experiment 1—Chronic Colitis.

Figure 10A:
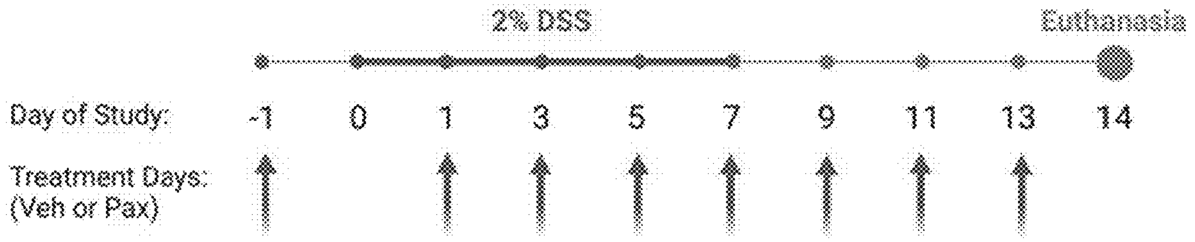
FIG. 10A illustrates schematic demonstrating experimental design, disease induction, and treatment administration for the acute colitis model.

Experiment 2—Acute Colitis: 14-week-old C57BL/6 female mice were given 1 cycle of 2% DSS in drinking water for 7 days, immediately followed by 7 days of regular drinking water. Either vehicle or panaxynol was administered 3×/week beginning on the day prior to the first DSS cycle (day −1) until study completion (FIG. 10A). To ensure the induction of colitis and to quantify disease states, colitis symptoms were monitored every other day using the same DAI as above. Mice were euthanized on day 14—one day after the last dose of panaxynol was given. Colons were placed in the appropriate buffers for further analysis. Data presented in FIGS. 10-14 (i.e., histology, immunofluorescence, electron microscopy, and flow cytometry) was obtained using colonic tissue from 2 cohorts of Experiment 2—Acute Colitis.

Panaxynol Preparation

Panaxynol (PA; $C_{17}H_{24}O$) was purchased from Biopurify Pytochemicals Ltd in sealed 5 mg/mL vials in pure 95% ethanol and stored at −20° C. PA was prepared fresh on the day of treatment by diluting in $H_2O$ to 1 mg/mL for administration (p.o.) at a dosage of 2.5 mg/kg. This dosage was chosen following a pilot dose-response study to determine PA's efficacy. PA or VEH was administered 3×/week via oral gavage using flexible plastic tubing gavage needles (Instech, Cat #FTP-20) for a total of 12 weeks.

Symptom Monitoring and Scoring

All mice underwent the same symptom monitoring and scoring. Body weights and symptom scores were determined 1×/week to quantify disease state, with a higher score indicative of a worsened disease state. Symptom scores were calculated by scoring percent body weight loss, stool consistency, and rectal bleeding as previously described. Briefly, fresh colonic evacuates were smeared onto "Hemoccult" tape (Beckman Coulter) to assess severity of diarrhea and were tested with developer (Beckman Coulter) to assess rectal bleeding. Stool consistency was scored as follows: solid cylinder (0), soft cylinder and easily spreadable (2), and noncylindrical or runny (4). Bleeding was scored as follows: no positive detection of blood (0), detection of blood but not grossly visible (2), and gross visibility of blood (4). Body weight was calculated as percent body-weight loss: 0%-5% (0), 6%-10% (1), 11%-15% (2), 15%-20% (3), 20%-25% (4), and >25% (5). Scores of all three categories were summed to obtain an overall symptom score for each mouse.

Colonoscopies

Prior to euthanasia, colonoscopies were performed (n=3/group) to visualize the colonic tissue and quantify the severity of disease (colitis and colorectal tumors) using an established protocol. Briefly, mice were anesthetized with isoflurane to perform a detailed endoscopic examination in which the endoscope was gently inserted into the rectum and through the anus. Air was applied to slowly set apart the intestinal walls for examination. As the scope advanced, pictures were taken frequently and the following were meticulously assessed and scored by the blinded primary investigator using the well-established scoring system to integrate evaluation of intestinal inflammation (i.e., focal lesions (edematous areas of mucosa, erosions/reddened areas, ulcers), perianal region findings (diarrhea, bloody anal discharge, or prolapse), transparency of the colonic wall (visualization of the intramural blood vessels), and presence of intestinal bleeding) and tumors. Scoring was performed as previously described with no modifications. Upon completion of colonoscopies, mice were placed on a warm pad set at 37° C. for 5 min.

Tissue Collection

Following 12 weeks of PA treatment, mice were euthanized by isoflurane overdose following a 4 hr fast. Retro-orbital blood was collected for blood analysis. The colon was excised and carefully flushed with PBS to remove fecal material, cut longitudinally, and opened to be imaged on a dissection microscope in which all tumors were counted and measured based on size as follows: small (≤1 mm), medium (1-2 mm), and large (>2 mm). Following imaging, the colons in the first cohort of animals (n=5-6/group) were cut in half in which the proximal portion was snap frozen in liquid nitrogen for RT-qPCR gene expression analysis and the distal portion swiss rolled, fixed in 10% formalin, and paraffin embedded for histopathology, immunohistochemistry, and immunofluorescence. Colons from a separate cohort (n=5-8/group) were placed in ice-cold PBS until flow cytometry. In a third cohort, tumors were excised from the entire colon and snap frozen for RT-qPCR (n=4-5/group). The colon (without tumors; n=5-7/group) was then placed in ice-cold PBS until flow cytometry.

Blood Panel Analysis

A blood panel analysis was performed (n=14-17/group for AOM/DSS groups and n=10 for CF group) using the VetScan HMT (Abaxis) for determination of total white blood cells (WBC), lymphocytes (LYM), monocytes (MON), and neutrophils (NEU). The neutrophil to lymphocyte ratio (NLR) was calculated from obtained values.

Lamina Propria Isolation

Lamina propria (LP) cells were isolated from colons to be used for flow cytometry to identify immune cell populations within the colonic LP. Colons were rinsed in sterile ice-cold PBS and minced with scissors. Tissues were subjected to a cell dissociation solution (HBSS without $Ca^{2+}Mg^{2+}$ containing 5 mM EDTA and 1 mM DTT) in a shaking incubator for 30 min at 37° C. Tubes containing dissociated tissues were vortexed and passed through a 100 μm cell strainer; flow through containing intestinal epithelial cells (IECs) was discarded. Remaining tissue was subjected to a cell digestion buffer (HBSS with $Ca^{2+}Mg^{2+}$ containing 5% FBS, 5 mg/mL Collagenase D, 50 μg/mL DNase 1, and 1 U/mL Dispase) in a shaking incubator for 30 min at 37° C. Tubes were vortexed and passed through a 40 μm cell strainer. Ice-cold PBS was added to filter to collect remaining cells. Tubes were spun at 2500 rpm for 15 min to pellet. Cells were passed through a Percoll gradient (40/80% (v/v) gradient) and spun at 2500 rpm for 20 min without acceleration and brakes. Cells at the 40/80 interface (leukocytes) were collected, spun at 2000 rpm at 4° C. for 10 min, washed with PBS, and prepared for flow cytometry analysis.

Flow Cytometry

To identify macrophages, colonic LP cells were isolated as described above and first incubated with ZombieGreen (FITC; Bio-Rad) solution for 20 min at RT in dark to discriminate Live/Dead (n=5-8/group). Cells were then washed with flow buffer (HBSS without $Ca^{2+}Mg^{2+}$ containing 0.5% FBS, 10 mM HEPES (Gibco), and 2 mM EDTA (Gibco)), blocked for non-specific binding with FC block for 10 min at 4° C., and then incubated with fluorescently labelled antibodies (BioLegend) against macrophage cell-surface markers: CD45, CD11b, and CD68 for 20 min at 4° C., followed by 2 PBS washes, with the final resuspension in flow buffer. Colonic LP cells were gated for non-debris singlets and considered live immune cells with ZombieGreen$^{Neg/Low}$ and CD45$^{+}$. From the Live CD45$^{+}$ population, CD11b$^{+}$CD68$^{+}$ cells were identified as macrophages.

To identify neutrophils, colonic LP cells were isolated as described above and incubated with ZombieGreen (FITC; Bio-Rad) solution for 20 min at RT in dark to discriminate Live/Dead (n=2-3/group). Cells were then washed with flow buffer and blocked for non-specific binding with FC block for 10 min at 4° C., and then incubated with fluorescently labelled antibodies (BioLegend) against neutrophil cell-surface markers: CD45, CD11b, and Ly6g.

To identify T-cell phenotypes, colonic LP cells were isolated as described above and incubated in 0.02% Brefeldin A in complete media (cDMEM) for 4 hr (n=5-7/group). Cells were stained with fluorescently labelled antibodies against T-cell surface markers: CD45, CD4, and TCRβ. 1× fix was used to fix the cell surface stains, and 1× perm buffer was used to permeabilize cell membranes (BioLegend; Cat #424401). Cells were then stained with fluorescently labelled antibodies against intracellular marker FoxP3 to identify regulatory T-cells (T-regs). All cells were measured using a FACS Aria II (BD) and analyzed using FlowJo (BD Biosciences).

Real-time Quantitative PCR

Proximal colons (n=5-7/group) and colonic tumors (n=4-5/group) were homogenized and RNA was extracted. RNA sample quality and quantities were verified using a Nanodrop One Microvolume UV-Vis Spectrophotometer (Thermo Fisher Scientific) and determined to be of good quality based on A260/A280 and 260/230 values (>1.8) prior to cDNA synthesis using High-capacity Reverse Transcriptase kit (Applied Biosystems, Cat #4368814). Quantitative reverse transcriptase polymerase chain reaction (PCR) analysis was carried out as per the manufacturer's instructions and all primers used were TaqMan Gene Expression Assays (Applied Biosystems). TaqMan reverse transcription reagents were used to reverse transcribe and to analyze colon and tumor mRNA gene expression of the following markers: monocyte/macrophage (CD68, MRC1 (colon only), and MSR1 (colon only)), pro-inflammatory M1 macrophage markers (IL-1β (colon only) and IL-6), anti-inflammatory M2 macrophage markers (IL-10 (colon only), IL-13, and TGF-(β1), neutrophils (Ly6G), T-regs (Foxp3), pro-apoptotic Bc1-2-associated X-protein (Bax), genes associated with intestinal barrier integrity and function (occludin (OCLN), tight junction 3 (TJP3), mucin 1 (Muc1), and Muc2) was performed. Briefly, quantitative RT-PCR analysis was carried out as per the manufacturer's instructions (Applied Biosystems) using Taq-Man Gene Expression Assays on a Qiagen Rotor-Gene Q. Data were normalized to controls and compared to five reference targets (Hmbs, B2M, TBP, H2afv, and 18s), which were evaluated for expression stability using GeNorm.

Immunohistochemistry

To examine cell proliferation, immunohistochemical analysis of Ki67 (Abcam, #ab16667) was performed. Color was developed with DAB (Vector Laboratories, #SK-4100) for 6 min at RT and counterstained using CAT hematoxylin and Tacha's bluing for 30 secs. Representative images were taken at x20 using Keyence All-in-One fluorescence Microscope BZ-X800. Percentage of Ki67 cells (DAB-positive nuclei) over total cells, relative to area, were quantified using Material Image Processing and Automated Reconstruction (MIPAR) software. Five images were assessed for each mouse (n=3/group). TUNEL staining was carried out using ApopTag Peroxidase In Situ Apoptosis Detection Kit (Millipore, #S7100). Color was developed with DAB (Vector Laboratories, #SK-4100) for 6 min at RT and counterstained using 1% methyl green (R&D systems, #4800-30-18) for 10 min at RT. Representative images were taken at ×20 using Keyence All-in-One fluorescence Microscope BZ-X800. Percentage of apoptotic cells (TUNEL-positive nuclei) over total cells, relative to area, were quantified using Material Image Processing and Automated Reconstruction (MIPAR) software. Five images were assessed for each mouse (n=3/group).

Immunofluorescence

Immunofluorescence of tumors within colon tissues (n=3/group) was performed. Briefly, sections were incubated with rodent decloaker (Biocare Medical, Cat #RD913M) for 30 min at 95° C. for antigen retrieval, 10% goat serum in 5% BSA/TB S for 1 hr at RT to block non-specific binding, and rat anti-mouse FitC-conjugated F4/80 antibody (BioRad; Cat #MCA497F) in 5% BSA/TBS overnight at 4° C. Sections were then washed with TBS, counterstained with 4',6-diamidino-2-phenylindole (DAPI, 1 μg/ml), washed with water, and mounted with a glycerol based mounting media. Representative fluorescent images were taken at χ20 using Echo Revolution microscope.

Histopathology

The distal portion of colon was swiss rolled and fixed overnight in 10% formalin, dehydrated with alcohol, and embedded in paraffin wax. Paraffin sections were stained with hematoxylin and eosin (H&E; Fisher HealthCare) and stained separately for goblet cells with Alcian Blue (AB; Newcomer Supply; Cat #9102A) (n=3/group).

Cell Culture

Bone marrow-derived macrophages (BMDMs) were isolated from healthy 10-14-week-old C57BL/6 male mice. Briefly, mice were euthanized by isoflurane overdose. Femurs were cleared of muscle and debris. The epiphyses of the femurs were cut and placed knee-down and spun down in a 1.5 mL tube. Bone marrow was collected and resuspended in complete DMEM (cDMEM; 10% FBS, 1% penicillin/streptomycin) and passed through two 100 μm strainers. Cells were plated on an untreated 10 cm dish in cDMEM and allowed to incubate at 37° C. for 4 hr. Adherent/mature monocytes and dendritic cells were discarded, while floating/immature monocytes were collected. Cells were subjected to RBC lysis and resuspended in bone marrow maintenance media (BMMM; 20% L929-conditioned media in cDMEM). Cells were then plated on surface-treated 6-well plates at a 250 k cells/well seeding density. On day 3, fresh BMMM was added. On day 5, media was aspirated and fresh BMMM was added. For M2 macrophage polarization experiments, 6-day mature macrophages were given either cDMEM+VEH, M2 media (cDMEM with 10 ng/mL IL-4)+VEH, or M2 media+1 μM PA. Cells were incubated for 24 hr. For C26 colon tumor conditioned media (C26 CM) experiments, 6-day mature macrophages were given either serum-free media (SFM)+VEH, 33% C26-conditioned media (C26 CM)+VEH, or 33% C26 CM+1, 2.5, or 5 μM PA. Cells were incubated for 48 hr. After incubation with these different treatments, cells were washed twice with PBS and incubated with 5 mM EDTA PBS at 4° C. for 20 min. Cells were then gently scraped and transferred into flow tubes, spun at 1600 rpm at 4° C. for 5 min, and washed in PBS before antibody staining. Cells were stained and analyzed for macrophages via flow cytometry as described above with the addition of analyzing macrophage phenotypes. From the $CD11b^+CD68^+$ macrophage population, macrophage phenotypes were determined based on CD206 and CD11c expression. $CD206^-CD11c^-$ cells were identified as M0 macrophages; $CD206^-CD11c^+$ as M1 macrophages; $CD206^+CD11c^-$ cells as M2 macrophages; $CD206^+CD11c^+$ as M1-M2 transitional macrophages. All cells were measured using a FACS Aria II (BD) and analyzed using FlowJo (BD Biosciences). Three independent experiments were carried out for each in vitro assessment.

Cell Counting Kit-8 (CCK-8)

BMDMs were isolated as described above. On day 6 of maturation, BMDMs were subjected to 7 concentrations of PA to assess cell death: 0.001, 0.01, 0.1, 1.0, 5.0, 10.0, and 100.0 μM. On day 7 (i.e., 24 hr-post PA treatment), CCK-8 (Dojindo; Cat #CK04) assays were completed per manufacturer's instructions. C26 CRC cells were also subjected to these 7 concentrations of PA for 24 hr to assess cell death using CCK-8. Three independent experiments were carried out.

Statistical Analyses

All data was analyzed using commercial software (GraphPad Software, Prism 7, La Jolla, CA, USA). All in vivo outcomes were analyzed using a paired or unpaired Student's t-test, one-way ANOVA, or two-way ANOVA where appropriate. If a significant difference was observed for a one-way ANOVA, a Tukey's multiple comparisons test was performed to further define group differences. If a significant difference was observed for a two-way ANOVA, a Bonferroni's or Benjamini, Krieger, and Yekutieli multiple comparisons test was performed to further define group differences. Survival curve analysis was conducted by log-rank (Mantel-Cox) test. All gene expression analyses were analyzed using a Student's t-test. Statistical significance was set at $p<0.05$. Data are presented as mean±standard error of mean (SEM). All figures were generated using GraphPad Prism.

Results

Panaxynol Improves Clinical Symptoms and Reduces Inflammation in CRC

Figure 1B:
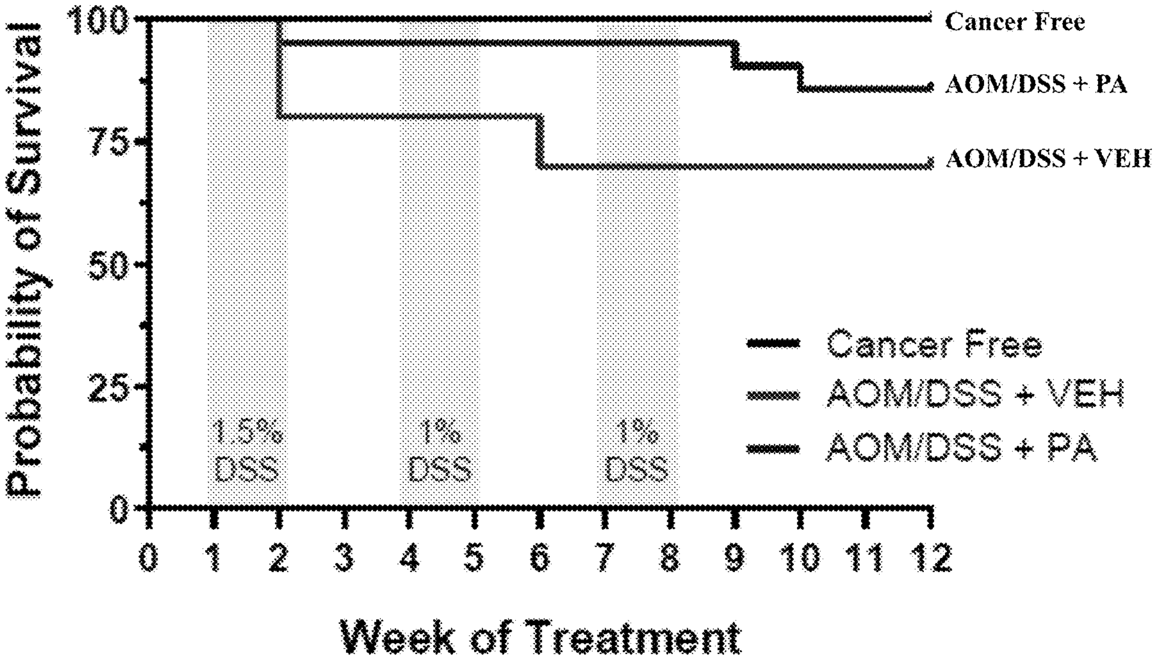
FIG. 1B illustrates probability of survival of AOM/DSS-induced CRC using 11-week-old C57BL/6 female (n=20) and male (n=20) mice over 12 weeks.
Figure 1C:
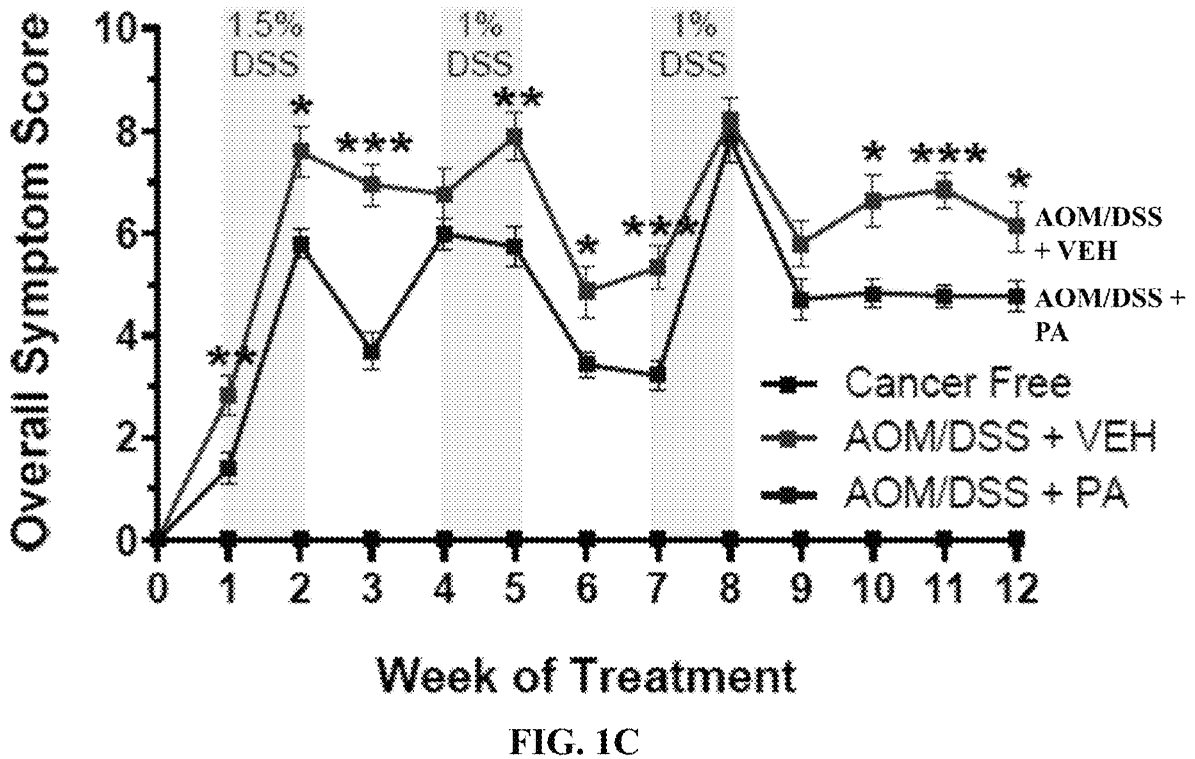
FIG. 1C illustrates overall symptom score accounting for percent body weight loss, stool consistency, and rectal bleeding. Significance was determined by multiple paired Student's t-tests between AOM/DSS treated mice. For all data herein: *$p \leq 0.05$; $p \leq 0.005$; and *$p \leq 0.0005$.
Figure 1D:
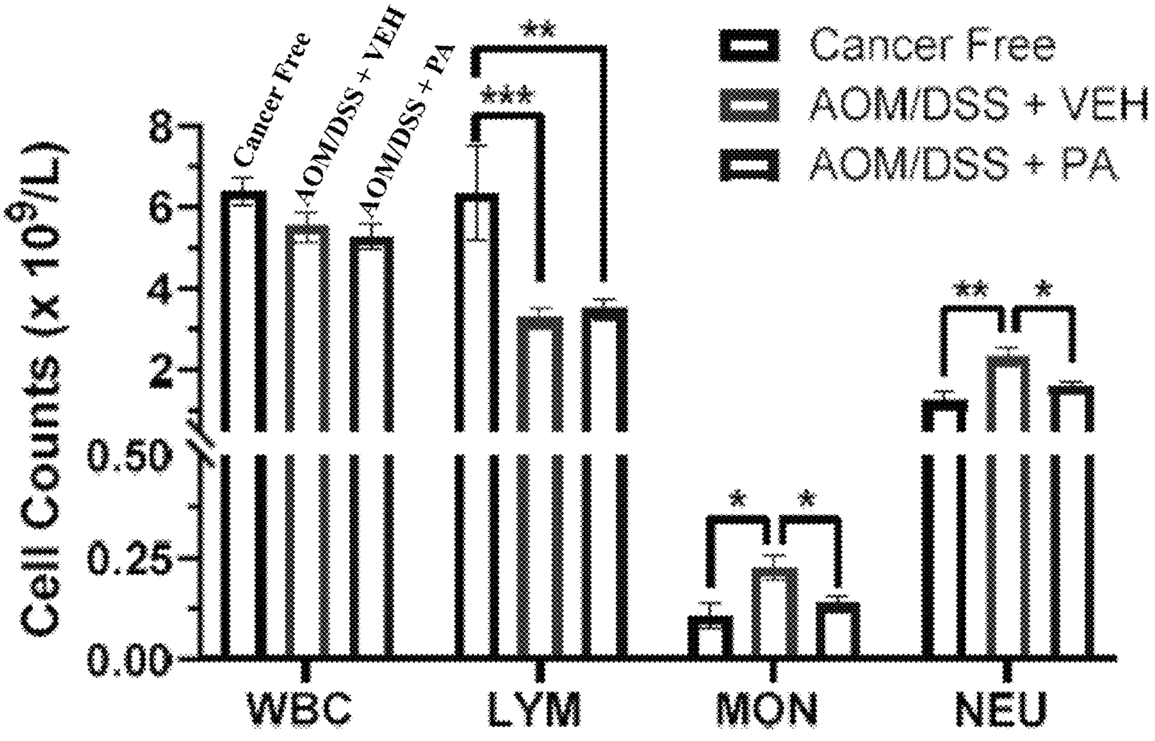
FIG. 1D illustrates circulating white blood cells (WBCs), lymphocytes (LYM), monocytes (MON), and neutrophils (NEU) determined in whole blood using VetScan HM5. Significance determined using ordinary one-way ANOVAs with Tukey multiple comparison test.
Figure 1E:
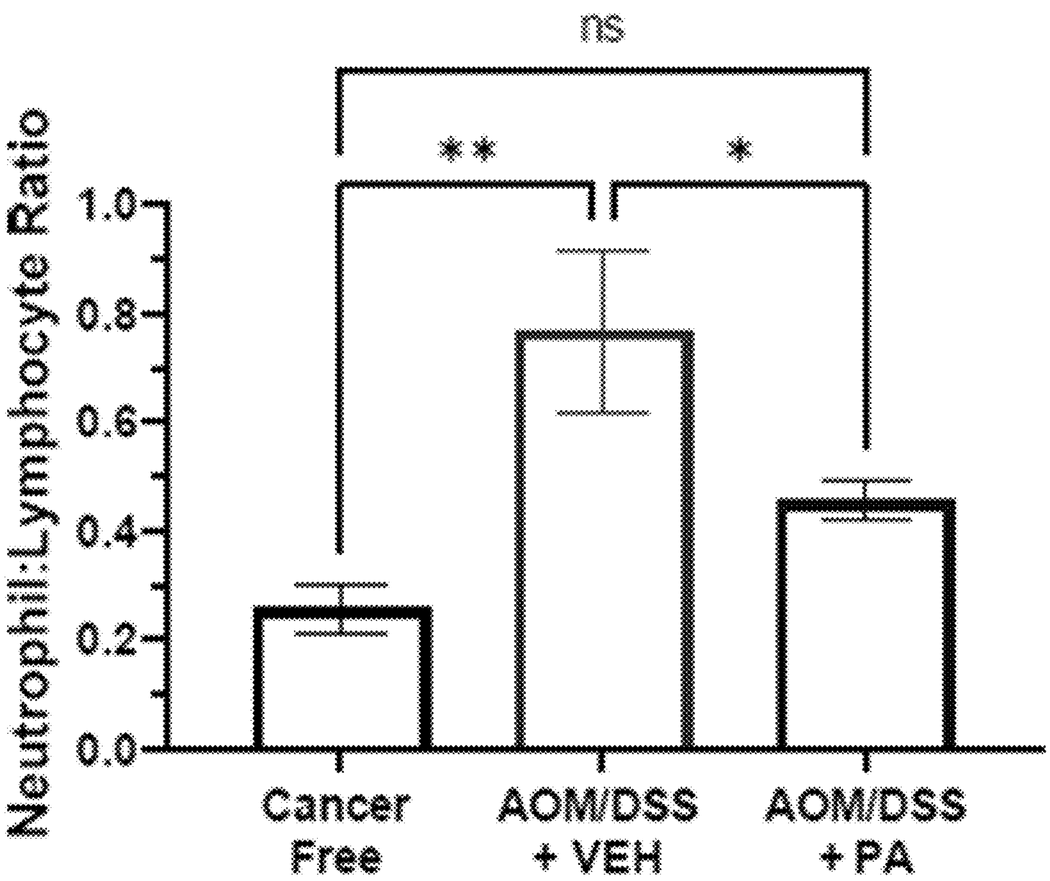
FIG. 1E illustrates neutrophil to lymphocyte ratio determined in whole blood. Significance determined using one-way ANOVA with Tukey multiple comparison test.

The experimental design is presented in FIG. 1A in which AOM/DSS was used to chemically-induce CRC. Over the course of 12 weeks of treatment, PA appears to improve survival, although non-significant (FIG. 1B; n=20/group for AOM/DSS groups and n=10 for CF). This was consistent with improved overall symptom scores with PA, which accounts for bodyweight loss, stool consistency, and rectal bleeding ($p<0.05$; FIG. 1C) (n=20/group for AOM/DSS groups and n=10 for CF). Specifically, PA significantly suppressed overall symptoms scores at weeks 1-3, 5-7, and 10-12 (*$p\leq0.05$, $p\leq0.005$, *$p\leq0.0005$; FIG. 1C). A comprehensive blood analysis was performed at the end of the study (FIG. 1D) (n=14-17/group for AOM/DSS groups and n=10 for CF). As expected, circulating monocytes (precursors of macrophages) were significantly increased in VEH-treated AOM/DSS mice compared to CF ($p<0.05$; FIG. 1D) and this was rescued by PA ($p\leq0.05$; FIG. 1D). Similarly, PA was able to ameliorate the significant increase in neutrophils, important promoters of tumor initiation, evasion, and maintenance in CRC [36] with VEH ($p\leq0.05$; FIG. 1D). This was consistent with a PA-induced decrease in the neutrophil to lymphocyte ratio (NLR) ($p\leq0.05$; FIG. 1E), an important prognostic factor for CRC [37]. There was no change in total WBCs across groups and while there was a decrease in lymphocytes with AOM/DSS ($p\leq0.05$; FIG. 1D), there was no difference between VEH- and PA-treated groups.

Panaxynol Suppresses AOM/DSS-Induced CRC

Figure 2A:
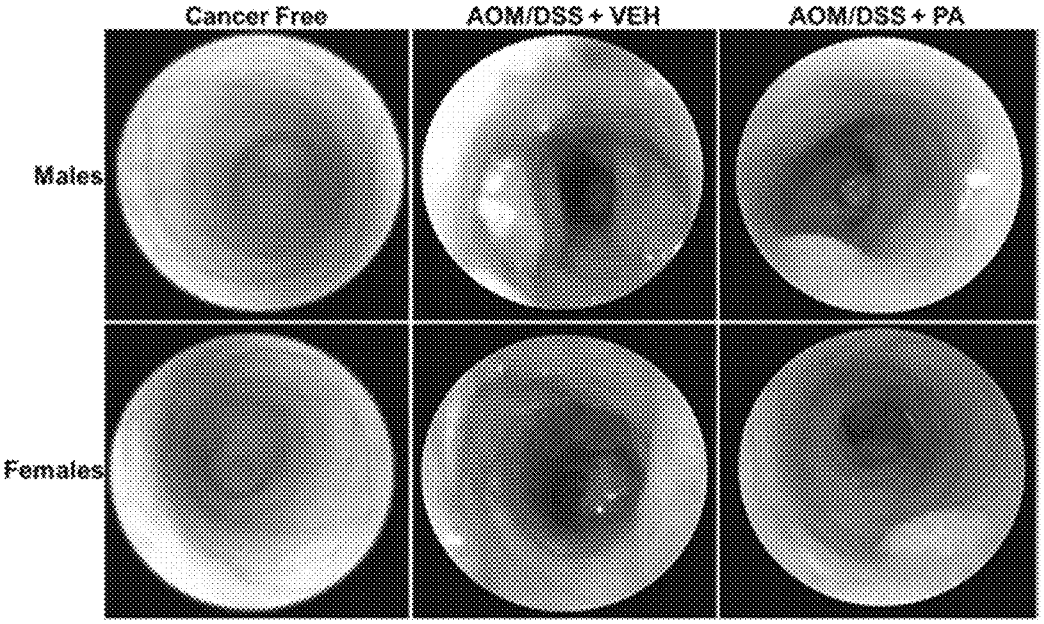
FIG. 2A illustrates representative colonoscopy images. C57BL/6 cancer free (n=10), AOM/DSS+VEH (n=14), AOM/DSS+PA (n=17) mice after 12 weeks of treatment.
Figure 2B:
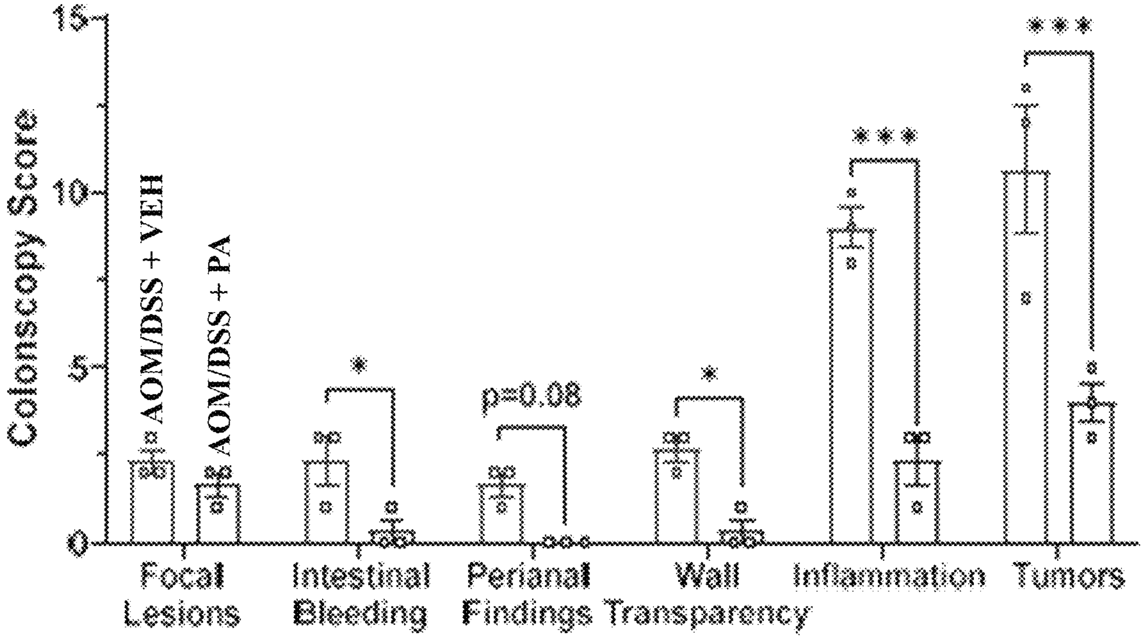
FIG. 2B illustrates colonoscopy scores (n=3/group). Significance was determined using an ordinary two-way ANOVA with Benjamini, Krieger, and Yekutieli multiple comparisons test.

After 12 weeks of treatment, colonoscopies were performed in a subset of mice (n=3/group) to visualize (FIG. 2A) and quantify disease severity (FIG. 2B) using a pre-established protocol to score for inflammation (i.e., focal lesions, intestinal bleeding, perianal findings, and wall transparency and) and tumors. As expected, colonoscopies of CF mice exhibited normal colonic architecture with visible small and large blood vessels (FIG. 2A). These blood vessels were less apparent and more so characterized by a thickened appearance of mucosa in VEH-treated AOM/DSS mice, which did not appear as severe for those treated with PA (FIG. 2A). This was supported by a significant reduction (i.e., improvement) in the transparency of the colonic wall, which accounts for the presence of intramural small and large blood vessels, in PA-treated AOM/DSS mice compared to that of VEH ($p\leq0.05$; FIG. 2B). In further support for PA's beneficial effects on CRC clinical manifestations, PA-treated AOM/DSS mice exhibited significant reductions in intestinal bleeding ($p\leq0.05$) and inflammation ($p\leq0.05$) compared to VEH-treated AOM/DSS mice; however, no significant difference in focal lesions or perianal findings ($p=0.08$) were detected (FIG. 2B). Further, several small and large protruding tumors were observed in VEH-treated AOM/DSS mice, while fewer and smaller tumors were observed in those treated with PA (FIG. 2A). This difference was accounted for in the tumor score which was significantly reduced by PA compared to VEH-treated AOM/DSS mice ($p\leq0.05$; FIG. 2B).

Figure 2C:
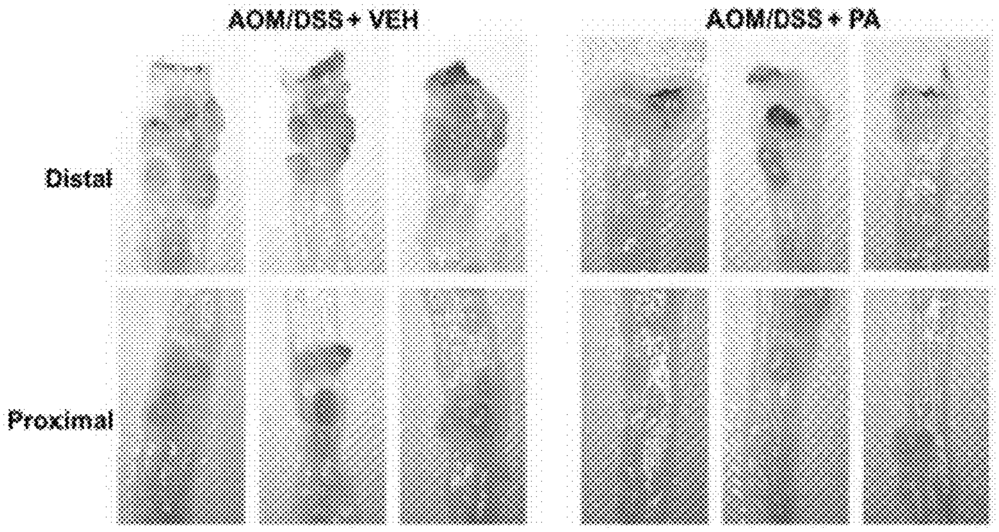
FIG. 2C illustrates representative images of tumors in the distal (top) and proximal (bottom) portion of colons using a dissection microscope.
Figure 2D:
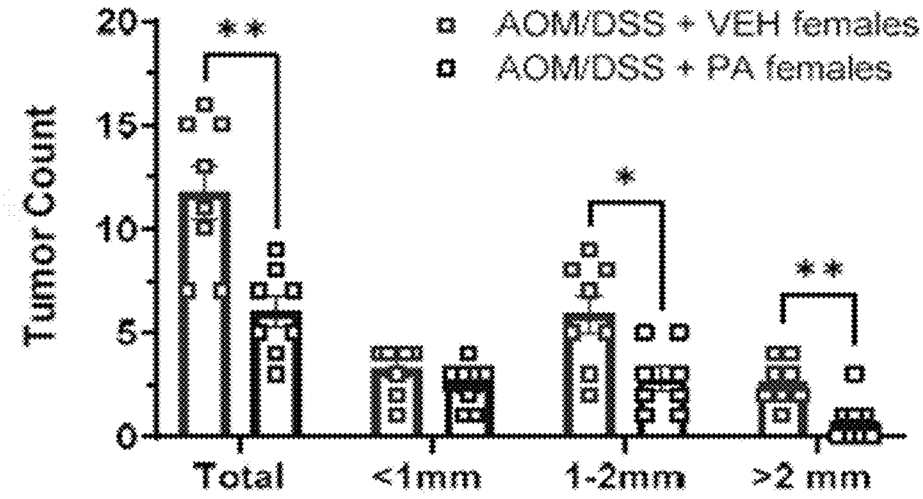
FIG. 2D illustrates tumor count of total, small (≤1 mm), medium (1-2 mm), and large (>2 mm) tumors in AOM/DSS+VEH or AOM/DSS+PA female mice.
Figure 2E:
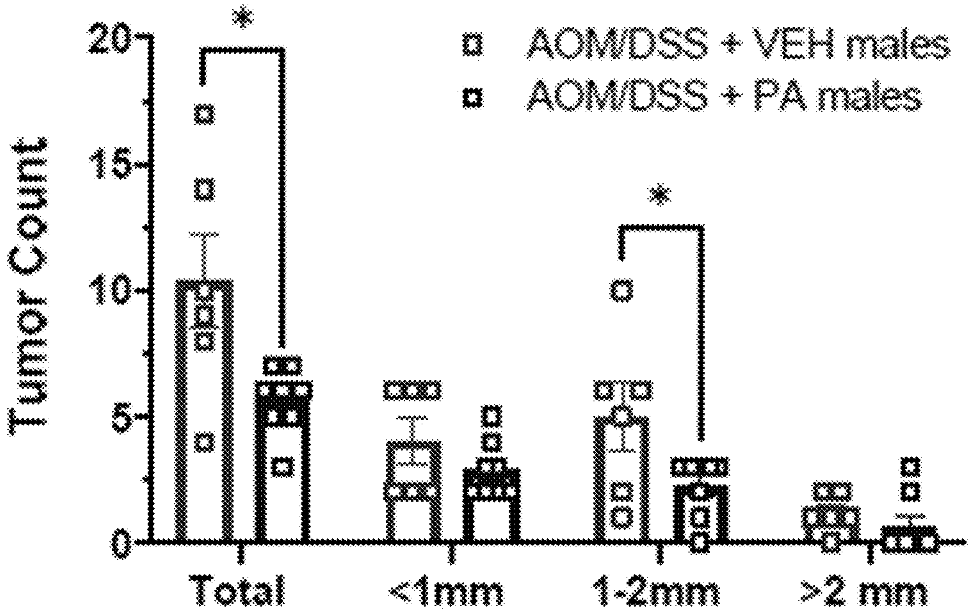
FIG. 2E illustrates tumor count of total, small (≤1 mm), medium (1-2 mm), and large (>2 mm) tumors in AOM/DSS+VEH or AOM/DSS+PA male mice.
Figure 2F:
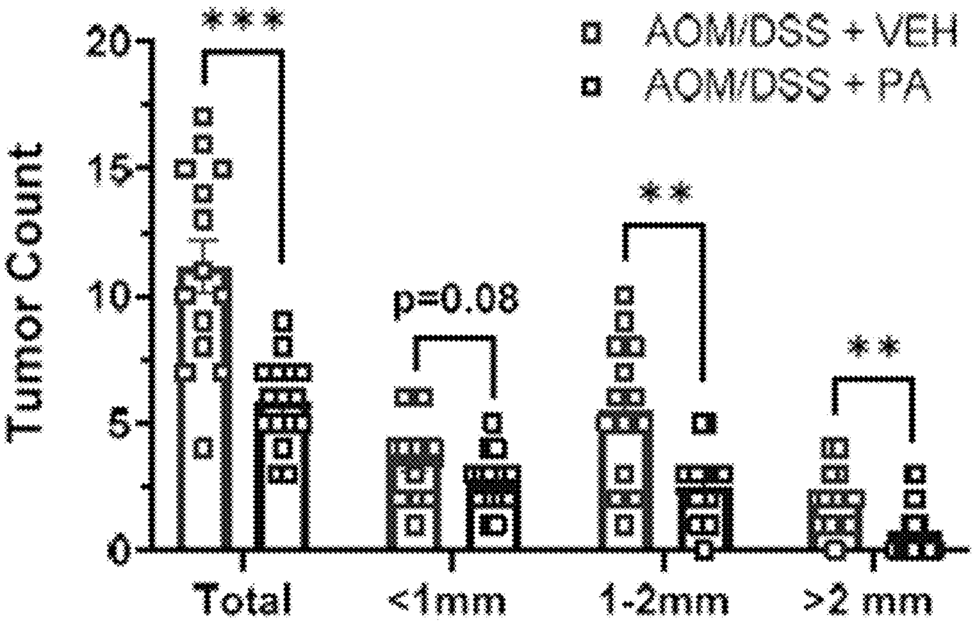
FIG. 2F illustrates tumor count of total, small (≤1 mm), medium (1-2 mm), and large (>2 mm) tumors in AOM/DSS+VEH or AOM/DSS+PA combined sexes.

After colonoscopies, mice (n=14-17/group for AOM/DSS groups) were euthanized and colon was excised, imaged, and tumors counted. Representative images of tumors in the distal and proximal colon were taken and tumors were counted using a dissection microscope (FIG. 2C). Compared to VEH, PA-treated AOM/DSS mice exhibited significant reductions in both the number and size of tumors in females ($p \leq 0.05$; FIG. 2D), males ($p \leq 0.05$; FIG. 2E), and sexes combined ($p \leq 0.05$; FIG. 2F). More specifically, PA significantly reduced total number of tumors and number of medium sized tumors (1-2 mm) in females, males, and sexes combined ($p \leq 0.05$; FIGS. 2D-2F). A significant reduction in large tumors (>2 mm) was exhibited in PA-treated females and sexes combined ($p \leq 0.05$; FIGS. 2D and 2F), but not in males alone. A reduction in small tumors (≤1 mm) was also observed in PA-treated AOM/DSS mice when sexes were combined but this did not reach statistical significance ($p=0.08$; FIG. 2D-2F). Given that PA appeared to benefit both sexes, data from females and males were combined in all further analyses.

Panaxynol Increases Apoptosis and Reduces Cell Proliferation in Colonic Tumors

Figure 3A:
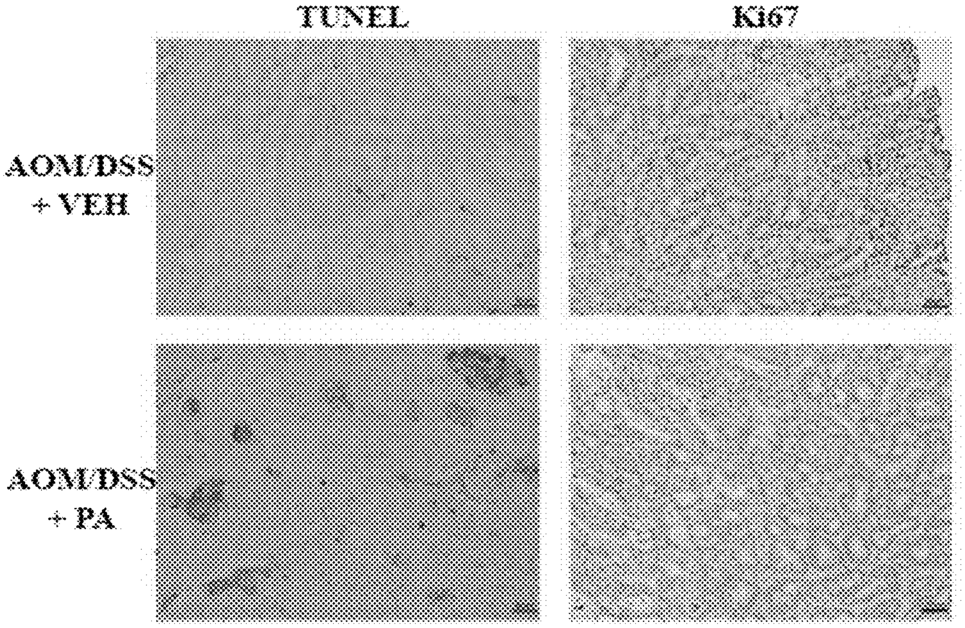
FIG. 3A illustrates immunohistochemistry of colonic tumors from AOM/DSS+VEH and AOM/DSS+PA mice (n=3/group) stained with TUNEL for detection of apoptotic cells and Ki67 to examine proliferation. Representative 20× images of colonic tumors stained with TUNEL (left) and Ki67 (right). Scale bar=50 μm.
Figure 3B:
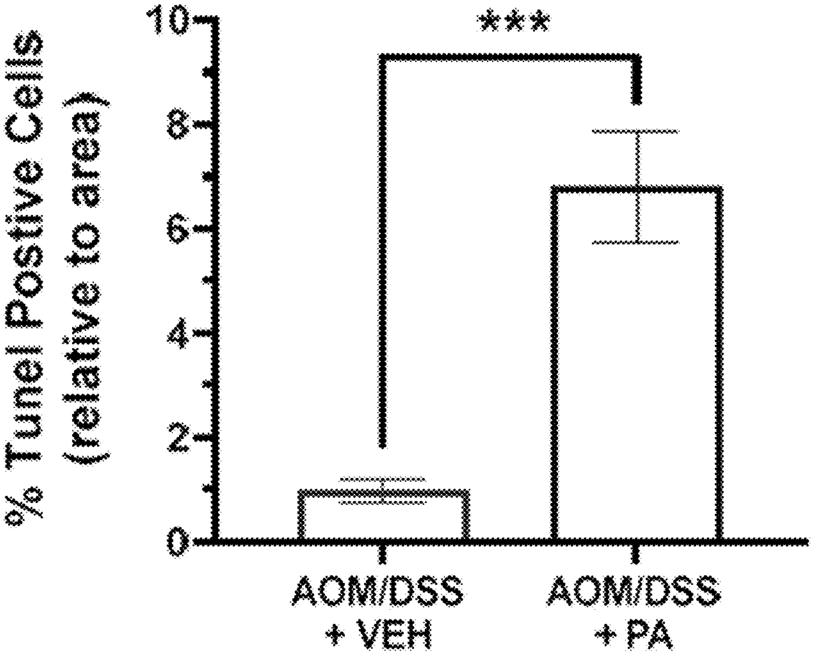
FIG. 3B illustrates percentage of apoptotic (positively stained TUNEL-DAB) cells relative to area (n=3/group).
Figure 3C:
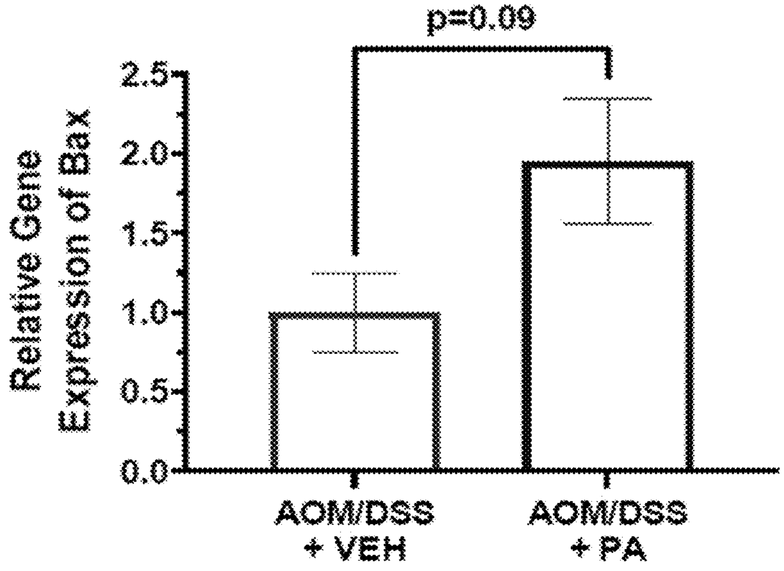
FIG. 3C illustrates gene expression analysis of Bax, a pro-apoptotic marker, within colonic tumors using qRT-PCR (n=5/group). Data were normalized to AOM/DSS+VEH and compared with five reference targets (B2M, TBP, HPRT, HMBS, and H2AFV) which were evaluated for expression stability using GeNorm.
Figure 3D:
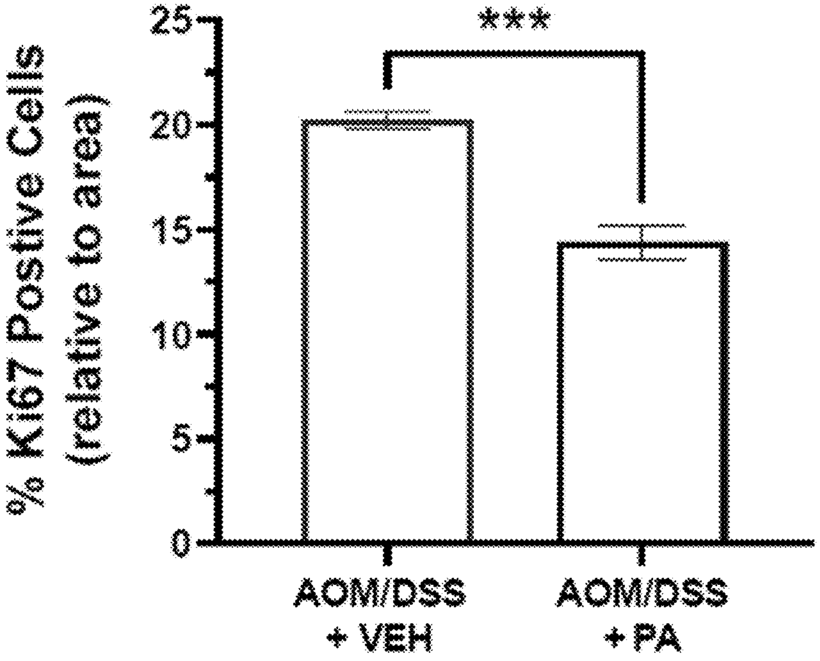
FIG. 3D illustrates percentage of Ki67 positive cells (positively stained Ki67-DAB) cells relative to area (n=3/group).

Given the reduction in tumor number and size with PA, its effects on apoptosis and proliferation in colonic tumors (n=3/group) was evaluated. Sections were stained with TUNEL for detection of apoptotic cells (FIG. 3A; left) and Ki67 to examine proliferation (FIG. 3A; right). In support of PA's anti-tumor effects, colonic tumors of PA-treated AOM/DSS mice exhibited a significant increase in the percentage of apoptotic cells compared to VEH ($p \leq 0.05$; FIG. 3B). Furthermore, gene expression of pro-apoptotic marker Bax was increased, although non-significant, in colonic tumors of PA-treated AOM/DSS mice (n=5/group) compared to that of VEH ($p=0.09$; FIG. 3C). In addition, PA reduced cell proliferation in colonic tumors, indicated by a significant decreased percentage of Ki67 positive cells compared to VEH ($p \leq 0.05$; FIG. 3D).

Panaxynol Rescues Intestinal Barrier Function

Figure 4A:
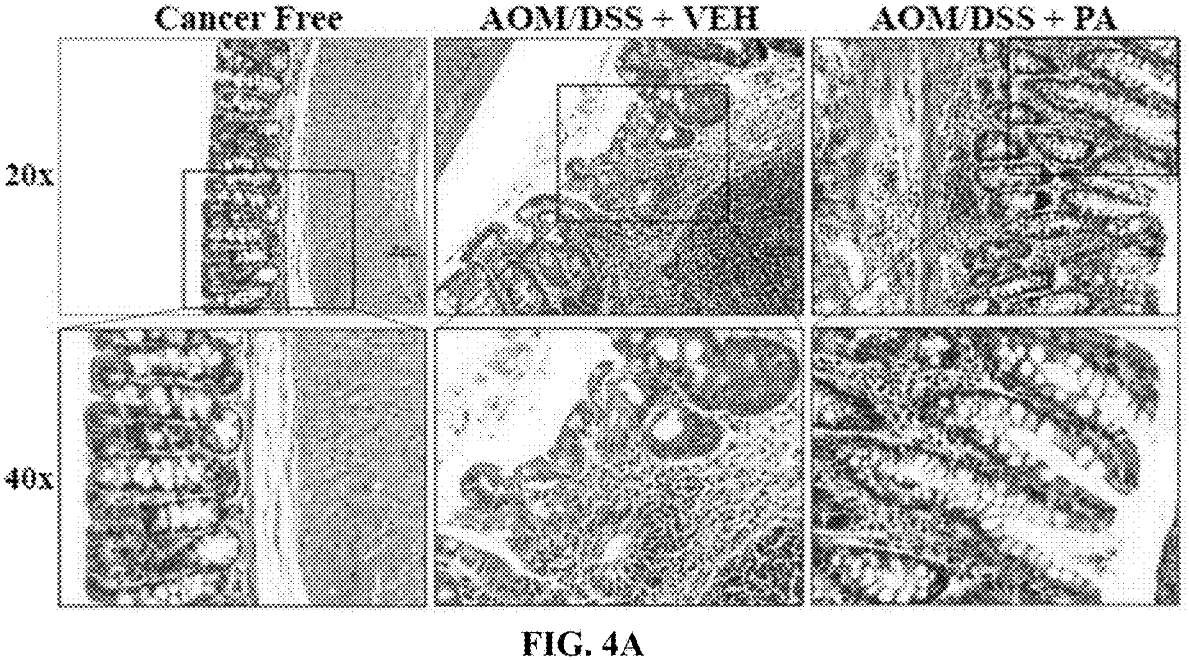
FIG. 4A illustrates C57BL/6 cancer free, AOM/DSS+VEH, AOM/DSS+PA mice after 12 weeks of treatment. Representative images of H&E stained distal colons.
Figure 4B:
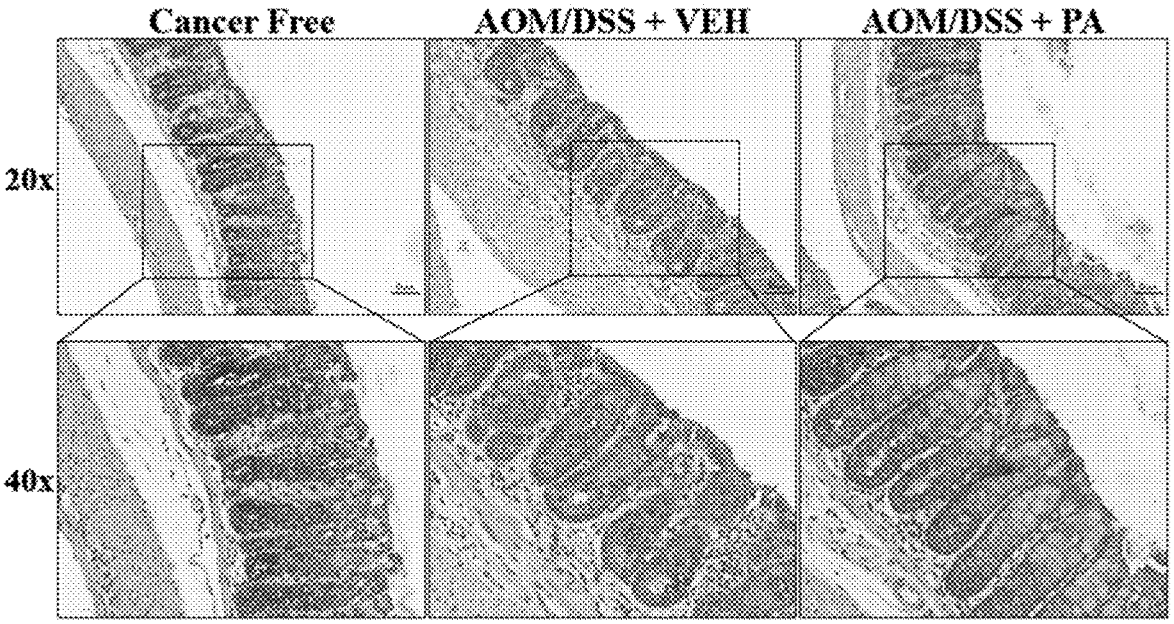
FIG. 4B illustrates C57BL/6 cancer free, AOM/DSS+VEH, AOM/DSS+PA mice after 12 weeks of treatment. Representative images of alcian blue stained distal colons.
Figure 4C:
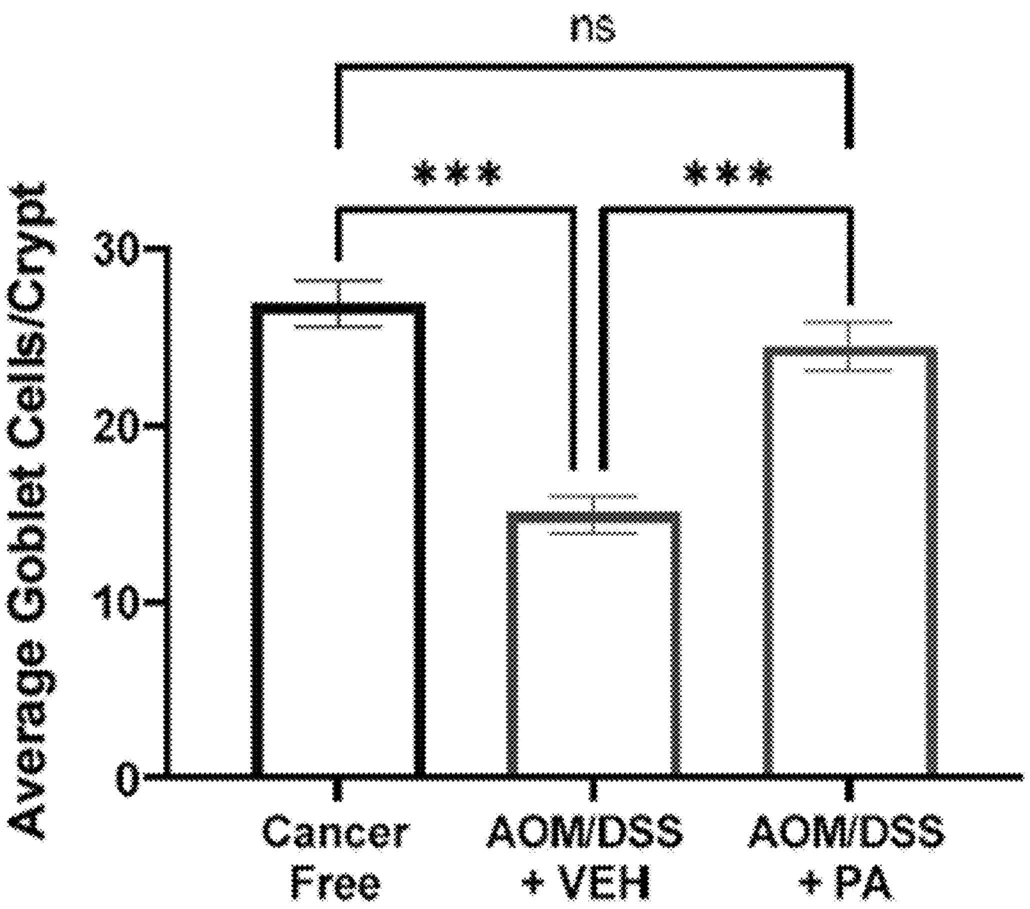
FIG. 4C illustrates average goblet cell count per crypt (n=3/group). Significance determined using an ordinary one-way ANOVA with Tukey's multiple comparisons test.

To investigate PA's effects on intestinal barrier function, colons were stained for H&E and AB (n=3/group), as well as processed for RT-qPCR gene expression analysis of vital markers of gut barrier functions (n=5-7/group). Representative images of H&α-stained distal colons were taken to examine any differences in histopathology and crypt architecture. Colons from CF mice exhibited normal crypt architecture with simple columnar epithelium (FIG. 4A). In the VEH-treated AOM/DSS mice, submucosal invasion and destruction of the crypts is present throughout the colon, which did not appear as severe in the PA-treated AOM/DSS mice (FIG. 4A). Next PA's effects on goblet cells were assessed. Goblet cells are responsible for the production and maintenance of the mucus layer protecting the intestinal barrier. This protective mucus layer has been shown to be diminished in CRC (including in the AOM/DSS model), resulting in increased gut permeability and immune cell infiltration within the colon. To visualize these important goblet cell mucins, colons were stained with AB (FIG. 4B). CF colons exhibited many blue staining goblet cell mucins, indicative of normal mucin production, which were visibly reduced in VEH-treated AOM/DSS mice (FIG. 4B). This did not appear as severe in PA, indicated by more numerous blue staining goblet cell mucins compared to VEH (FIG. 4B). To confirm this observation, average goblet cells per crypt were quantified (FIG. 4C). The colons of VEH-treated AOM/DSS mice, but not those treated with PA, exhibited significantly reduced average of goblet cells per crypt compared to CF ($p \leq 0.05$; FIG. 4C). In fact, goblet cells per crypt were completely rescued with PA treatment (i.e., there was no difference between CF and PA-treated AOM/DSS) (FIG. 4C).

Figure 4D:
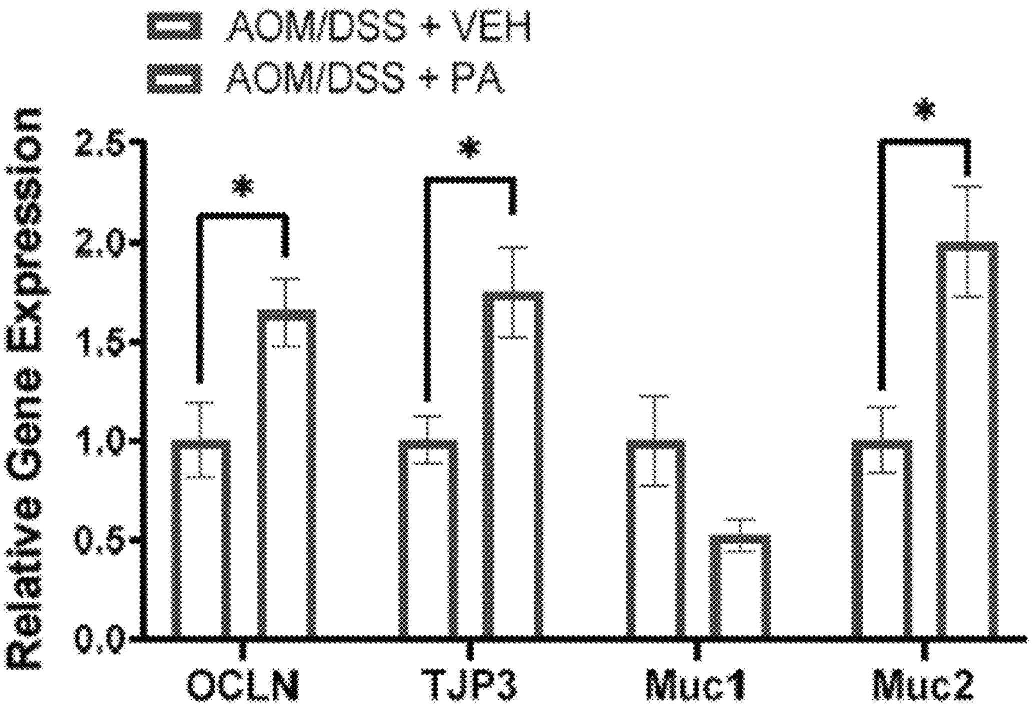
FIG. 4D illustrates RNA isolated from the proximal colons (n=5-7/group) were used for gene analysis via qRT-PCR for tight junction permeability as indicated by occludin (OCLN), tight junction 3 (TJP3), mucin 1 (Muc1), and Muc2. Data were normalized to AOM/DSS+VEH and compared with five reference targets (B2M, TBP, HPRT, HMBS, and H2AFV) which were evaluated for expression stability using GeNorm.

To further examine PA's possible role in strengthening the gut barrier, the expression of colonic genes associated with intestinal barrier integrity including occludin (OCLN) and tight junction protein 3 (TJP3, also known as zonula-occuldin-3) was analyzed, which were both upregulated in PA-treated AOM/DSS mice ($p \leq 0.05$; FIG. 4D). Goblet cell-specific genes in the colon were examined. The goblet cell-specific genes included Muc1, associated with pro-inflammatory and tumor promoting processes, and Muc2, one of the major gel-forming mucins protecting the intestinal epithelial barrier. Muc1 was slightly but non-significantly reduced in PA-treated AOM/DSS mice indicating reduced inflammation ($p=0.08$; FIG. 4D). In contrast, Muc2 expression was significantly increased in PA-treated AOM/DSS mice, indicating reduced intestinal barrier permeability. Taken together, the above results suggest an improvement in the integrity and function of the intestinal barrier with PA treatment ($p \leq 0.05$; FIG. 4D).

Panaxynol Suppresses Macrophages in Colorectal Cancer

Figure 5A:
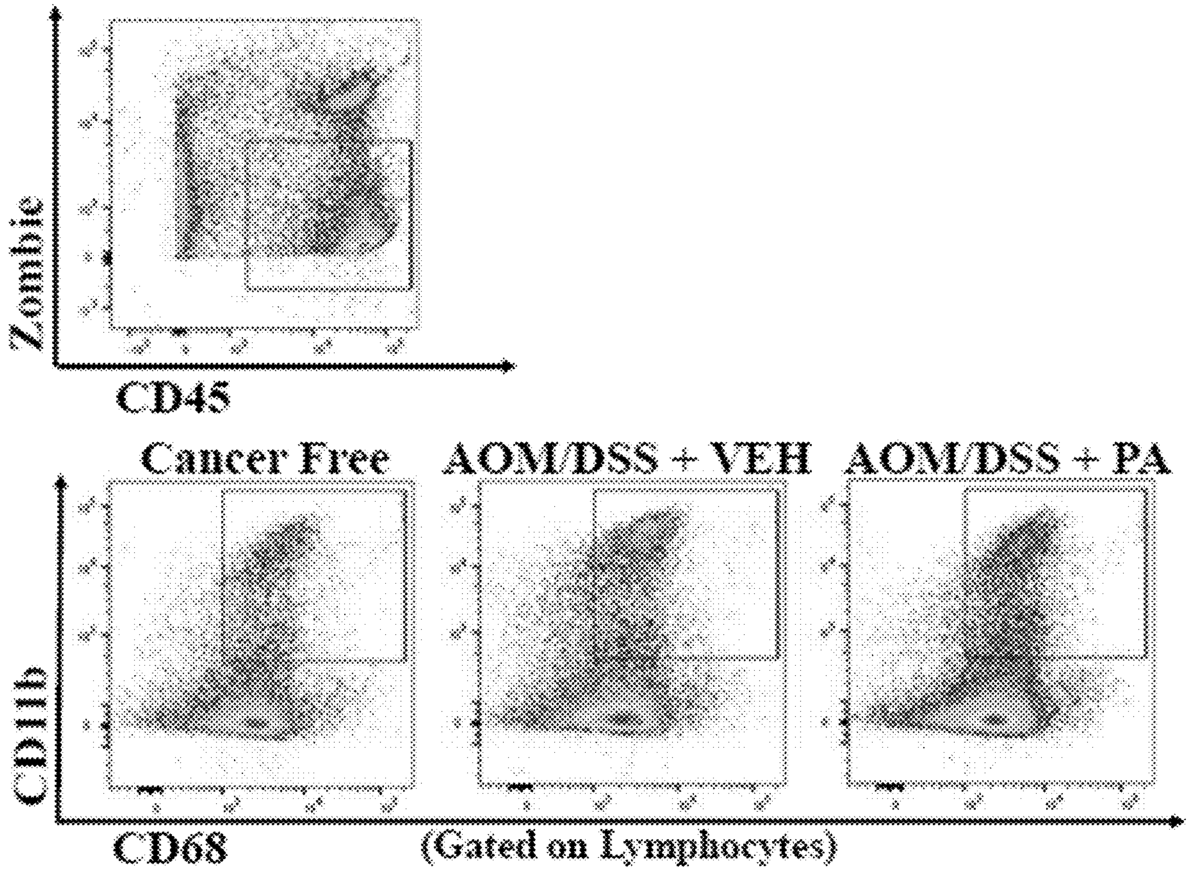
FIG. 5A illustrates lamina propria (LP) cells were isolated from distal colons, gated for non-debris singlets, and considered live immune cells with ZombieGreenNeg/Low and CD45±. Gating strategy of ZombieGreenNeg/Low and CD45+ immune cell population (top panel). From the LiveCD45$^+$ population, CD11b$^+$CD68$^+$ cells were identified as macrophages (bottom panels).
Figure 5B:
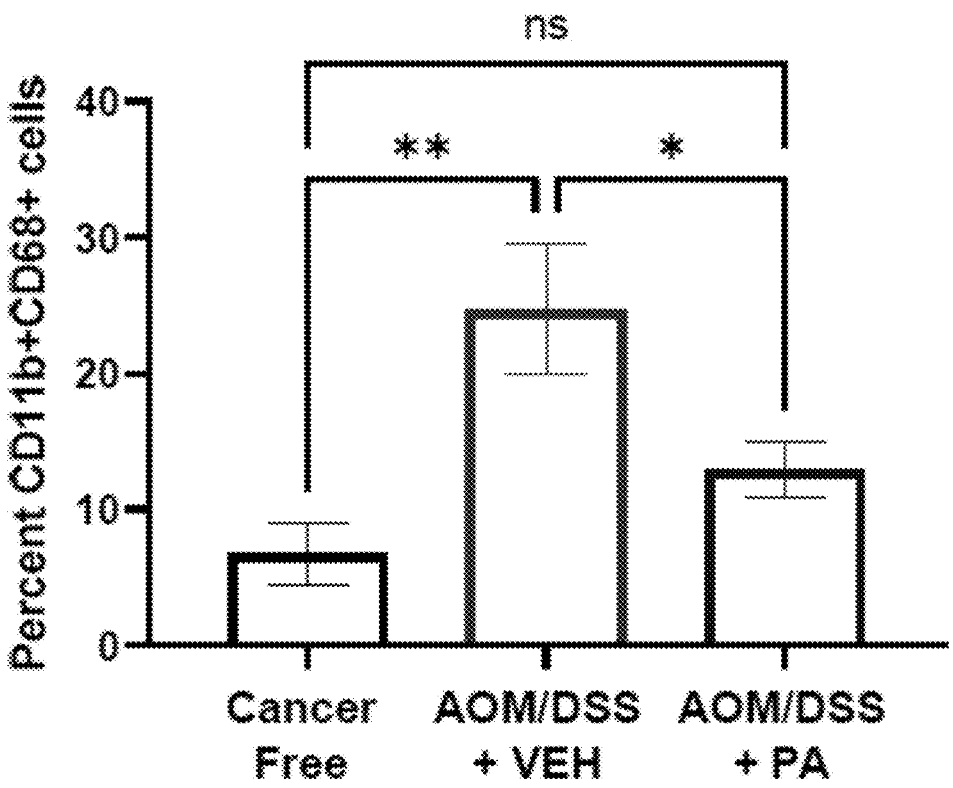
FIG. 5B illustrates relative percentage of CD11b$^+$CD68$^+$ macrophages in the LP of colon (n=5-8/group). Significance determined using an ordinary one-way ANOVA with Tukey's multiple comparisons test.

Previously, the role for macrophages contributing to tumorigenesis in the AOM/DSS CRC model was established. Given that PA reduced colitis through targeting macrophages, whether PA could modify macrophage behavior in CRC was examined. Flow cytometry was performed on colons (with tumors intact) and isolated colonic lamina propria (LP) cells which were gated for non-debris singlets and considered live immune cells with ZombieGreen$^{Neg/Low}$ and $CD45^+$ (FIG. 5A). From the Live$CD45^+$ population, $CD11b^+CD68^+$ cells were identified as macrophages (FIG. 5A). AOM/DSS treated VEH mice exhibited a significantly increased abundance of macrophages in the colon compared to CF ($p \leq 0.05$; FIG. 5B) and this was significantly decreased with PA treatment ($p \leq 0.05$; FIG. 5B) (n=5-8/group).

Figure 5C:
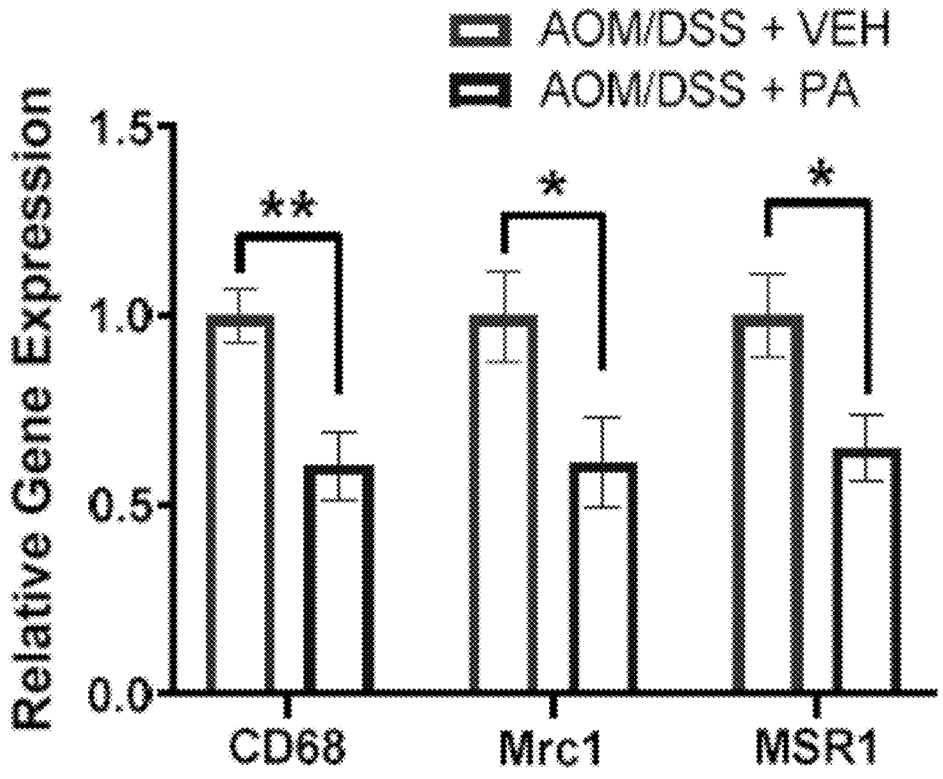
FIG. 5C illustrates RNA isolated from the proximal colons of AOM/DSS treated VEH and PA mice were used for gene analysis via qRT-PCR (n=5-6/group) using pan macrophage markers (CD68, Mrc1, and MSR1).
Figure 5D:
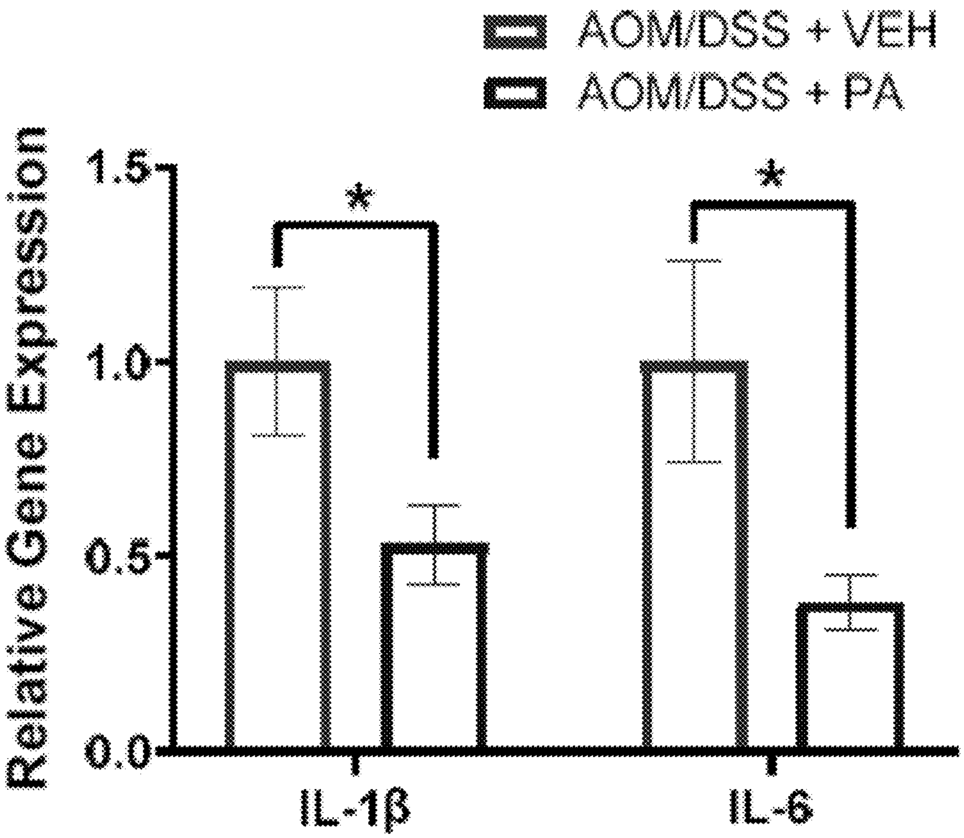
FIG. 5D illustrates RNA isolated from the proximal colons of AOM/DSS treated VEH and PA mice were used for gene analysis via qRT-PCR (n=5-6/group) using pro-inflammatory markers associated with M1 macrophages (IL-1β and IL-6).
Figure 5E:
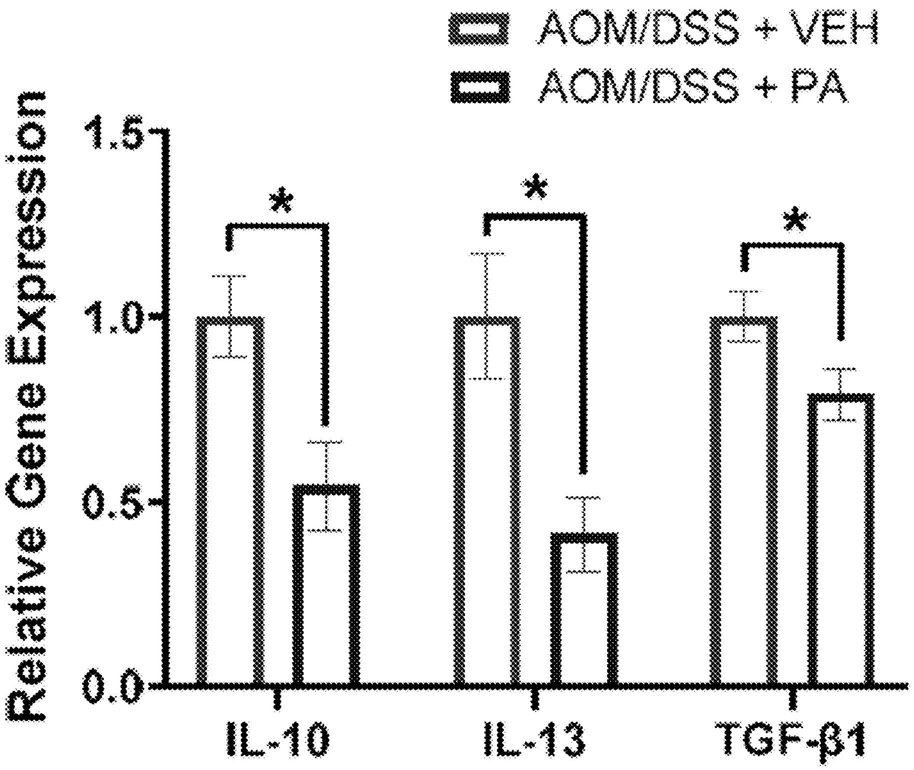
FIG. 5E illustrates RNA isolated from the proximal colons of AOM/DSS treated VEH and PA mice were used for gene analysis via qRT-PCR (n=5-6/group) using pro-tumoral markers associated with M2 macrophages (IL-10, IL-13, and TGF-β1).

To confirm the cellular findings of PA suppressing $CD11b^+CD68^+$ macrophages, RT-qPCR was performed on proximal colons (with tumors intact) of VEH- and PA-treated AOM/DSS mice (n=5-6/group). The expression of genes associated with pan-macrophages were examinedm which were all significantly suppressed in PA-treated AOM/DSS mice, including CD68, mannose receptor C type 1 (Mrc1), and mannose scavenger receptor 1 (MSR-1) compared to that of VEH ($p \leq 0.05$; FIG. 5C). Moreover, colons of PA-treated AOM/DSS mice exhibited significant downregulation of pro-inflammatory genes IL-1β and IL-6, important contributors of clinical symptoms and intestinal inflammation in CRC that are associated with M1 macrophages and to lesser extent T-cells ($p \leq 0.05$; FIG. 5D). More importantly, PA significantly downregulated pro-tumoral genes IL-10, IL-13, and tumor growth factor beta (TGF-β1), all of which are associated with tumorigenic M2 macrophages ($p \leq 0.05$; FIG. 5E).

Figure 5F:
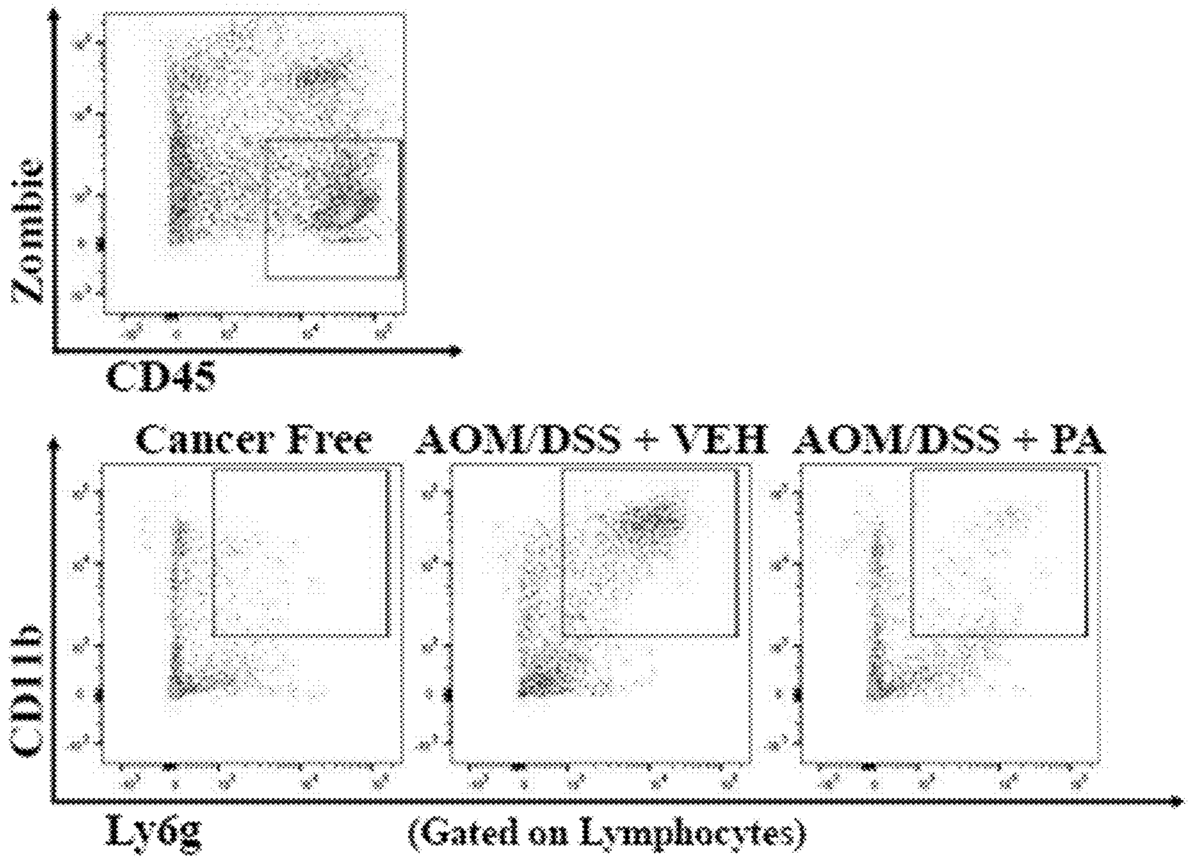
FIG. 5F illustrates gating strategy of ZombieGreenNeg/Low and CD45$^+$ immune cell population (top panel) of colonic LP cells. From the LiveCD45+ population, CD4+ Ly6g+ cells were identified as neutrophils and representative flow plots are shown (bottom panels) (n=2-3/group).
Figure 5G:
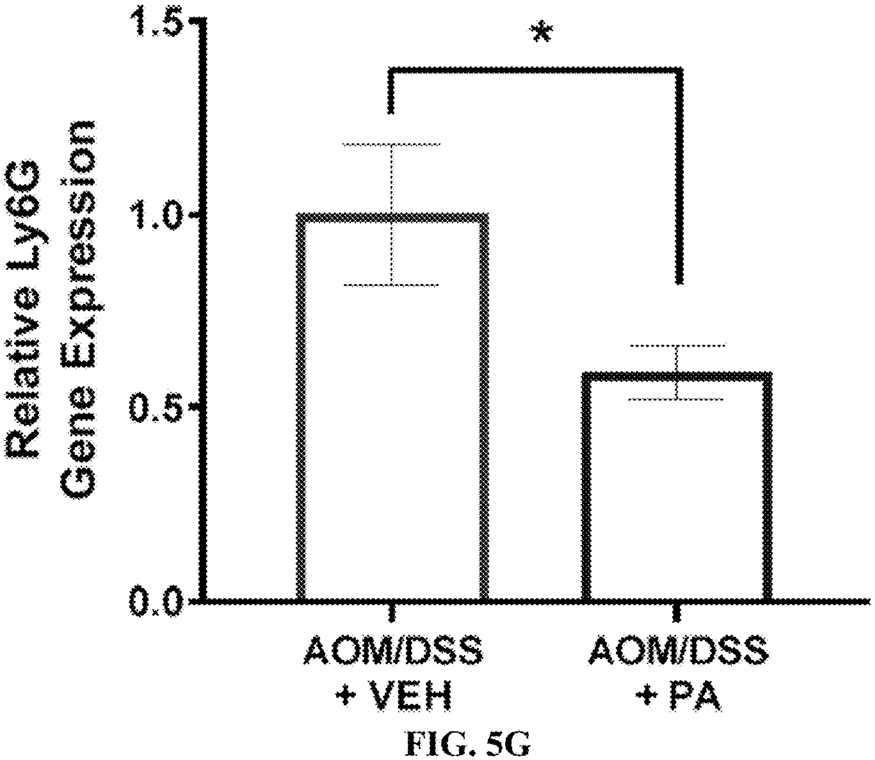
FIG. 5G illustrates RNA isolated from the proximal colons of C57BL/6 AOM/DSS+VEH and AOM/DSS+PA (n=5-6/group) mice after 12 weeks of treatment were used for gene analysis via qRT-PCR using neutrophil marker Ly6G. For all qRT-PCR, data were normalized to AOM/DSS+VEH and compared with five reference targets (B2M, TBP, HPRT, HMBS, and H2AFV) which were evaluated for expression stability using GeNorm.

In addition to macrophages, neutrophils were assessed which are important inflammatory immune cells whose increased abundance is strongly associated with more severe tumorigenesis and worse prognosis in CRC. A small subset of mice (n=2-3/group) was used to grossly observe differences in neutrophils between groups. PA appeared to protect against the increased abundance of neutrophils in the colon (FIG. 5F); however, statistics were not performed given the small sample size. Nonetheless, this finding was confirmed using RT-qPCR where it was documented that PA significantly downregulated neutrophil marker Ly6g in the proximal colon compared to that of VEH ($p \leq 0.05$; FIG. 5G).

Figure 6A:
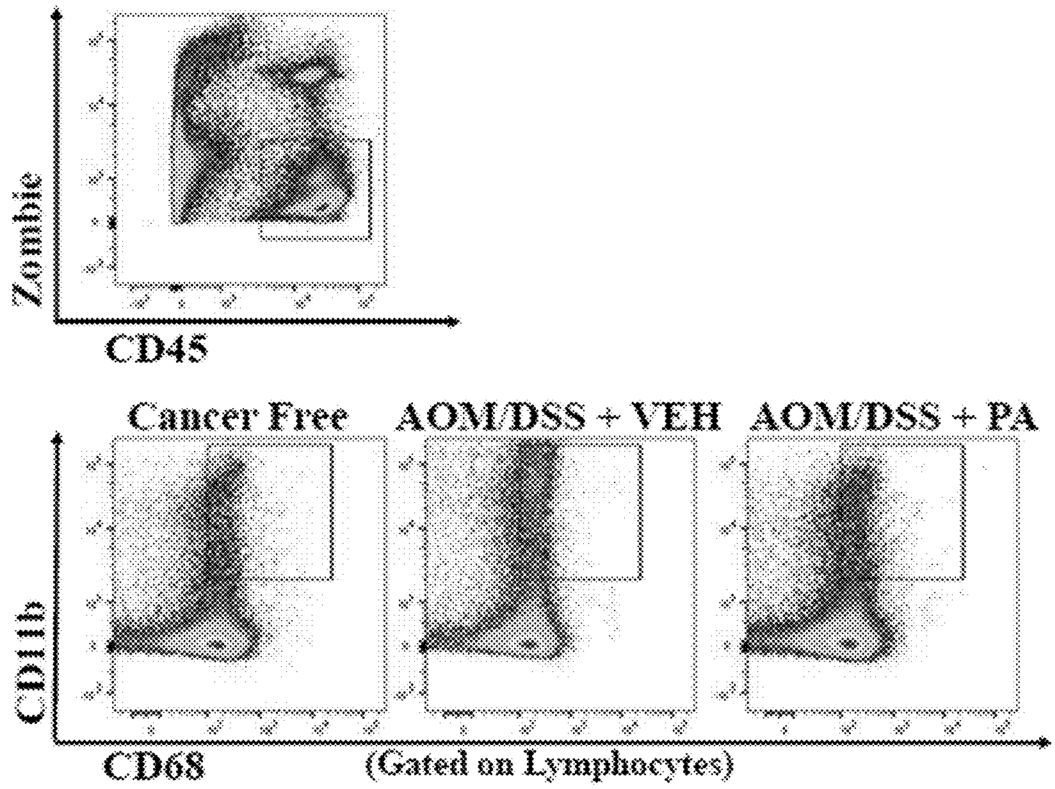
FIG. 6A illustrates lamina propria (LP) cells were isolated from colons following tumor removal (n=5-7/group), gated for non-debris singlets, and considered live immune cells with ZombieGreenNeg/Low and CD45$^+$. Gating strategy of ZombieGreenNeg/Low and CD45$^+$ immune cell population (top panel). From the LiveCD45$^+$ population, CD11b$^+$CD68$^+$ cells were identified as macrophages (bottom panels).
Figure 6B:
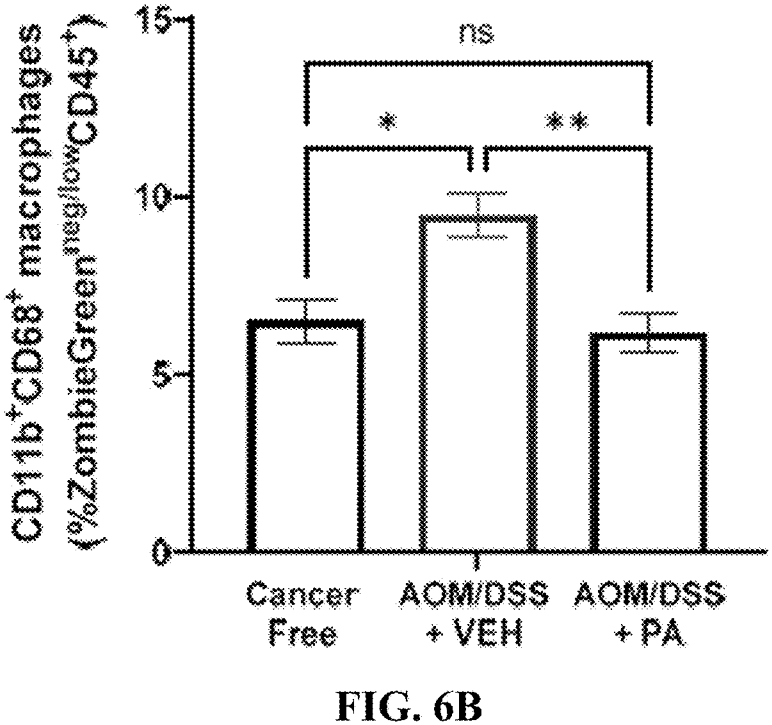
FIG. 6B illustrates relative percentage of CD11b$^+$CD68$^+$ macrophages in the LP of colon. Significance was determined using an ordinary one-way ANOVA with Tukey's multiple comparisons test.
Figure 6C:
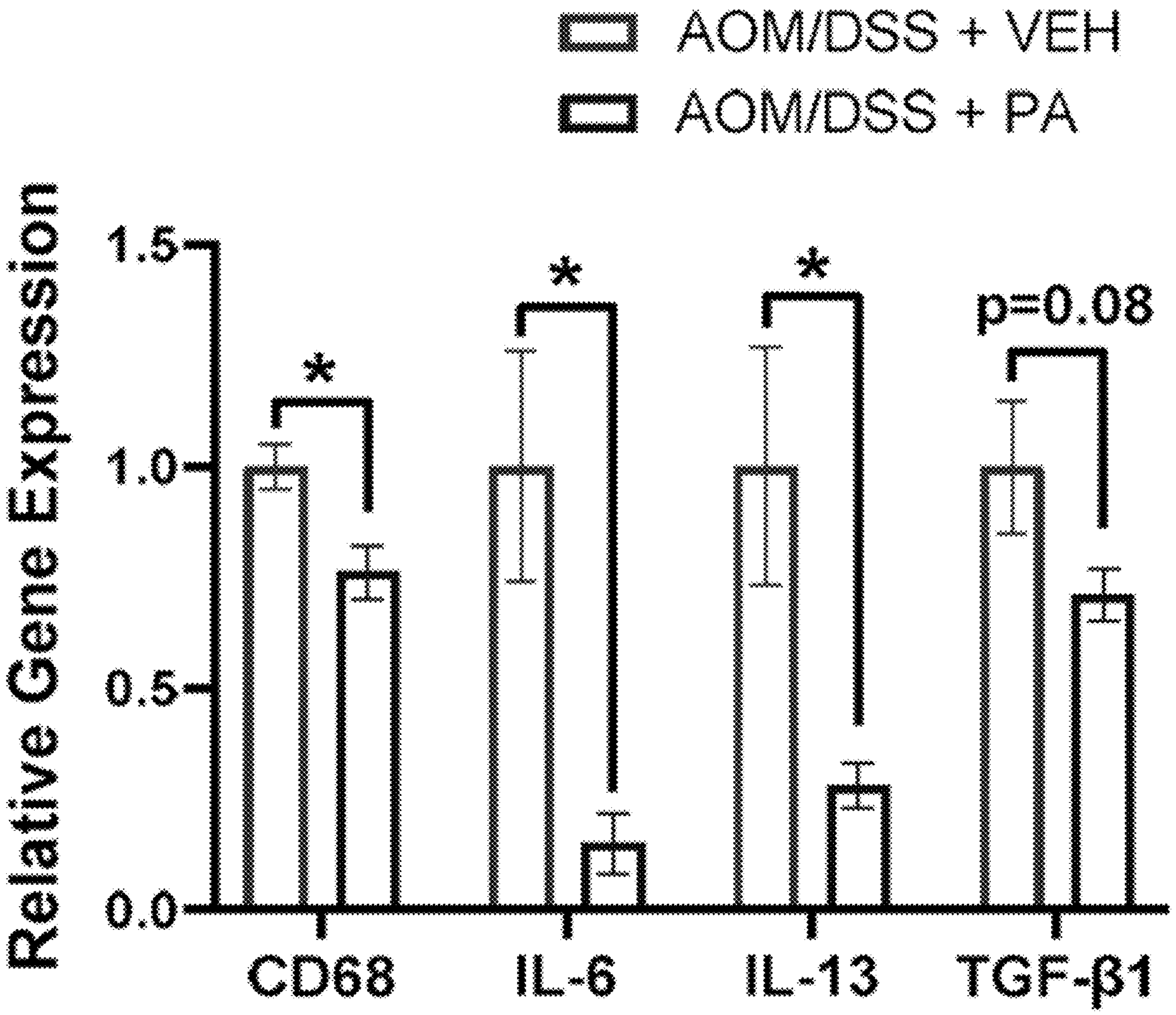
FIG. 6C illustrates RNA isolated from colonic tumors of AOM/DSS treated VEH and PA mice were used for gene analysis via qRT-PCR (n=4-5/group) using pan macrophage marker (CD68), pro-inflammatory marker associated with M1 macrophages (IL-6); and pro-tumoral markers associated with M2 macrophages (IL-13 and TGF-β1).
Figure 6D:
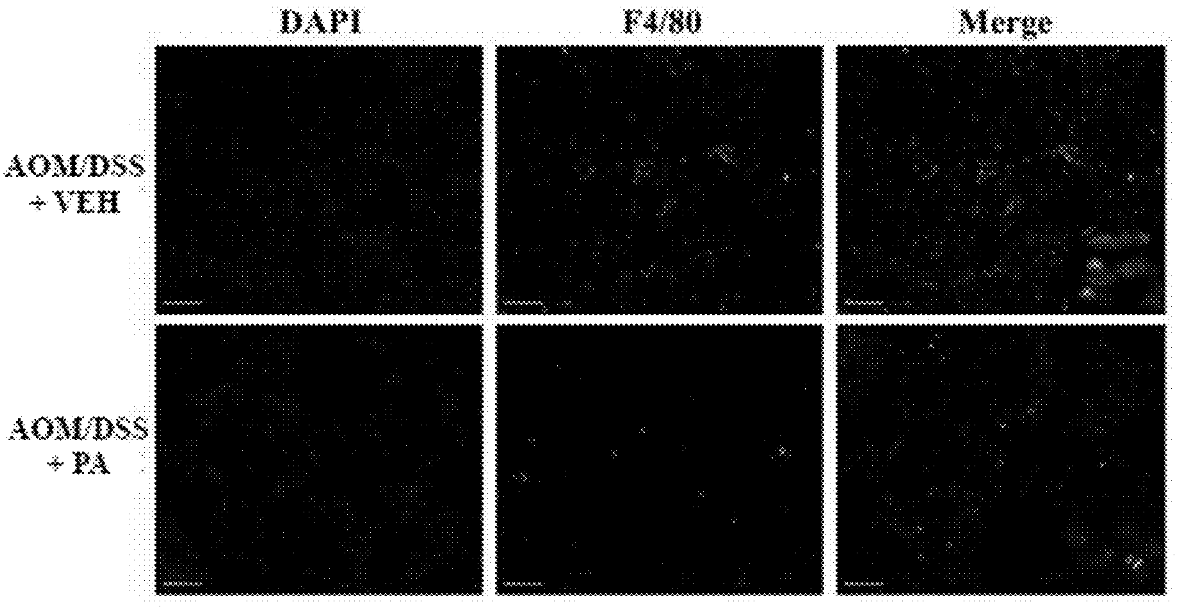
FIG. 6D illustrates Representative 20× images of immunofluorescence staining of pan macrophage marker F4/80 in colonic tumors of AOM/DSS+VEH and AOM/DSS+PA mice (n=3/group). DAPI (blue) as an individual channel for visualization of nuclei (left), F4/80 (green) as an individual channel (middle) and merged (right). Scale bar=100 μm.

To confirm that the suppression of macrophages by PA was not confounded by the fewer and smaller tumors in the colon of PA-treated mice, the assessment of macrophages in the colon following tumor removal (n=5-7/group) was repeated. Consistent with the aforementioned findings, the relative abundance of macrophages in colons were significantly increased in VEH-treated AOM/DSS mice compared to CF ($p \leq 0.05$; FIG. 6A-6B) and this response was ameliorated by PA ($p \leq 0.05$; FIG. 6A-B). RT-PCR was performed on the removed tumors (n=4-5/group) and consistent with the cellular data, PA significantly suppressed pan-macrophage marker CD68 in tumors ($p \leq 0.05$; FIG. 6C). Further, PA suppressed select inflammatory mediator IL-6 ($p \leq 0.05$) associated with M1 macrophages, as well as pro-tumoral mediators IL-13 ($p \leq 0.05$) and TGF-01 (p=0.08) which are tightly associated with M2 macrophages (FIG. 6C). The reduction in macrophages by PA was further confirmed by immunofluorescence staining for pan macrophage marker F4/80 (FIG. 6D) (n=3/group).

Figure 6E:
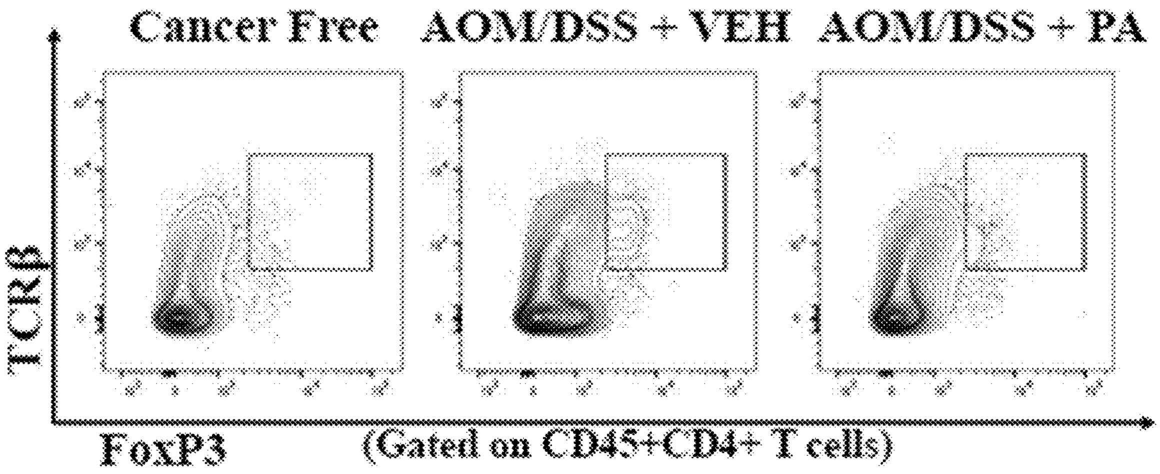
FIG. 6E illustrates representative flow plots of TCRβ$^+$ FoxP3$^+$ LP cells from colons following tumor removal in cancer free, AOM/DSS+VEH, and AOM/DSS+PA mice were identified as regulatory T-cells (T-regs).
Figure 6F:
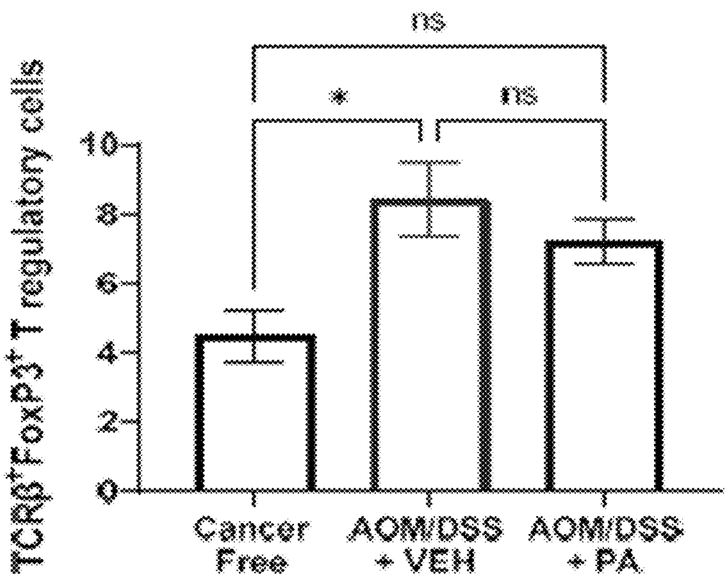
FIG. 6F illustrates relative percentage of TCRβ$^+$FoxP3$^+$ T-regs in the colonic LP. Significance was determined using an ordinary one-way ANOVA with Tukey's multiple comparisons test.
Figure 6G:
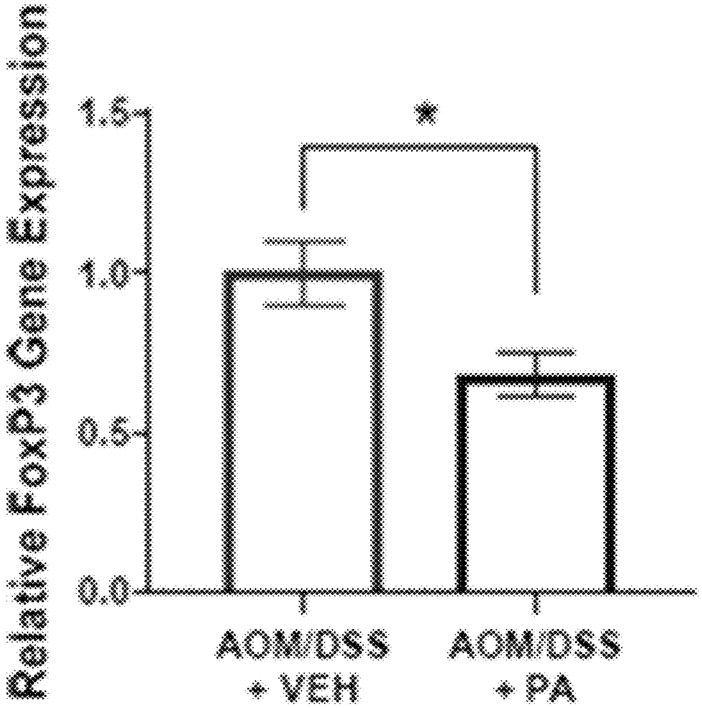
FIG. 6G illustrates RNA isolated from colonic tumors of C57BL/6 AOM/DSS+VEH and AOM/DSS+PA (n=4-5/group) mice after 12 weeks of treatment were used for gene analysis via qRT-PCR using T-reg marker FoxP3. For all qRT-PCR, data were normalized to AOM/DSS+VEH and compared with five reference targets (B2M, TBP, HPRT, HMBS, and H2AFV) which were evaluated for expression stability using GeNorm.

In addition to macrophages, the effects of PA were assessed on regulatory-T cells (T-regs), important promoters of CRC development, inflammation, and intestinal damage (n=5-7/group). VEH but not PA-treated AOM/DSS mice exhibited significantly increased $TCR\beta^{+}FoxP3^{+}$ T-regs in tumor-removed colons compared to CF ($p \leq 0.05$; FIGS. 6E-6F). Although there was no difference in colonic $TCR\beta^{+}$ $FoxP3^{+}$ T-regs between VEH and PA (FIGS. 6E-F), a decrease in expression of T-cell marker Foxp3 in tumors (n=4-5/group) from PA-treated mice was observed compared to VEH ($p \leq 0.05$; FIG. 6G).

Figure 7A:
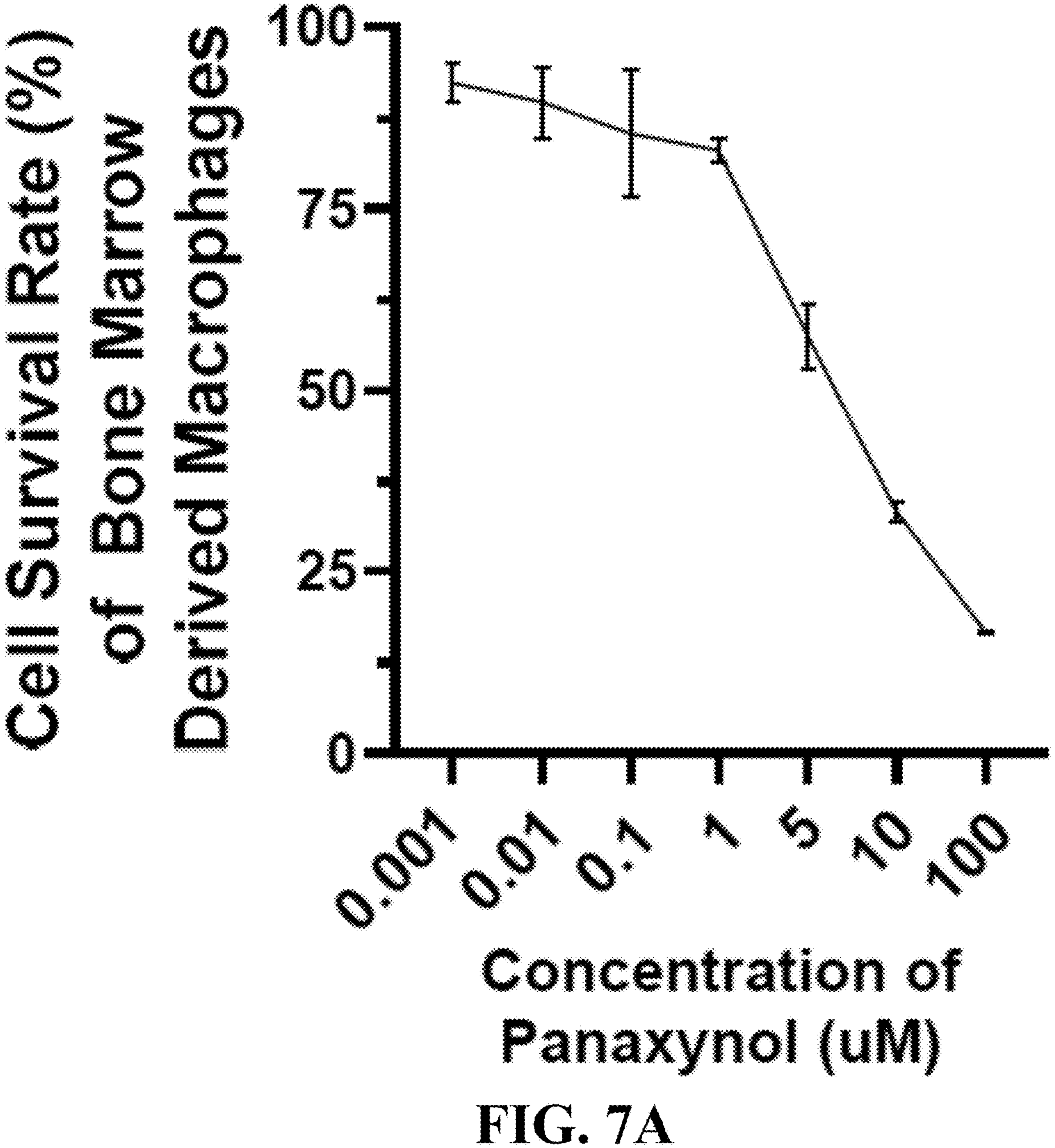
FIG. 7A illustrates percent cell survival rate of bone marrow derived macrophages (BMDMs) treated with various concentrations of panaxynol in vitro for 24 hr via CCK-8.
Figure 7B:
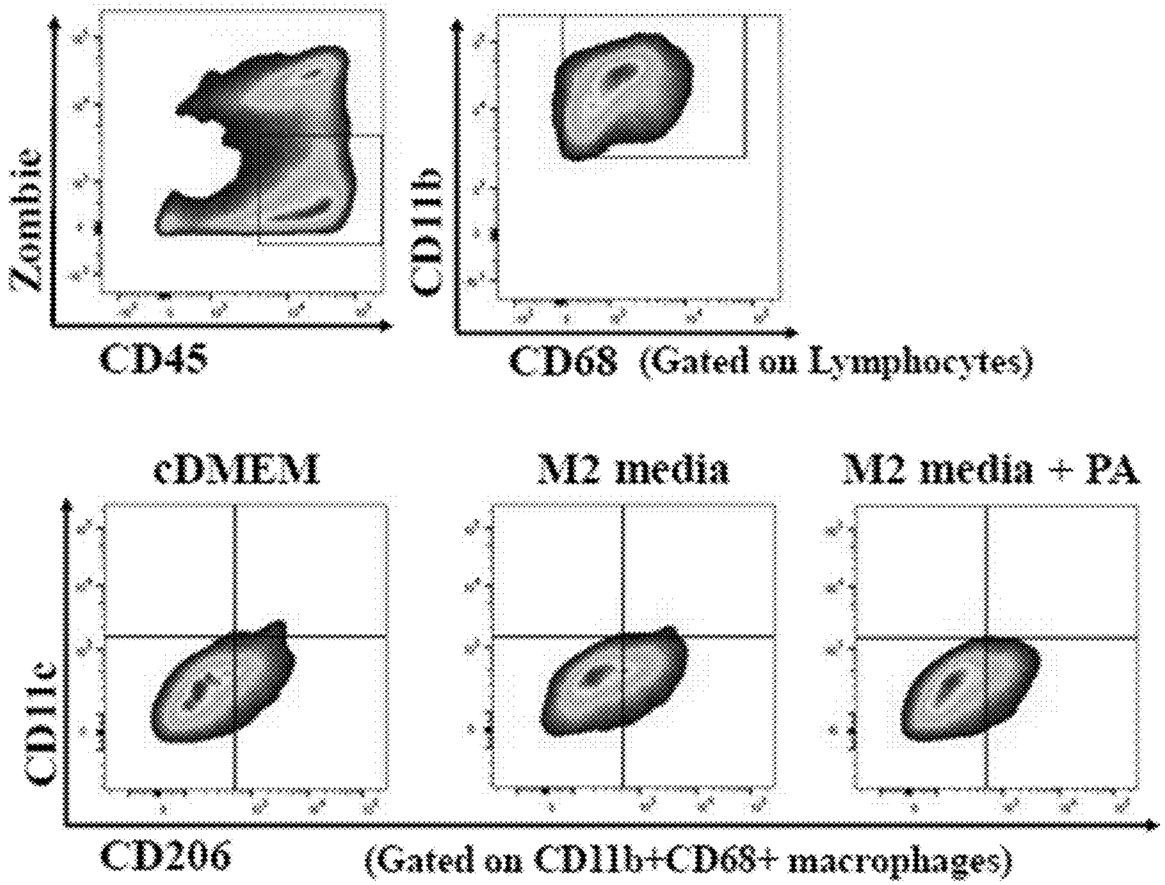
FIG. 7B illustrates flow plots identifying gating strategy for ZombieGreenNeg/LowCD45$^+$ immune cells (top panel) and macrophage phenotype (bottom panels) using CD11c and CD206 expression in BMDMs incubated with cDMEM or M2-like macrophage media (IL-4) with or without 1 μM PA.
Figure 7C:
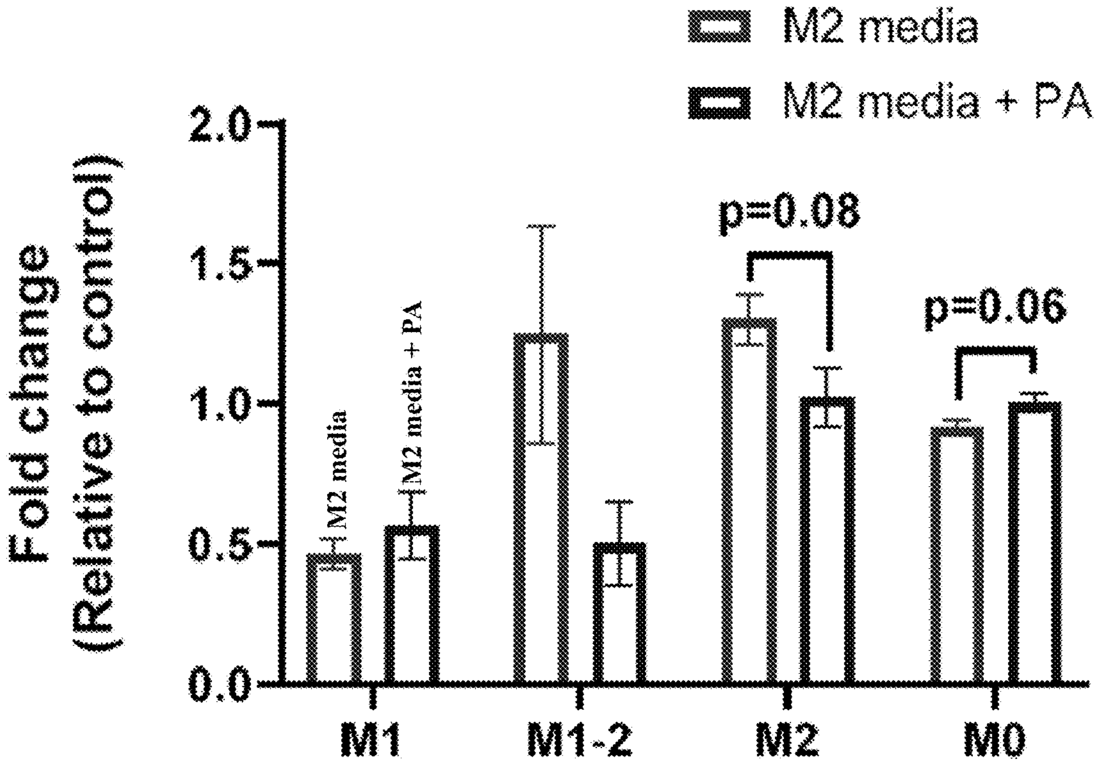
FIG. 7C illustrates relative fold change in percentage of macrophage phenotypes in BMDMs treated with or without 1 μM PA in the presence of M2-marophage stimulating media. Significance was determined using multiple Student's t-test ($p \leq 0.05$).

Panaxynol Reduces Cell Survival of BMDMs and Colorectal Cancer Cells and Decreases Pro-Tumoral M2 Macrophages In Vitro In vivo results of PA's suppressive effects on macrophages were confirmed in vitro using bone marrow derived macrophages (BMDMs). Three independent experiments were carried out for each assessment. First, CCK-8 assays were used to evaluate the cell viability of BMDMs after treatment with various concentrations of PA for 24 hr (FIG. 7A). PA inhibited cell survival in a concentration-dependent manner with an $IC_{50}$ value of ~7 μM for PA on BMDMs (FIG. 7A). The 1 μM concentration of PA was selected for additional in vitro studies. To further explore the effects of PA on macrophage polarization, flow cytometry was performed on PA-treated BMDMs incubated with IL-4 to polarize BMDMs towards M2-like macrophages (i.e., pro-tumor macrophages) (FIG. 7B-7C). PA treated BMDMs cultured with M2 media increased naïve M0 macrophages (p=0.06), representing PA-treated BMDMs unaffected by this M2 stimulus, and non-significantly reduced transitional M1-M2 (p=0.12) and M2 macrophages (p=0.08) compared to VEH-treated BMDMs cultured with M2 media.

Figure 7D:
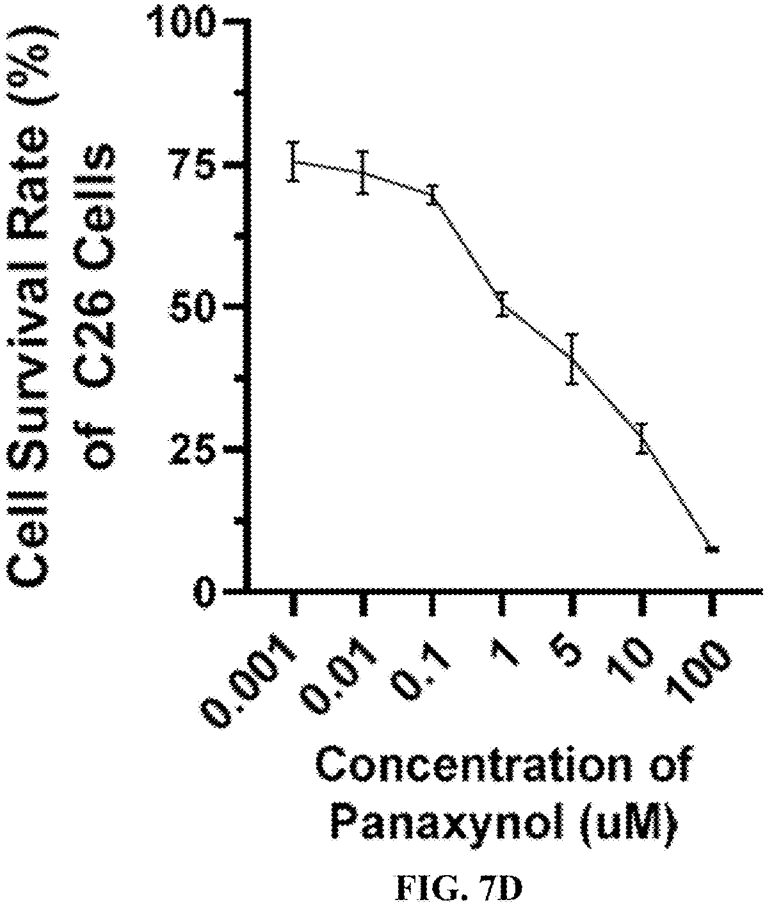
FIG. 7D illustrates percentage cell survival rate of C26 colorectal cancer cells incubated with C26 tumor conditioned media (C26 CM) treated with various concentrations of panaxynol in vitro.
Figure 7E:
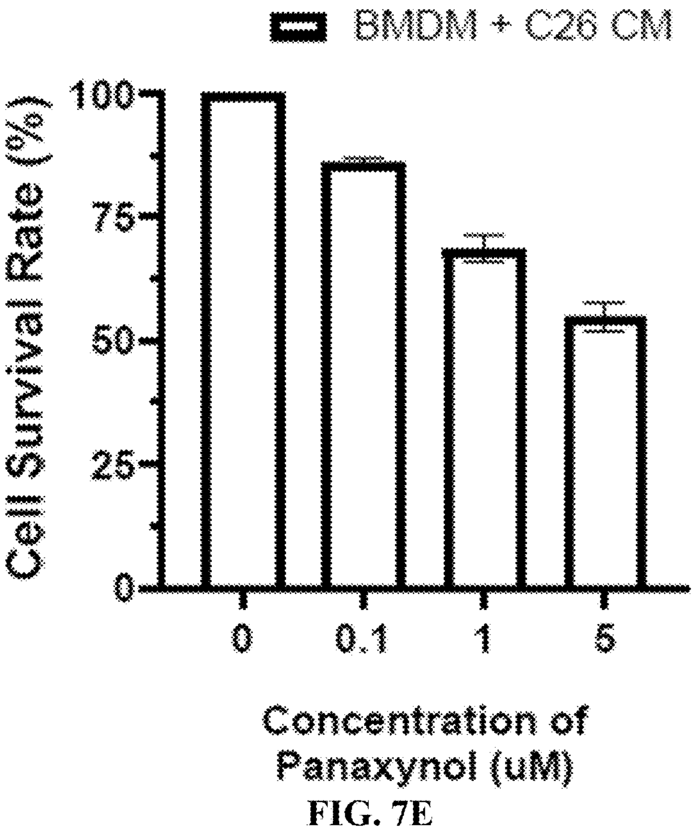
FIG. 7E illustrates percentage cell survival rate of bone marrow derived macrophages (BMDMs) incubated with C26 tumor conditioned media (C26 CM) treated with various concentrations of panaxynol in vitro.
Figure 8A:
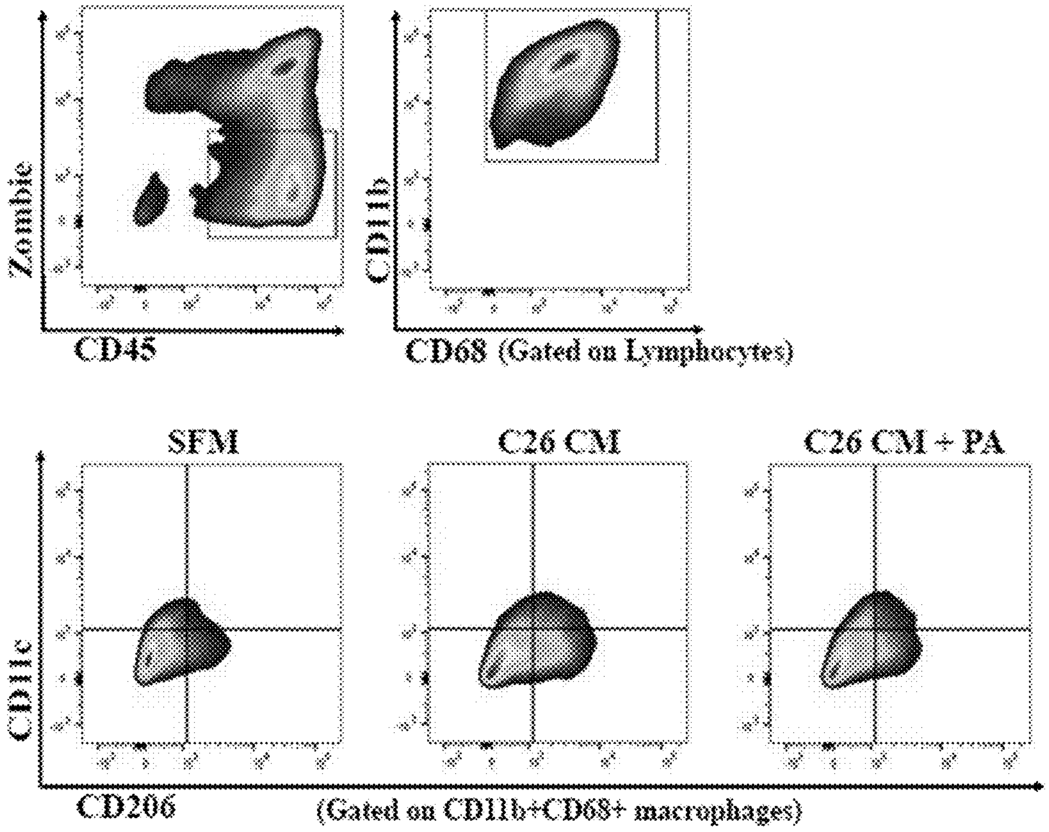
FIG. 8A illustrates flow plots identifying gating strategy for ZombieGreenNeg/LowCD45$^+$ immune cells (top left panel), CD11b$^+$CD68$^+$ macrophages (top left panel), and macrophage phenotype (bottom panels) using CD11c and CD206 expression in BMDMs incubated with SFM, C26 CM, or C26 CM+PA. (G) Relative fold change in percentage of macrophage phenotypes in BMDMs incubated with C26 CM or C26 CM+PA.
Figure 8B:
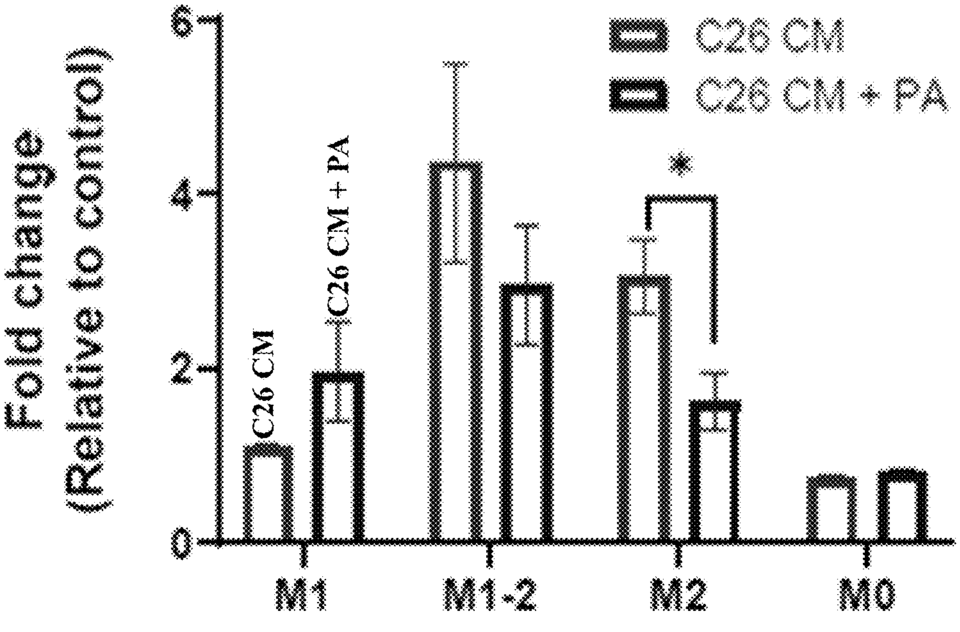
FIG. 8B illustrates relative fold change in percentage of macrophage phenotypes in BMDMs incubated with C26 CM or C26 CM+PA.

Next, in vitro experiments using C26 CRC cells were performed to confirm in vivo results of PA reducing CRC at least in part through its suppressive effects on macrophages. Three independent experiments were carried out for each assessment. CCK-8 assays were performed to evaluate PA's effects on cell viability of C26 CRC cells (FIG. 7D). PA exhibited potent anti-proliferative activity against C26 CRC cells in a concentration-dependent manner with an IC50 value of 1 μM (FIG. 7D). To further explore the anti-cancer activity of PA, BMDMs cultures were treated with C26 CM for 48 hr with various concentrations of PA to assess its effects on macrophage survival (FIG. 7E). It was observed that 1 μM and 5 μM of PA reduced survival by 31.5% and 45.3%, respectively (FIG. 7E). Further, the effects of PA on macrophage polarization in a CRC context were evaluated by culturing BMDMs with C26 CM for 48 hr with PA. No significant differences were detected in the relative abundance of M1, M1-M2, and M0 macrophages between VEH- and PA-treated BMDMs cultured with C26 CM (FIG. 8B). However, PA significantly reduced the relative abundance of pro-tumoral M2 macrophages in BMDMs cultured with C26 CM ($p \leq 0.05$; FIG. 7G).

Panaxynol Improves Disease Severity and Symptomology in Chronic Murine Colitis.

Figure 9F:
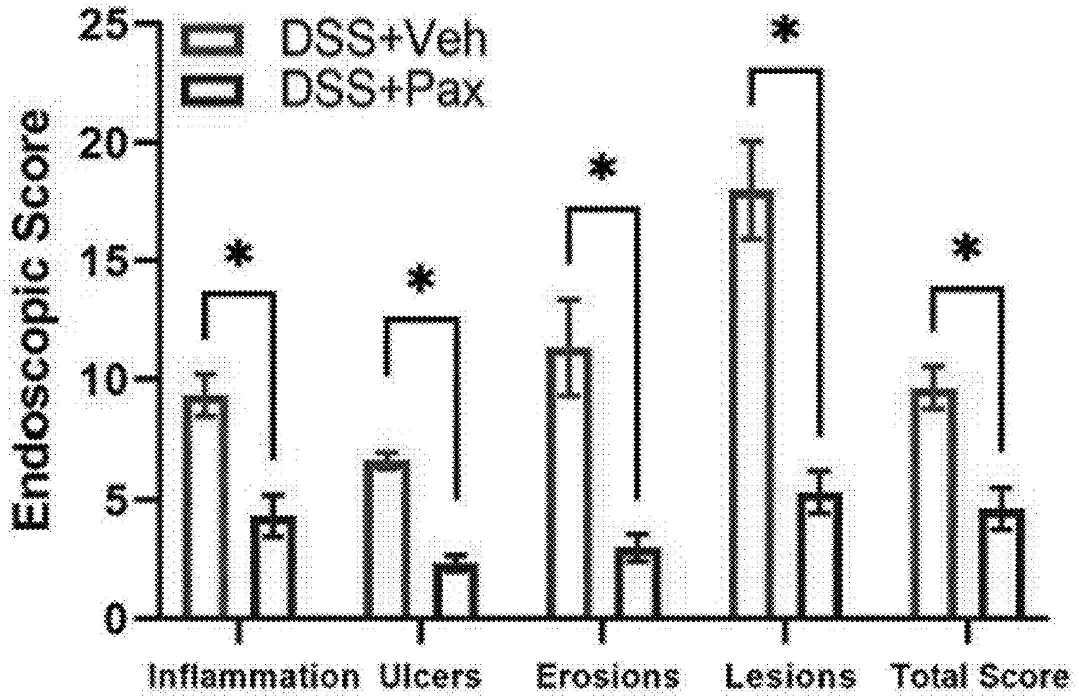
FIG. 9F illustrates endoscopic scores (n=2-3/group). Unpaired t-test.

The experimental design for inducing chronic murine colitis is presented in FIG. 9A. To validate the model, Control mice were compared to DSS-treated groups. DSS alone caused significant change in body weight compared to Controls (23.8±0.6g vs 20.7±0.4g, p=0.001). DSS-treated mice demonstrated worsened stool consistency (FIG. 9B) and rectal bleeding (FIG. 9C) compared to Control, resulting in an increased overall symptom score (FIG. 9D). Within DSS-treated groups, DSS+Pax demonstrated significantly ($p \leq 0.05$) improved DAI scores (FIGS. 9B-9D) compared to DSS+Veh throughout the course of treatment (FIGS. 9B-9D). This improvement was largely attributed to improved stool consistency (FIG. 9B) and decreased rectal bleeding (FIG. 9C), since there were no significant differences in body weight within DSS-treated groups by end of study (20.7±0.4g vs 20.3±0.7g, p=0.862). End of study (i.e., day 42) endoscopies revealed DSS+Pax improved gross architecture of the colon (FIG. 9E) resulting in significantly improved endoscopic scores, represented by a 54% reduction (p=0.016) in inflammation, 65% reduction (p=0.001) in ulcerations, 74% reduction (p=0.017) in erosions, and 70% reduction (p=0.005) in total lesions, leading to a 52% reduction (p=0.016) in their total endoscopic scores compared to DSS+Veh (FIG. 9F).

Panaxynol Improves Disease Severity and Symptomology in Acute Murine Colitis.

Figure 10B:
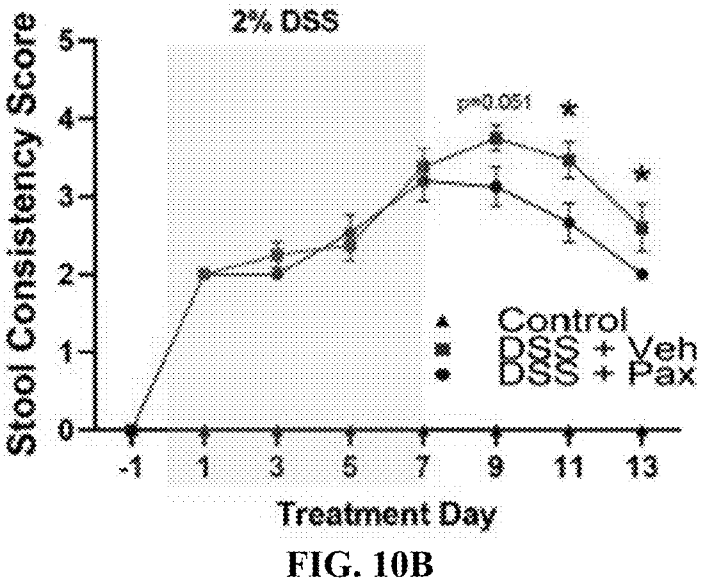
FIG. 10B illustrates stool consistency score quantified using disease activity index (n=10-20/group).
Figure 10C:
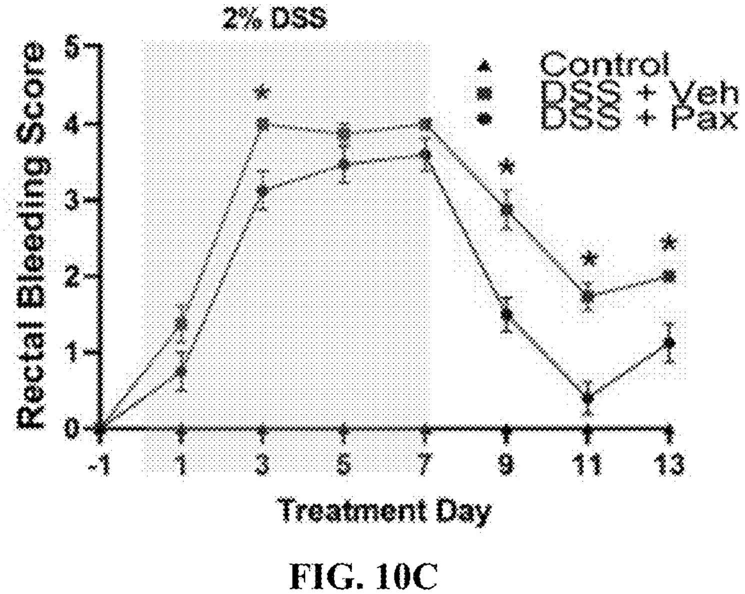
FIG. 10C illustrates rectal bleeding score quantified using disease activity index (n=10-20/group).
Figure 10D:
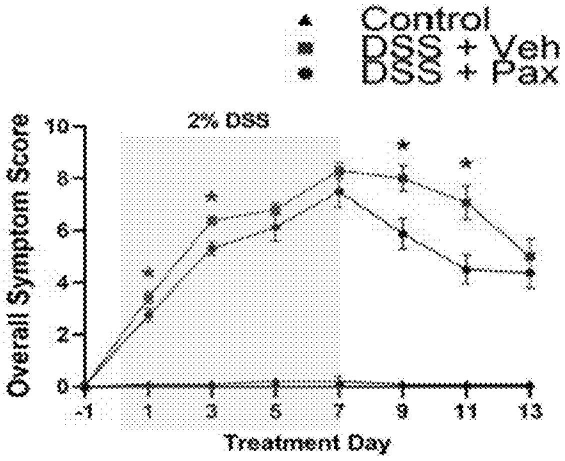
FIG. 10D illustrates overall symptom score quantified using disease activity index (n=10-20/group).
Figure 10E:
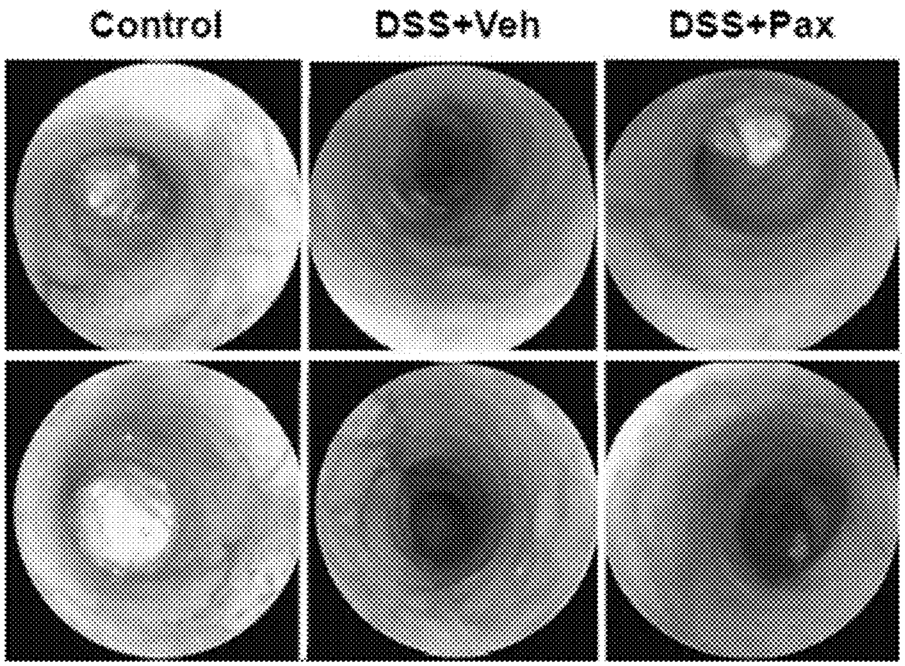
FIG. 10E illustrates representative images from end-of-study endoscopies.
Figure 10F:
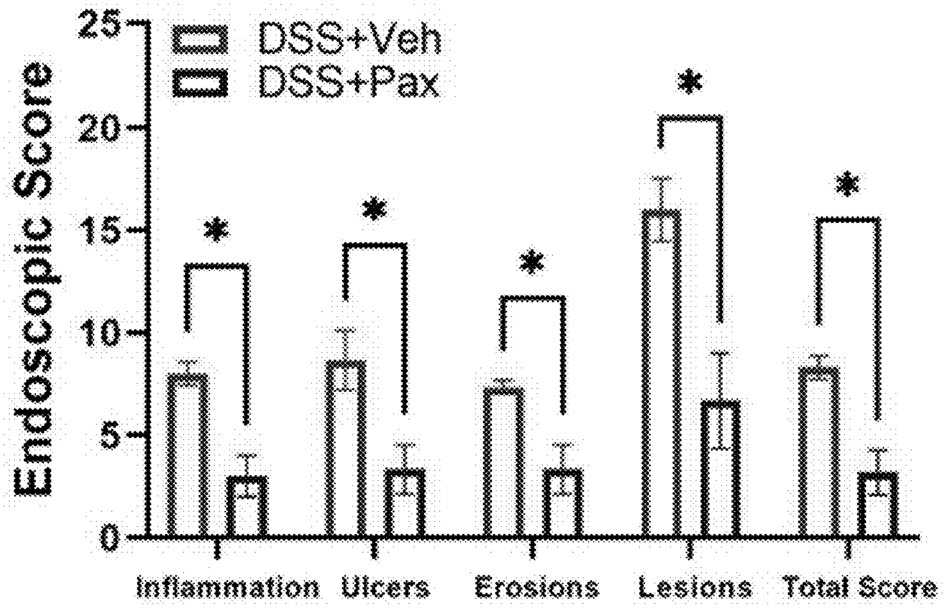
FIG. 10F illustrates endoscopic scores (n=2-3/group). Unpaired t-test.

Since benefits of panaxynol with chronic colitis were observed, the effects of panaxynol on acute colitis and associated mechanisms were assessed. The experimental design for inducing acute colitis is presented in FIG. 10A. To validate the model, Control mice were compared to DSS-treated groups. DSS alone caused significant changes in body weight compared to Controls (20.9±0.2g vs 18.4±0.6g, p=0.004). DSS-treated mice demonstrated worsened stool consistency (FIG. 10B) and rectal bleeding (FIG. 10C) compared to Control, resulting in an increased overall symptom score (FIG. 10D). Within DSS-treated groups, DS S+Pax demonstrated significantly ($p \leq 0.05$) improved DAI scores compared to DSS+Veh throughout the course of treatment (FIGS. 10B-10D). This improvement was largely attributed to improved stool consistency (FIG. 10B) and decreased rectal bleeding (FIG. 10C), since there were no significant differences in body weight within DSS-treated groups by end of study (18.4±0.6g vs 19.1±0.4g, p=0.383). End of study (i.e., day 14) endoscopies showed DSS+Pax improved gross architecture of the colon (FIG. 10E) evidenced by significantly improved endoscopic scores, represented by a 63% reduction (p=0.012) in inflammation, 62% reduction (p=0.047) in ulcers, 55% reduction (p=0.033) in erosions, 58% reduction (p=0.029) in total lesions, and a resulting 62% reduction (p=0.014) in their total endoscopic scores compared to DSS+Veh (FIG. 10F).

Panaxynol Reduces Colonic Crypt Distortion Due to DSS and Improves Mucosal Architecture.

Figure 11A:
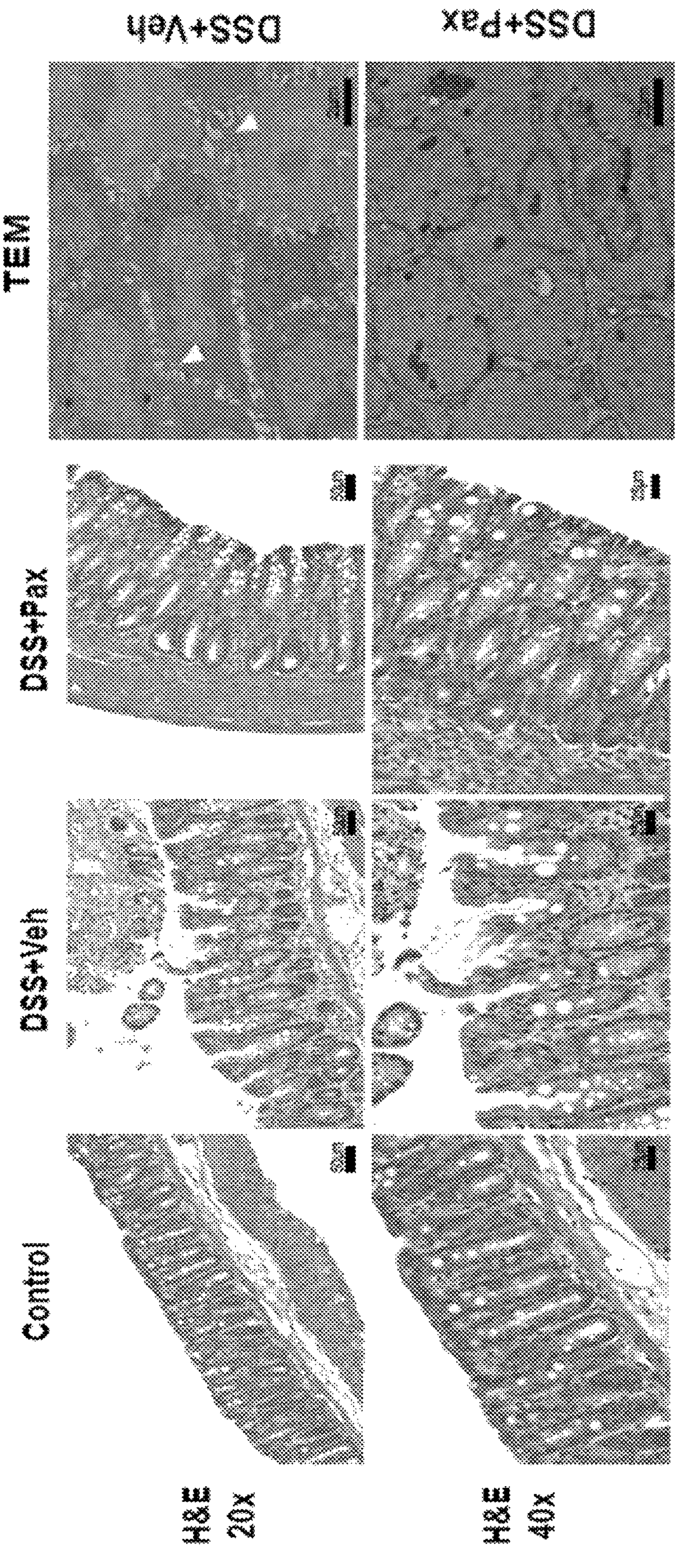
FIG. 11A illustrates representative images of hematoxylin and eosin (H&E) staining of the distal colon taken at 20× (scale bar=50 μm) and 40× (scale bar=25 μm); and representative transmission electron microscopy (TEM) images of the distal colon (scale bar=2 μm) showing intercellular edema (arrows).
Figure 11B:
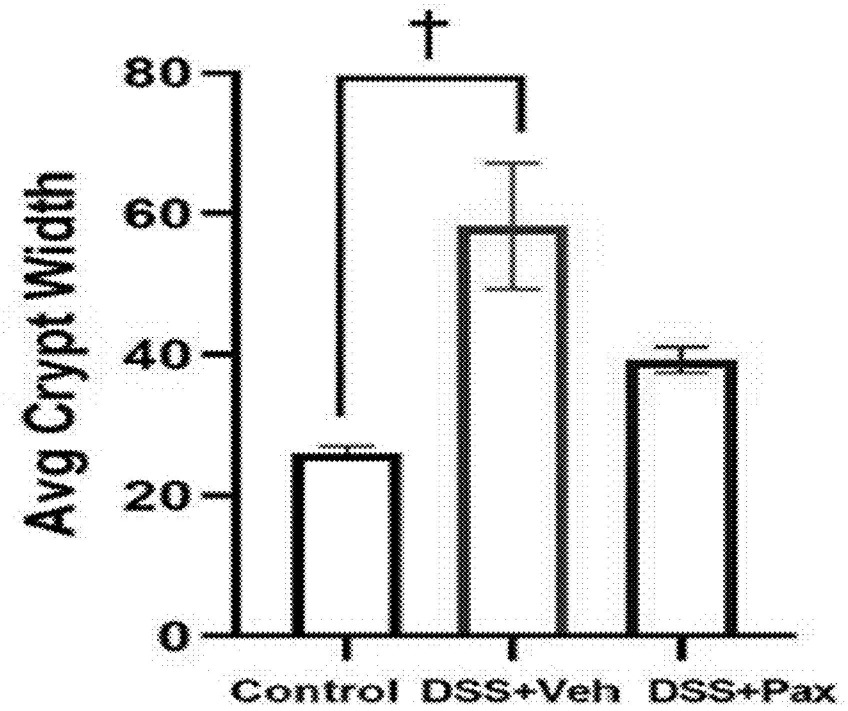
FIG. 11B illustrates average crypt width (n=2-4/group).
Figure 11C:
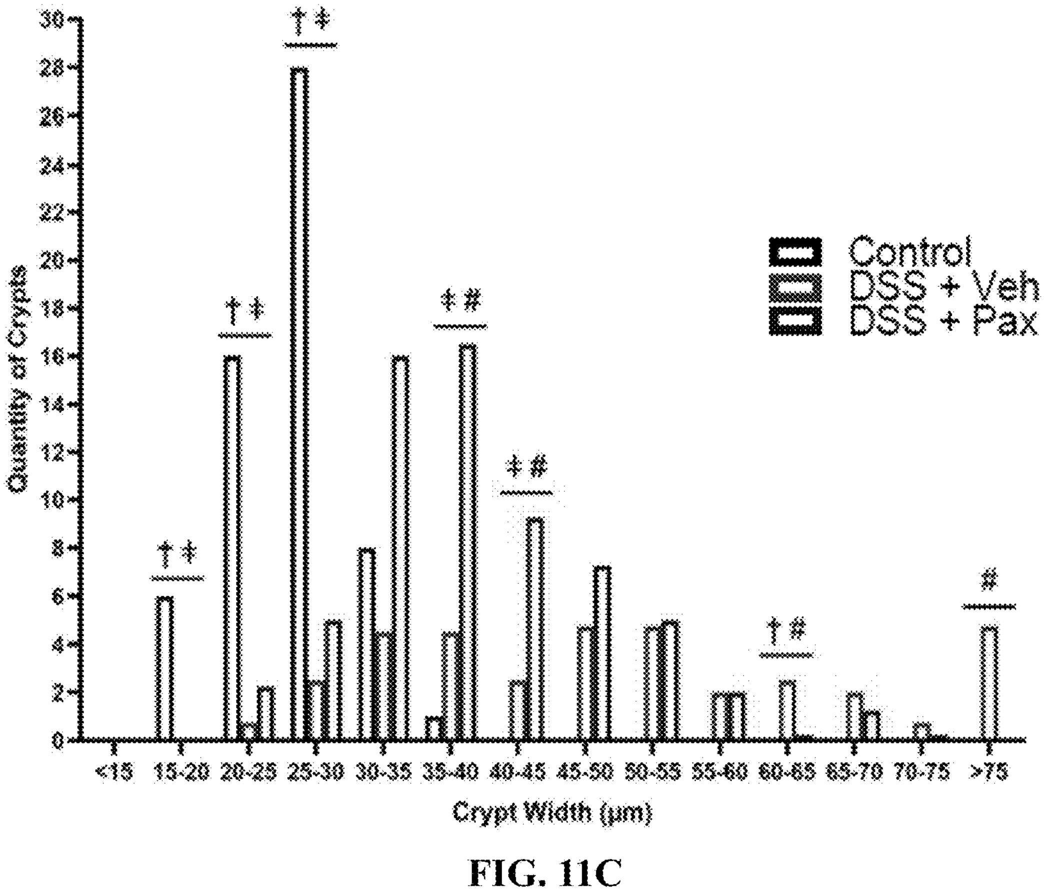
FIG. 11C illustrates crypt width distribution curve (n=2-4/group).

H&E images revealed general colonic architecture as well as crypt architecture of the distal colon (FIG. 11A). As expected, Control crypts were tightly packed, organized, and arranged with little-to-no gaps. Histological layers of the colon, including the LP, were intact. DSS+Veh, however, demonstrated IEC lesions on the luminal border as well as crypt distortion. DSS+Pax showed histological architecture similar to that of Control, including apparent improvements in crypt structure and arrangement. TEM images revealed ultrastructural changes within the intercellular space of IECs in DSS-treated colons (FIG. 11A). DSS+Veh demonstrated edema (arrows) in the intercellular space, resulting in IEC separation. This ultrastructural change was only seen in DSS+Veh, as DSS+Pax exhibited closely-packed IECs with no edema in between. To quantify changes in crypt architecture, crypt widths were measured across all groups using H&E stains (FIG. 11B). DSS+Veh increased the average crypt width by 124% ($p=0.030$) compared to Control, which was inhibited in DSS+Pax, as DSS+Pax was not different from Control ($p=0.641$). Moreover, a distribution curve revealed a rightward shift in crypt widths from Control to DSS+Veh, which was significantly ($p\leq0.05$) improved by DSS+Pax. DSS+Pax exhibited significantly ($p\leq0.05$) more "intermediate" (i.e., 35-40 μm and 40-45 μm) crypt widths and significantly fewer "wide" (i.e., 60-65 μm and >75 μm) crypt widths compared to DSS+Veh (FIG. 11C).

Figure 11D:
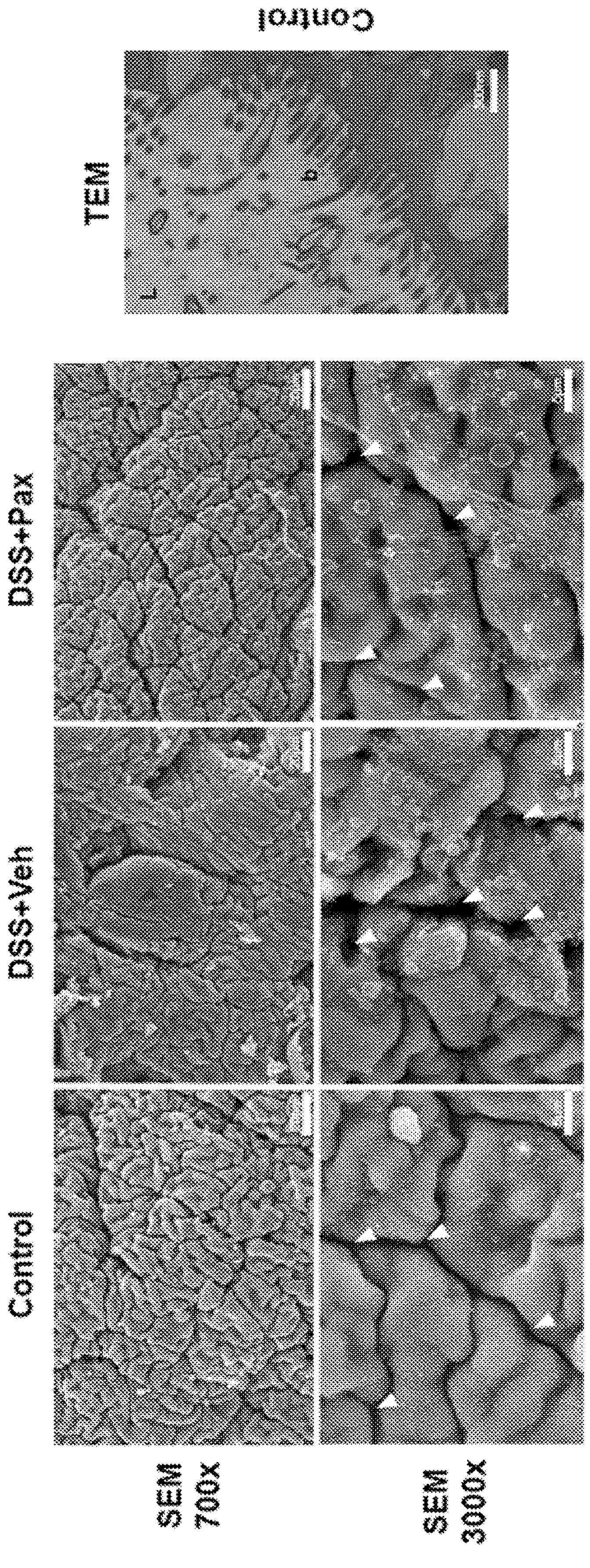
FIG. 11D illustrates representative scanning electron microscopy (SEM) images of the distal colon taken at 700× (scale bar=20 μm) showing mucosal flattening (dark arrows); TEM image of a Control distal colon showing a normal brush border (b) on the luminal (L) surface of LECs (scale bar=500 μm); and representative SEM images of the distal colon taken at 3000× (scale bar=5 μm) showing crypts (white arrows).

EM was leveraged to better visualize mucosal architecture. SEM 700× images showed Control mucosa had a plump, smooth, and velvety appearance documenting healthy in-tact epithelium and brush border (FIG. 11D). DSS+Veh demonstrated areas of mucosal flattening and solidity (red arrow), as well as loss of the velvety appearance, indicating damage to the epithelium and brush border (FIG. 11D). DSS+Pax exhibited a mucosal architecture similar to Control, as the plump and velvety appearance was preserved. TEM showed a normal example (i.e., Control) of the brush border (b) on the luminal (L) surface of colonic enterocytes (FIG. 11D). This ultrastructural characteristic was likely preserved in DSS+Pax, contributing to its more normal appearance (FIG. 11D). SEM 3000× images showed differences between crypt widths (white arrows) across groups (FIG. 11D). Control crypts were tightly packed and well-arranged. DSS+Veh showed severe widening and gaping of the crypts. This phenomena was partially rescued by DSS+Pax, evidenced by apparent improvements to crypt architecture.

Panaxynol Inhibits the Loss of Goblet Cells Per Crypt and Preserves Mucus Loss Due to DSS.

Figure 12A:
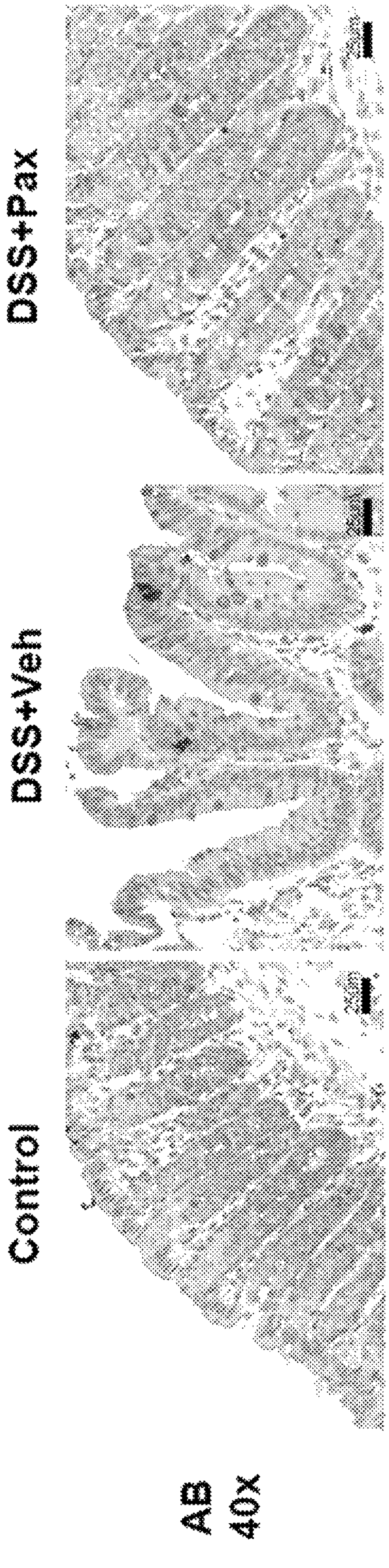
FIG. 12A illustrates representative images of Alcian Blue (AB) staining of the distal colon taken at 40× (scale bar=25 μm).
Figure 12B:
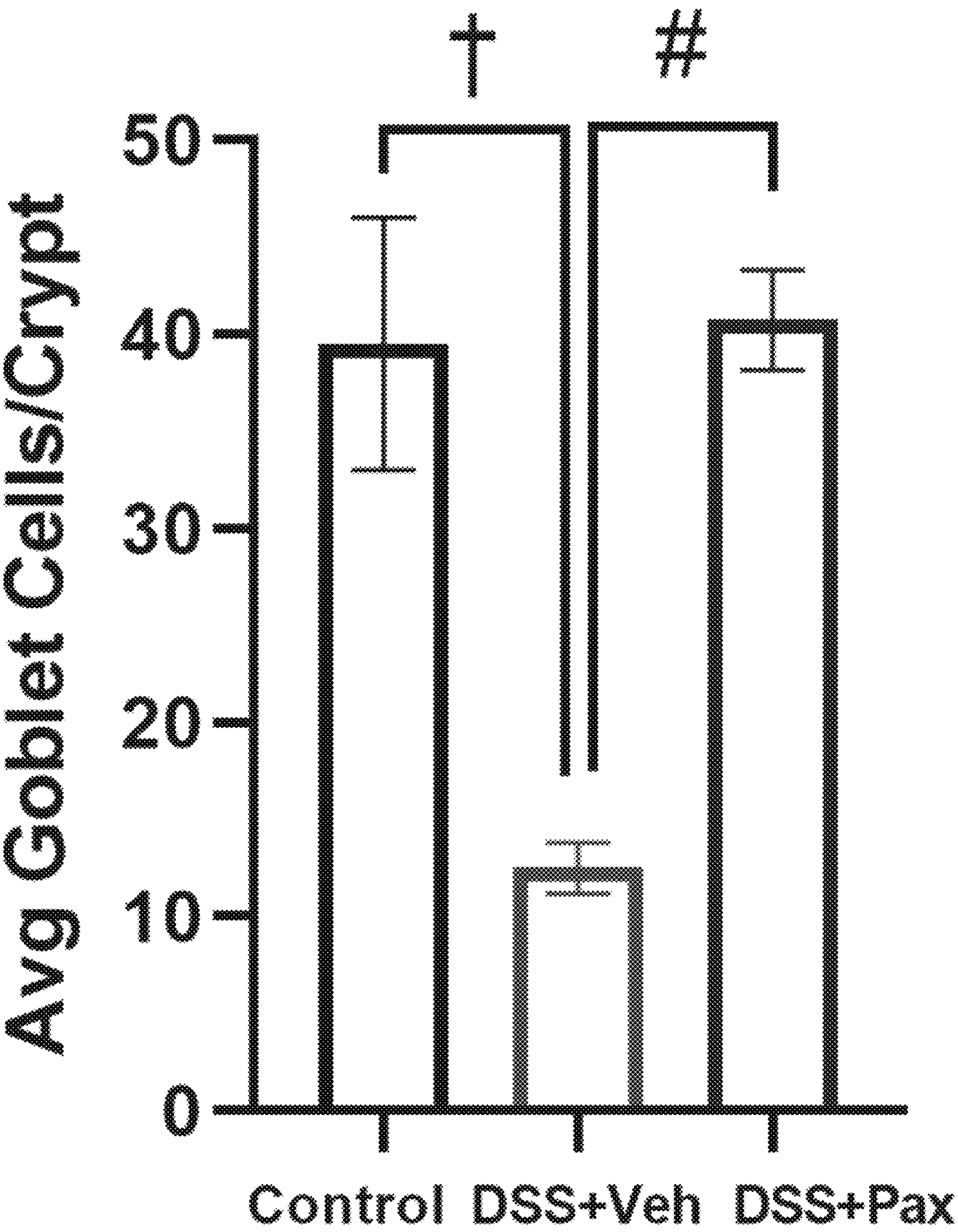
FIG. 12B illustrates average goblet cell count per crypt (n=2-3/group).
Figure 12C:
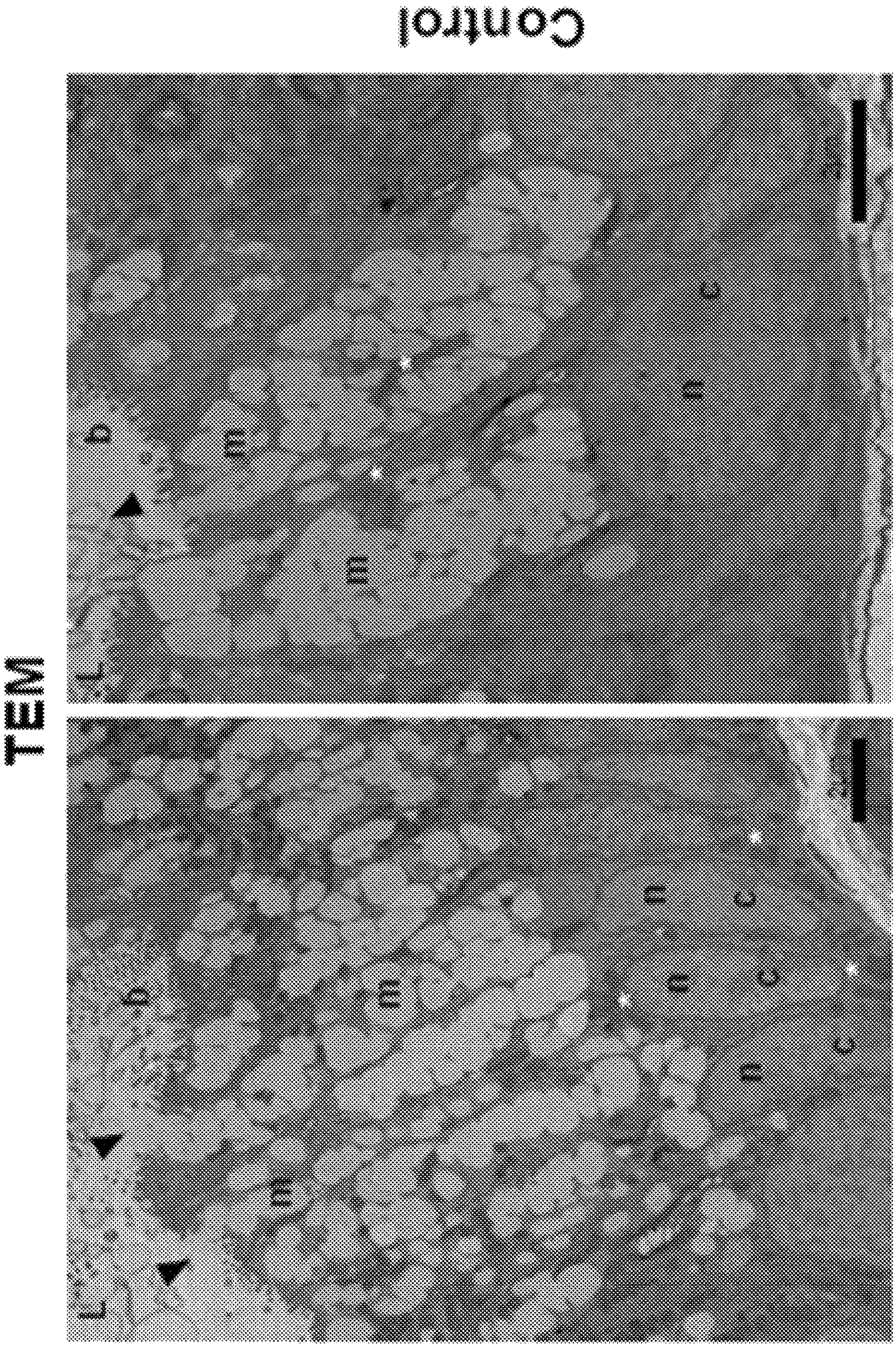
FIG. 12C illustrates transmission electron microscopy (TEM) images of the distal colon in Control showing normal intestinal epithelial cell (IEC) architecture (scale bar=2 μm). All LECs have defined nuclear envelopes with a nucleus (n) and a chromatin-dense nucleolus (c) and abundant mitochondria (asterisks). Enterocytes displayed the brush border (b) along the luminal border. Goblet cells displayed mucus granules (m) that were actively secreting mucus (arrows) into the lumen (L).
Figure 12D:
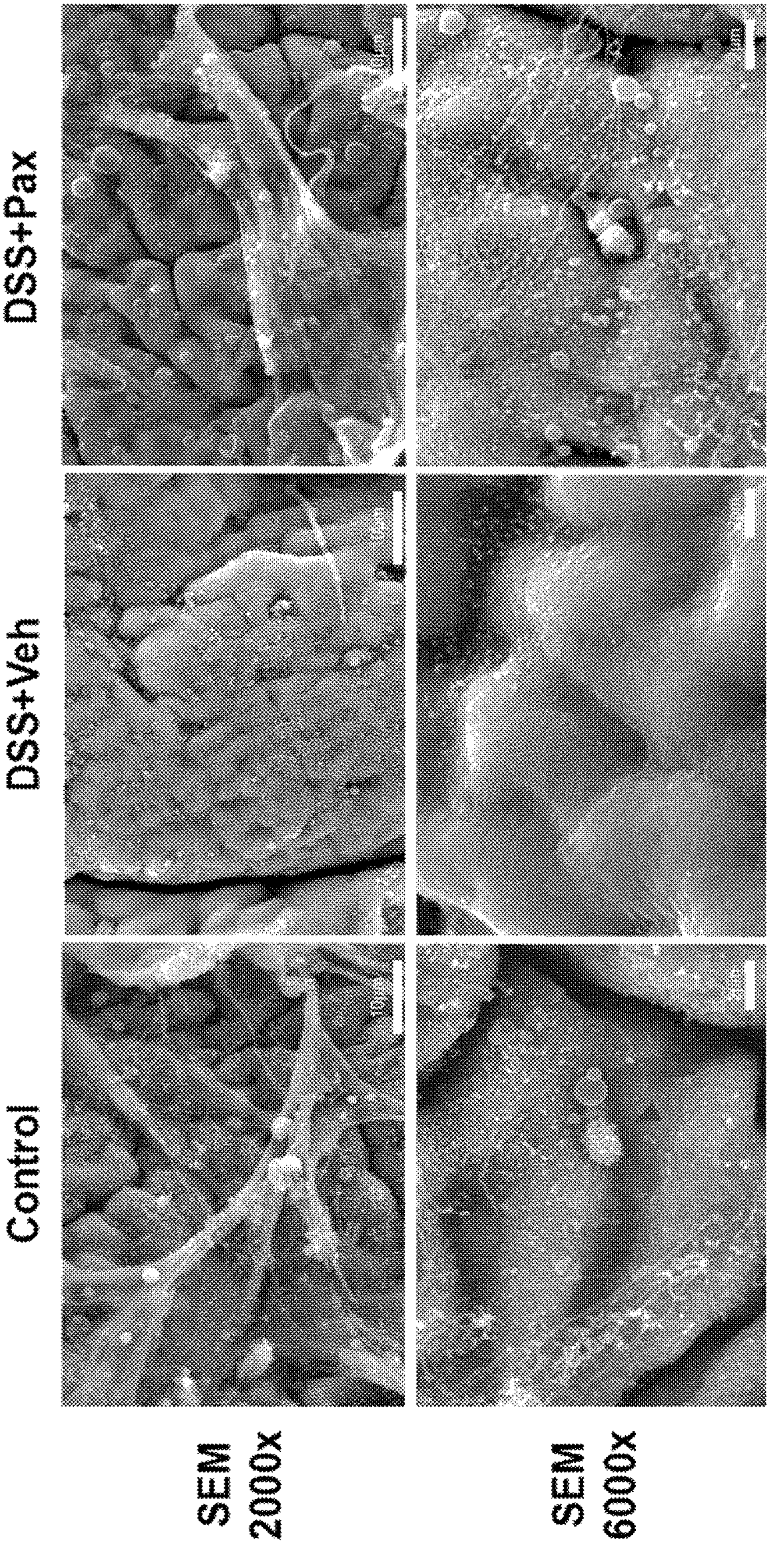
FIG. 12D illustrates representative scanning electron microscopy (SEM) images of the distal colon taken at 2000× (scale bar=10 μm) and 6000× (scale bar=2 μm) showing mucus (top arrows) and goblet cells (bottom arrows).

AB images revealed positively-stained mucin protein (i.e., mucus) in the distal colon (FIG. 12A). The average goblet cell count per crypt in Control was ~40 (FIG. 12B). DSS+Veh decreased the goblet cell count per crypt by 75% ($p=0.001$) compared to Control, which was rescued in DSS+Pax ($p=0.0003$). DSS+Pax successfully ameliorated the DSS-induced eradication in goblet cells per crypt and preserved a similar count to Control. TEM showed normal examples (i.e., Control) of colonic ultrastructure and IECs (FIG. 12C). All IECs had a clear nuclear envelope with a nucleus (n) and chromatin-dense nucleolus (c), as well as abundant mitochondria (asterisks). Enterocytes displayed the brush border (b) along the luminal surface. Goblet cells displayed mucus granules (m) that were actively secreting mucus (black arrows) into the lumen (L). To investigate the DSS-induced changes to mucus and goblet cells, SEM was performed on all groups at two magnifications (FIG. 12D). 2000× images showed Control demonstrated plentiful and abundant mucus throughout the mucosa (arrows). DSS+Veh mucosa exhibited scarcity and bareness of mucus compared to Control. DSS+Pax, however, exhibited more areas of mucus formation, preservation, and abundance (arrows), which appeared similar to Control. 6000× images identified normal and abundant goblet cells (arrows) in Control. Again, DSS+Veh exhibited scarcity and bareness of goblet cells throughout the mucosa, whereas DSS+Pax preserved goblet cells throughout (arrows), confirming AB results.

Panaxynol Suppresses Macrophage Polarization in the Colonic Lamina Propria.

Figure 13A:
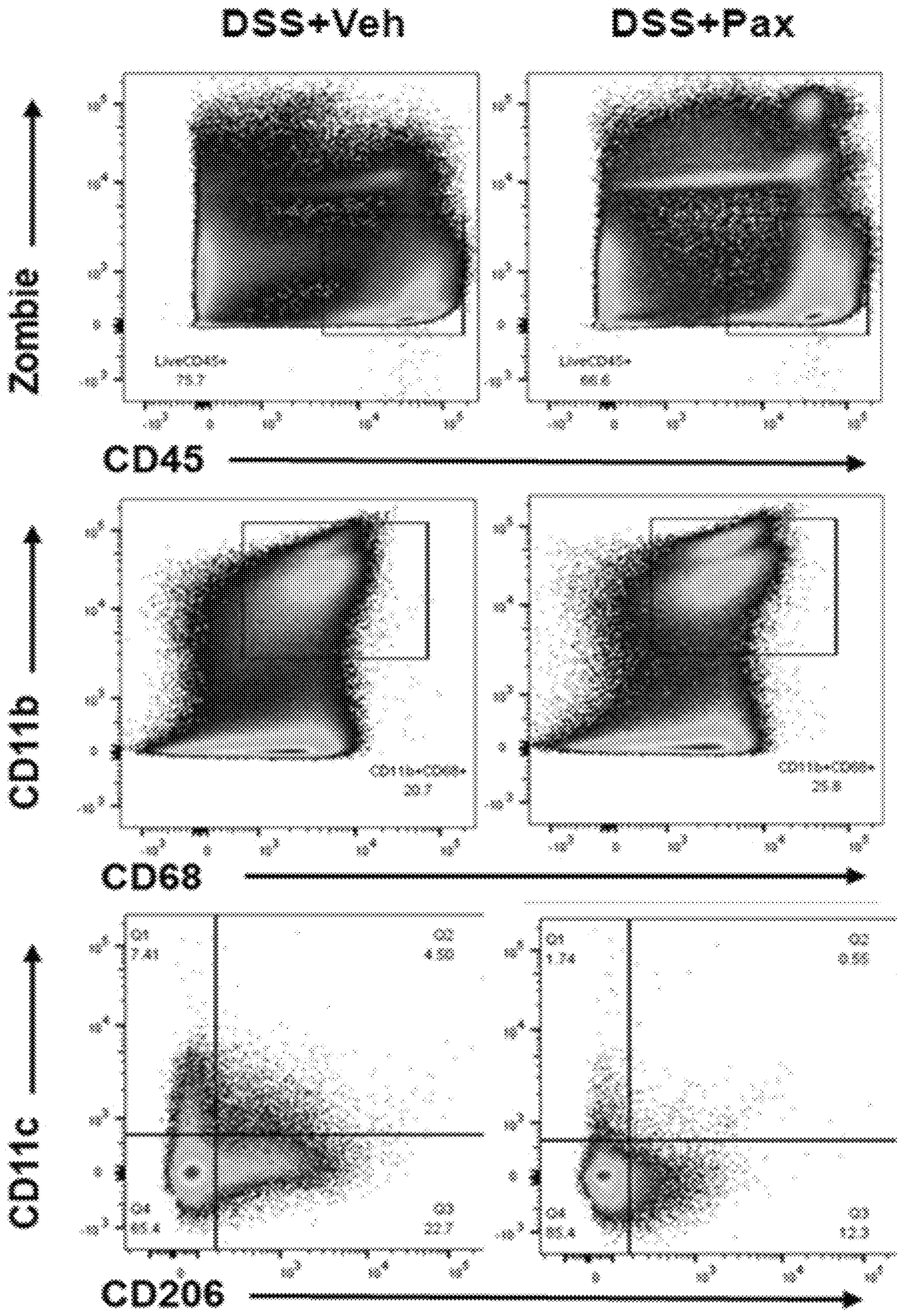
FIG. 13A illustrates representative flow plots of gating strategy for macrophages: colonic lamina propria (LP) cells were gated for non-debris singlets and considered live immune cells with ZombieGreenNeg/Low and $CD45^+$.
Figure 13B:
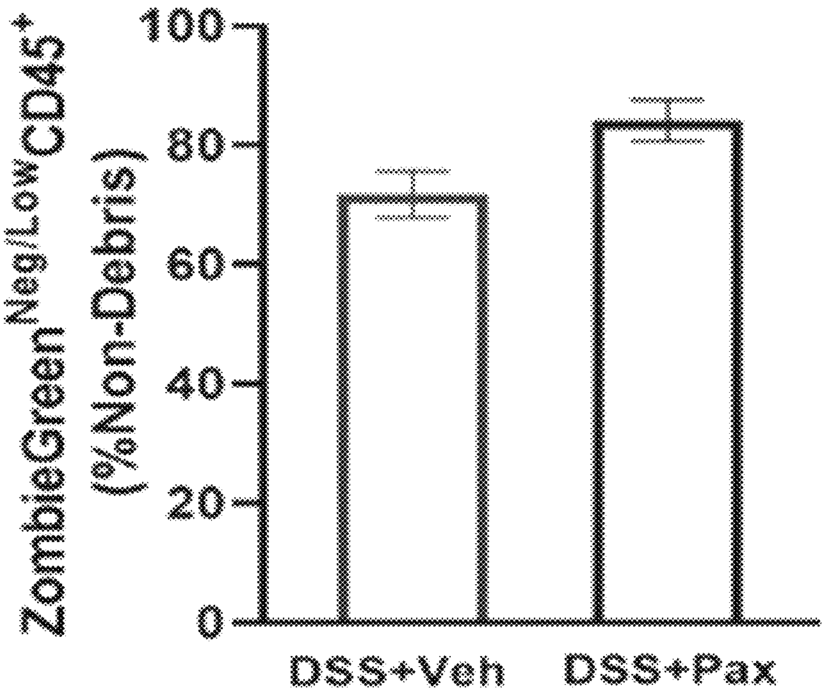
FIG. 13B illustrates relative percentage of macrophage phenotypes in the colonic LP (n=3-4/group): $LiveCD45^+$ immune cells.
Figure 13C:
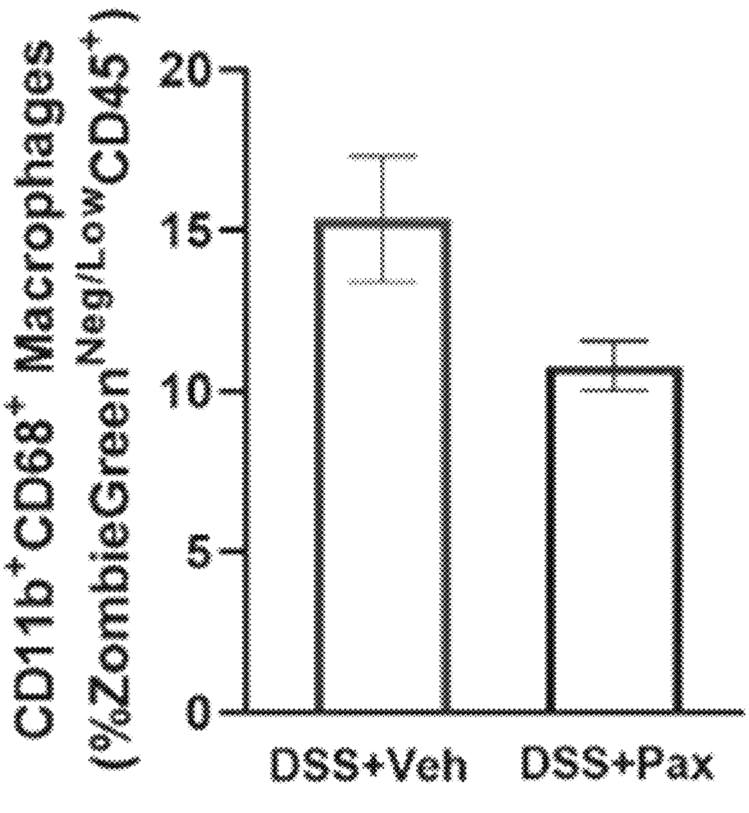
FIG. 13C illustrates relative percentage of macrophage phenotypes in the colonic LP (n=3-4/group): $CD11b^+CD68^+$ overall macrophages.
Figure 13D:
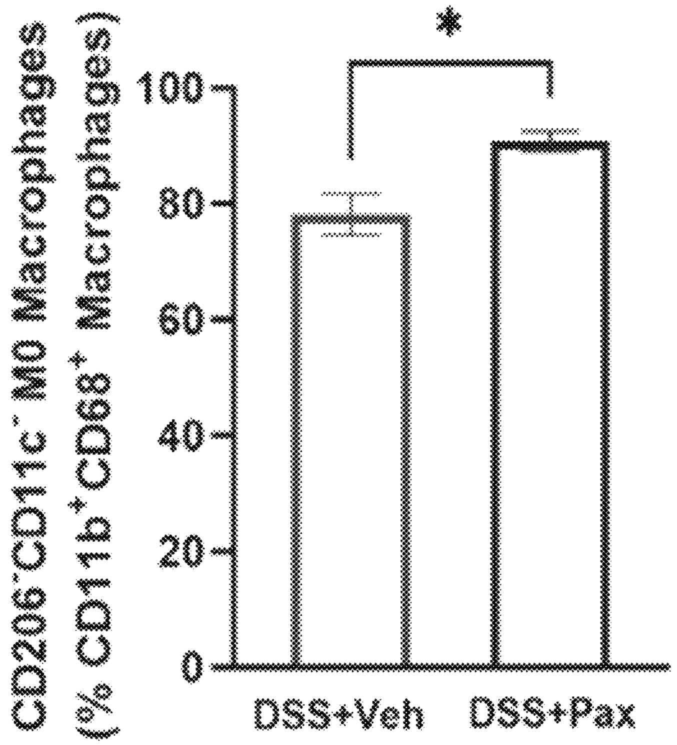
FIG. 13D illustrates relative percentage of macrophage phenotypes in the colonic LP (n=3-4/group): $CD206^-$ $CD11c^-$ M0 macrophages.
Figure 13E:
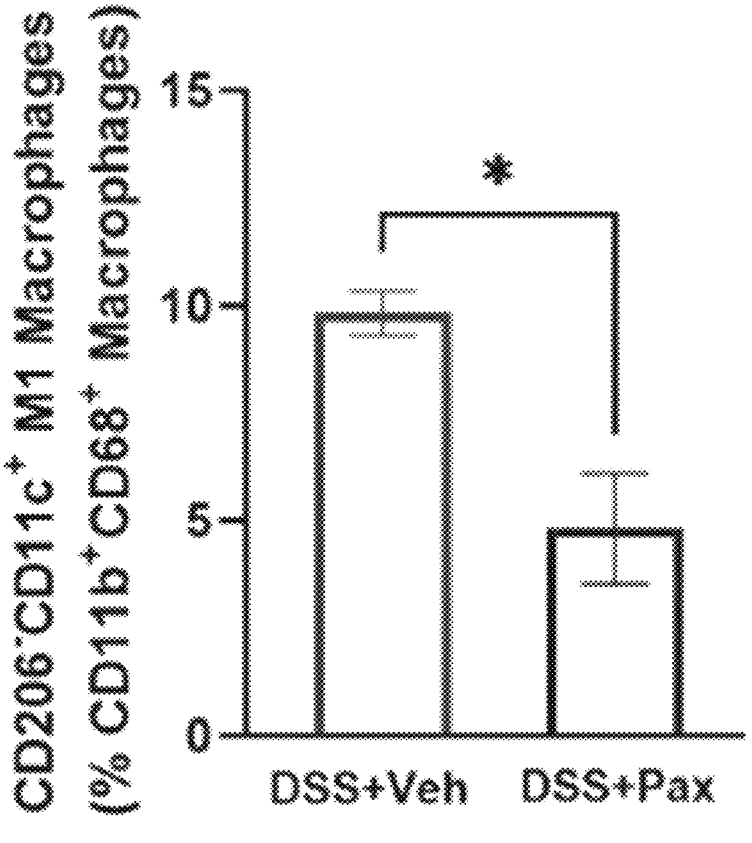
FIG. 13E illustrates relative percentage of macrophage phenotypes in the colonic LP (n=3-4/group): $CD206^-$ $CD11c^+$ M1 macrophages.
Figure 13F:
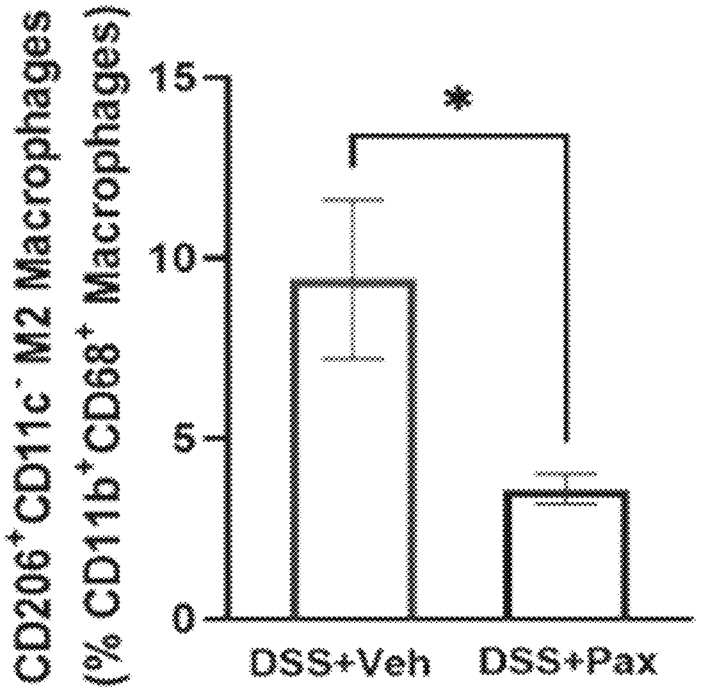
FIG. 13F illustrates relative percentage of macrophage phenotypes in the colonic LP (n=3-4/group): $CD206^+$ $CD11c^-$ M2 macrophages.
Figure 13G:
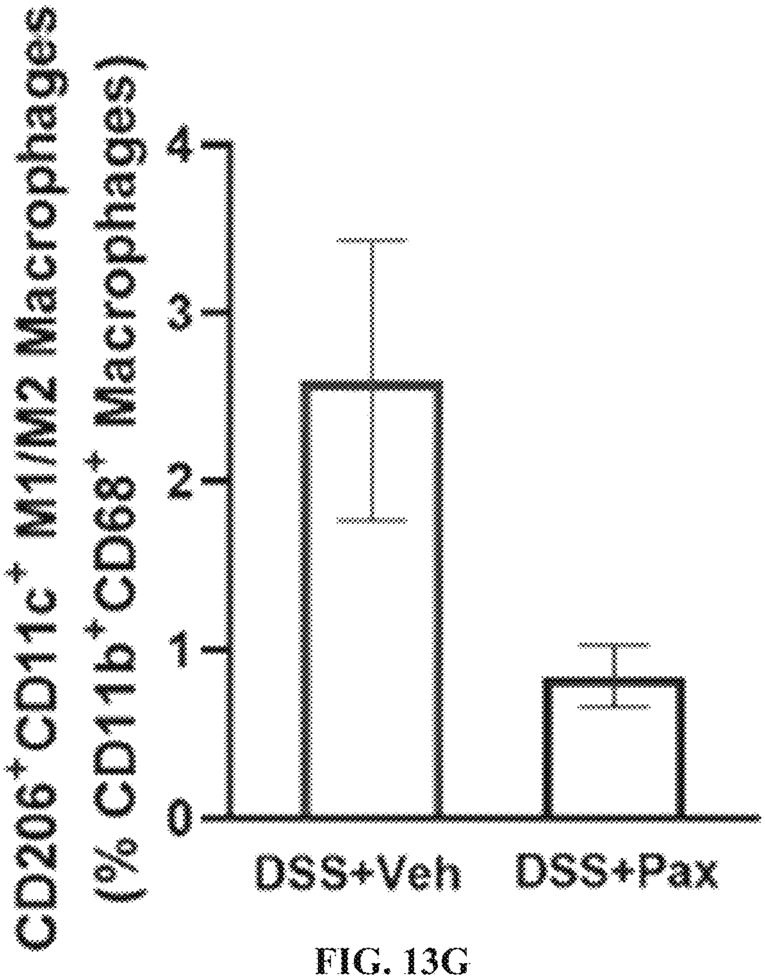
FIG. 13G illustrates relative percentage of macrophage phenotypes in the colonic LP (n=3-4/group): $CD206^+$ $CD11c^+$ M1/M2 transitional macrophages.
Figure 13H:
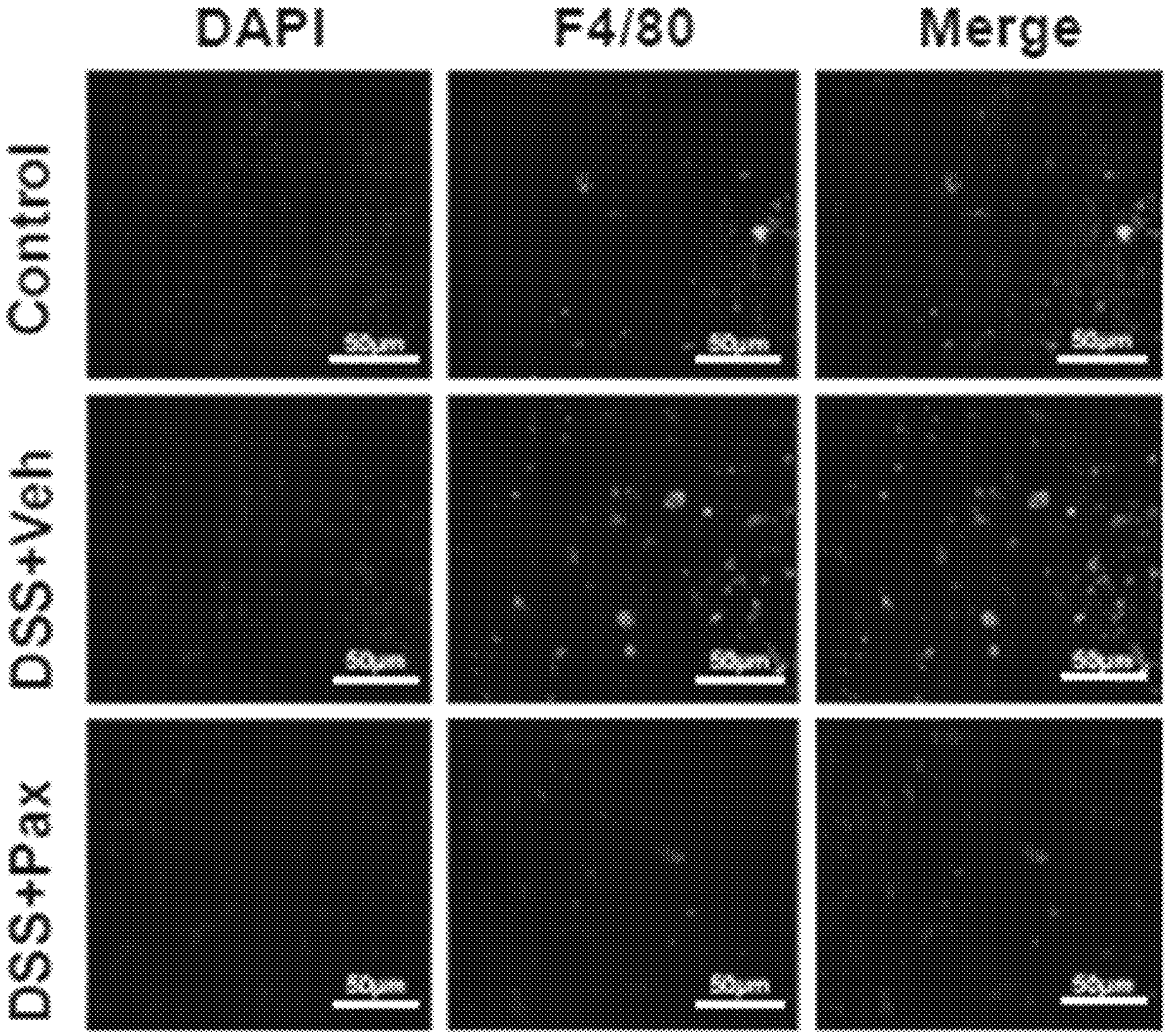
FIG. 13H illustrates representative F4/80 immunofluorescence images of the distal colon taken at 20× (scale bar=50 μm).
Figure 13I:
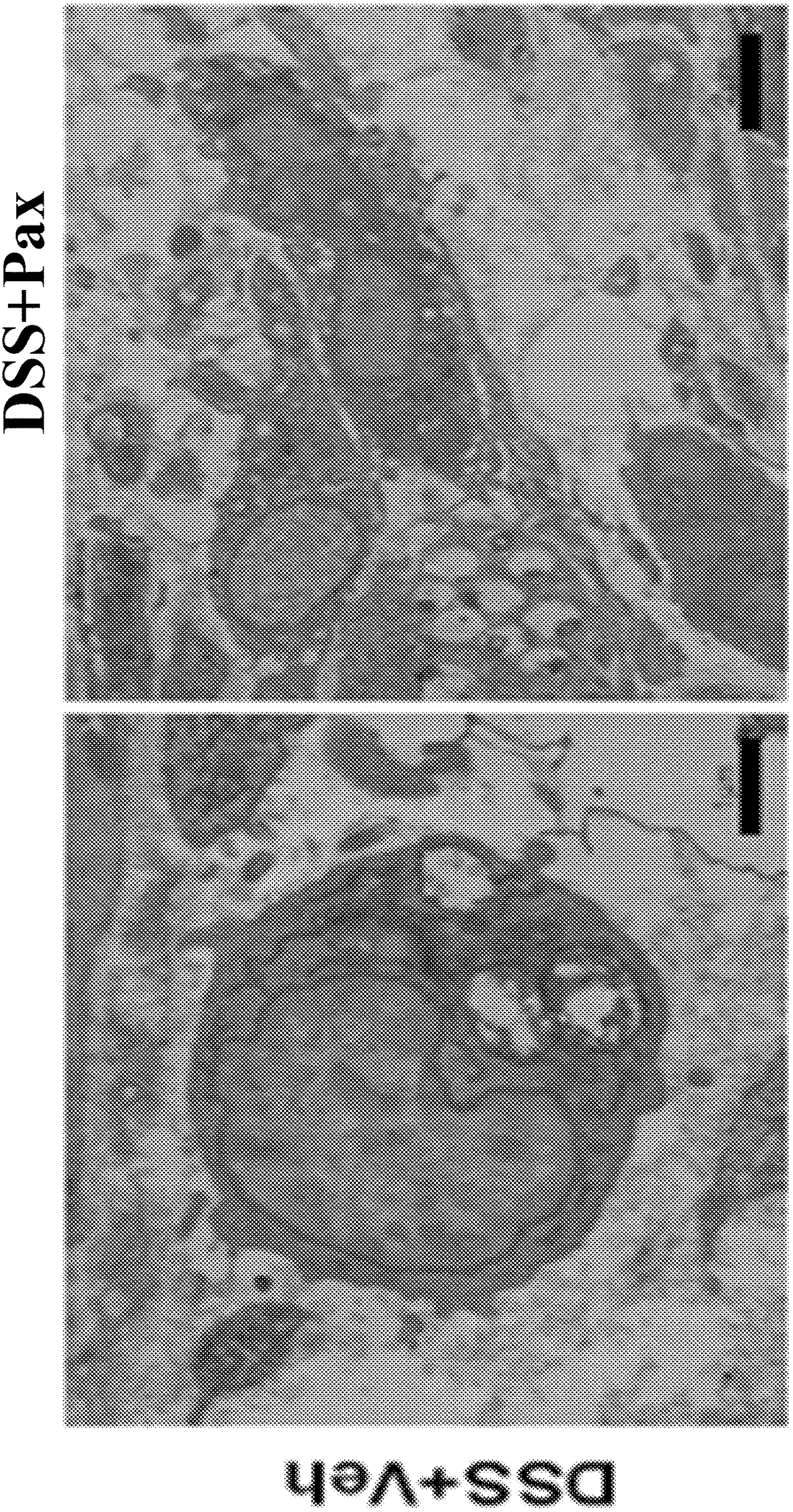
FIG. 13I illustrates representative transmission electron microscopy (TEM) images showing phagocytic immune cells in the distal colon (scale bar=1 μm and 2 μm).

Macrophages play a key role in the regulation of colitis and intestinal homeostasis. To investigate the impact of panaxynol on macrophage phenotypes in the context of acute colitis, flow cytometry was performed in the colonic LP. DSS alone significantly increased relative LiveCD45$^+$ immune cells (31.5±11.5% vs 78.0±3.3%, $p=0.0004$) compared to Controls. Controls were then excluded from macrophage and macrophage phenotype analysis, given the apparent changes in parent populations. Relative percentage of macrophage phenotypes in the colonic LP are shown in DSS-treated groups (FIGS. 13B-5G). DSS+Pax exhibited a trending increase ($p=0.056$) in LiveCD45$^+$ immune cells (FIG. 13B) and decrease ($p=0.07$) in CD11b$^+$CD68$^+$ macrophages (FIG. 13C) compared to DSS+Veh, although these differences were not statistically significant. DSS+Pax significantly ($p=0.019$) increased the relative abundance of naïve (M0) macrophages (FIG. 13D) and decreased both M1 ($p=0.011$) and M2 ($p=0.041$) macrophages (FIGS. 13E-13F) compared to DSS+Veh. There were no significant differences in transitional (M1/M2) macrophages ($p=0.085$) within DSS-treated groups (FIG. 13G). In support of the flow cytometry findings, DSS+Veh demonstrated increased staining for F4/80$^+$ macrophages in the colonic LP compared to Control and DSS+Pax (FIG. 13H). TEM images revealed interesting immune cells, which appeared to be phagocytic in nature and were only apparent in the DSS+Veh group (FIG. 13I). Although it was unclear whether these cells were M1 or M2 macrophages, these specific immune cells appeared phagocytic in nature and were only apparent in the DSS+Veh group.

Panaxynol Increases Regulatory T-Cells in the Colonic Lamina Propria.

Figure 14A:
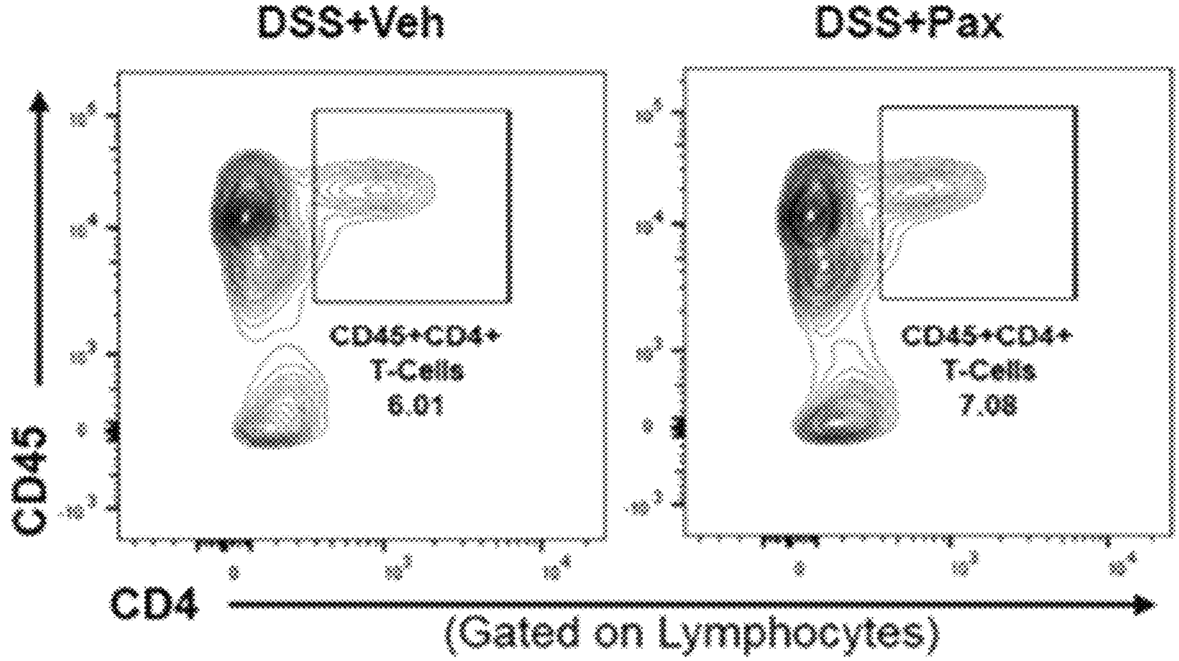
FIG. 14A illustrates representative flow plots of gating strategy for T-cells: colonic lamina propria (LP) cells were gated for non-debris singlets and considered immune cells with $CD45^+$. From the $CD45^+$ immune cell population, $CD4^+$ cells were identified as helper T-cells.
Figure 14B:
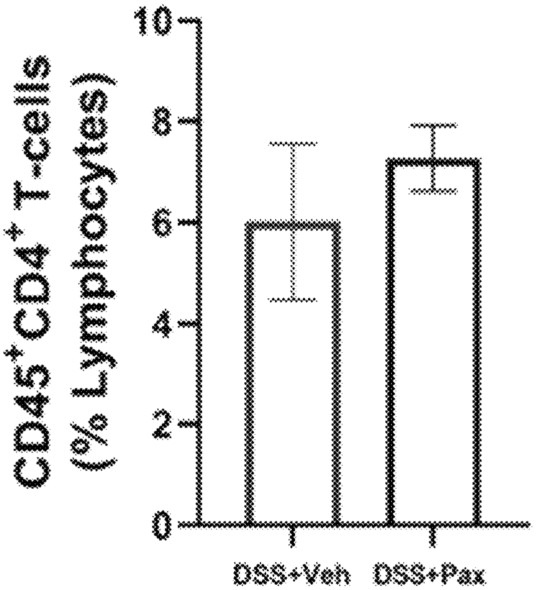
FIG. 14B illustrates relative percentage of $CD45^+CD4^+$ helper T-cells in the colonic LP (n=3-4/group).
Figure 14C:
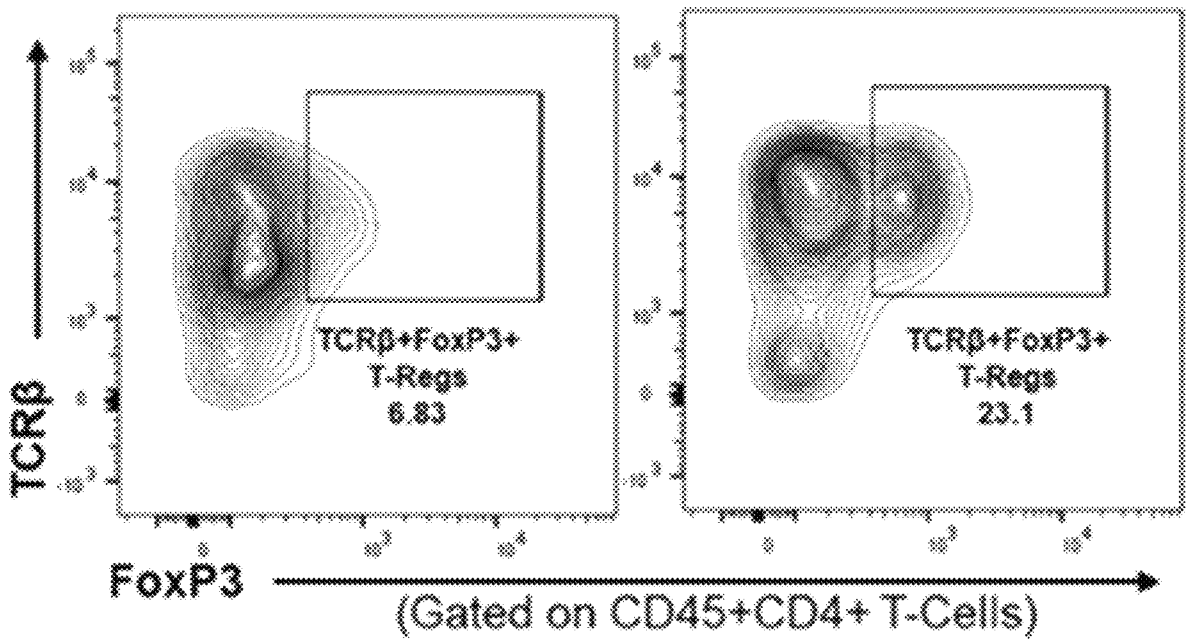
FIG. 14C illustrates from the $CD45^+CD4^+$ population, $TCR\beta^+FoxP3^+$ cells were identified as regulatory T-cells.
Figure 14D:
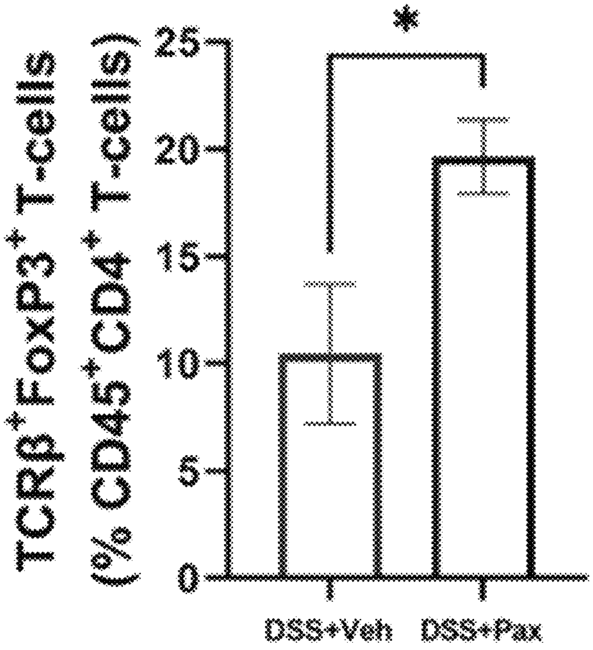
FIG. 14D illustrates relative percentage of $TCR\beta^+FoxP3^+$ regulatory T-cells in the colonic LP (n=3-4/group).

T-regs also play a vital role in combatting inflammation and consequently controlling colitis. To investigate whether panaxynol influenced T-regs in acute colitis, flow cytometry was performed in the colonic LP. Relative percentage of T-cell phenotypes in the colonic LP are shown in DSS-treated groups (FIGS. 14A-14D). From the lymphocyte population, CD45$^+$CD4$^+$ cells were identified as helper T-cells (FIG. 14A). There were no significant differences ($p=0.446$) in CD45$^+$ CD4$^+$ helper T-cells between DSS-treated groups (FIG. 14B). From the CD45$^+$CD4$^+$ population, TCRβ$^+$FoxP3$^+$ cells were identified as regulatory T-cells (FIG. 14C). DSS+Pax significantly increased ($p=0.027$) TCRβ$^+$FoxP3$^+$ T-regs in the colonic LP compared to DSS+Veh (FIG. 14D).

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A method of treating an inflammatory disease, the method comprises administering to a subject in need thereof panaxynol and measuring expression level of at least one biomarker in a subject sample prior to and after administration of the panaxynol, wherein the panaxynol is administered to the subject in need thereof at a dosage of from about 2 mg/kg to about 5 mg/kg, wherein the at least one biomarker is IL-10, IL-$17^+$, IL-1β, IL-6, IL-13, TGF-β, Foxp3, $CD3^+$, $CD45^+$, $CD8^+$, CD11b, CD68, or any combination thereof, wherein the inflammatory disease is selected from the group consisting of colon cancer, colitis, and colorectal cancer.

2. The method of claim 1, wherein the panaxynol is administered orally, intravenously, subcutaneously, or intratumorally.

3. The method of claim 1, wherein the panaxynol is administered at least once per week to the subject in need thereof.

4. The method of claim 1, wherein the panaxynol is administered at least three times per week to the subject in need thereof.

5. The method of claim 1, wherein the inflammatory disease is colon cancer.

6. The method of claim 1, wherein the inflammatory disease is colitis.

7. The method of claim 1, wherein the inflammatory disease is colorectal cancer.

8. The method of claim 1, further comprising:

comparing expression level of the at least one biomarker prior to and after administration of the panaxynol; and continuing or ceasing administration of the panaxynol based on the biomarker expression level.

9. The method of claim 8, wherein the panaxynol increases the expression level of at least one biomarker by at least about 10% compared to a control sample.

10. The method of claim 8, wherein the panaxynol decreases the expression level of at least one biomarker by at least about 10% compared to a control sample.

* * * * *